US012742183B2

(12) United States Patent
Davalos et al.

(10) Patent No.: US 12,742,183 B2
(45) Date of Patent: Sep. 22, 2026

(54) METHOD FOR INTRACELLULAR DELIVERY OF COMPOUNDS USING CELL FORCE AND SHAPE WITH ELECTRIC FIELDS

(71) Applicant: VIRGINIA TECH INTELLECTUAL PROPERTIES, INC., Blacksburg, VA (US)

(72) Inventors: Rafael Davalos, Blacksburg, VA (US); Amrinder Nain, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 1219 days.

(21) Appl. No.: 17/753,284

(22) PCT Filed: Aug. 28, 2020

(86) PCT No.: PCT/US2020/048625

§ 371 (c)(1),
(2) Date: Feb. 25, 2022

(87) PCT Pub. No.: WO2021/041979

PCT Pub. Date: Mar. 4, 2021

(65) Prior Publication Data

US 2022/0290183 A1 Sep. 15, 2022

Related U.S. Application Data

(60) Provisional application No. 62/894,314, filed on Aug. 30, 2019.

(51) Int. Cl.
*C12N 15/87* (2006.01)
*C12N 13/00* (2006.01)

(52) U.S. Cl.
CPC ............. *C12N 15/87* (2013.01); *C12N 13/00* (2013.01)

(58) Field of Classification Search
None
See application file for complete search history.

(56) References Cited

U.S. PATENT DOCUMENTS

| | | | |
|---|---|---|---|
| 8,580,181 | B1 | 11/2013 | Beachley et al. |
| 9,029,149 | B2 | 5/2015 | Nain |
| 9,753,023 | B2 | 9/2017 | Nain et al. |
| 2007/0269481 | A1 | 11/2007 | Li et al. |
| 2008/0091135 | A1 | 4/2008 | Draghia-Akli et al. |
| 2011/0106221 | A1 | 5/2011 | Neal et al. |
| 2017/0266438 | A1 | 9/2017 | Sano et al. |

OTHER PUBLICATIONS

Ivey et al., "Enhancing Irreversible Electroporation by Manipulating Cellular Biophysics with a Molecular Adjuvant" 113 Biophysical Journal 472-480 (Year: 2017).*

Badkar et al., Enhancement of Transdermal lontophoretic Delivery of a Liposomal Formulation of Colchicine by Electroporation 6 Drug Delivery 111-115 (Year: 1999).*

Chicaybam et al., An Efficient Electroporation Protocol for the Genetic Modification of Mammalian Cells 4 Frontiers in Bioengineering and Biotechnology 99, 1-13 (Year: 2017).*

International Search Report for PCT/US2020/48625 mailed Nov. 27, 2020.

Arena et al., "High-frequency irreversible electroporation (H-FIRE) for non-thermal ablation without muscle contraction," BioMedical Engineering OnLine, vol. 10, No. 102, 2011, 21 pages.

Berghofer et al., "Nanosecond electric pulses trigger actin responses in plant cells," Biochemical and Biophysical Research Communications. vol. 387, 2009, pp. 590-595.

Bird, S.D., "Corrigendum to Calcium mediates cell shape change in human peritoneal mesothelial cells," Cell Calcium, vol. 74, 2018, pp. 186.

Carr et al., "Calcium-independent disruption of microtubule dynamics by nanosecond pulsed electric fields in U87 human glioblastoma cells," Scientific Reports, vol. 7, No. 41267, 2017, 12 pages.

Cemazar et al., "Enhanced contactless dielectrophoresis enrichment and isolation platform via cell-scale microstructures," Biomicrofluidics, vol. 10, 2016, pp. 014109-1-014109-14.

Cemazar M., "Effects of Electroporation of Mammalian Cells on Cytoskeleton and Intercellular Connections," in: Handbook of Electroporation, Springer Publishing, 2017, pp. 307-321.

Charras et al., "Reassembly of contractile actin cortex in cell blebs," The Journal of Cell Biology, vol. 175, No. 3, Nov. 6, 2006, pp. 477-490.

Chen et al., "Fluidization and rresolidification of the Human Bladder Smooth Muscle Cell in Response to Transient Stretch," PLoS ONE, vol. 5, Issue 8, Aug. 2010, 7 pages.

Chen et al., "The ER Ca2+ sensor STIM1 regulates actomyosin contractility of migratory cells," Journal of Cell Science, vol. 126, No. 5, 2013, pp. 1260-1267.

Chikina et al., "Time-resolved ultrastructure of the cortical actin cytoskeleton in dynamic membrane blebs," Journal of Cell Biology, vol. 218, No. 2, 2019, pp. 445-454.

(Continued)

*Primary Examiner* — Nancy J Leith

(74) *Attorney, Agent, or Firm* — Thomas | Horstemeyer, LLP

(57) ABSTRACT

In accordance with the purpose(s) of the present disclosure, as embodied and broadly described herein, the disclosure, in one aspect, relates to methods for modifying cells such as, for example, changing shape, cell force, and/or modifying structural integrity of the cells. In a further aspect, the disclosure relates to controlling membrane permeability in cells by applying an electric current, where the cells are in contact with a polymeric nanofiber array and wherein direction and voltage of the electric current can be modified to induce the desired cellular response. In some aspects, the method results in higher survivability for cells during electroporation, greater permeability to molecules and/or drugs of different sizes, and greater transfection efficiencies for rare primary cells.

18 Claims, 38 Drawing Sheets

(56) References Cited

OTHER PUBLICATIONS

Chiu et al., "A microfluidic toolbox for cell fusion," Journal of Chemical Technology & Biotechnology, vol. 91, No. 1, 2016: 16-24, 20 pages.
Chopinet et al., "AFM Sensing Cortical Actin Cytoskeleton Destabilization During Plasma Membrane Electropermeabilization," Cytoskeleton, vol. 71, Oct. 2014, pp. 587-594.
Chopinet et al., "Destabilization induced by electropermeabilization analyzed by atomic force microscopy," Biochimica et Biophysica Acta, vol. 1828, 2013, pp. 2223-2229.
Chu et al., "Electroporation for the efficient transfection of mammalian cells with DNA," Nucleic Acids Research, vol. 15, No. 3, 1987, pp. 1311-1326.
Conklin et al., "Local calcium transients contribute to disappearance of pFAK, focal complex removal and deadhesion of neuronal growth cones and fibroblasts," Developmental Biology, vol. 287, 2005, pp. 201-212.
D'Souza et al., "Calcium-stimulated disassembly of focal adhesions mediated by an ORP3/IQSec1 complex," eLife, vol. 9, 2020, 33 pages.
Davalos et al., "Tissue ablation with irreversible electroporation," Annals of Biomedical Engineering, vol. 33, No. 2, Feb. 2005, pp. 223-231.
Dutta et al., "Effects of nanosecond pulse electric fields on cellular elasticity," Micron, vol. 72, May 2015: 15-20, 13 pages.
Ford et al., "Nanosecond pulsed electric fields stimulate apoptosis without release of pro-apoptotic factors from mitochondria in B16f10 melanoma," Archives of Biochemistry and Biophysics, vol. 497, 2010, pp. 82-89.
Frandsen et al., "Direct Therapeutic Applications of Calcium Electroporation to Effectively Induce Tumor Necrosis," Cancer Research, vol. 72, No. 6, Mar. 15, 2012, pp. 1336-1341.
Geboers et al., "High-Voltage Electrical Pulses in Oncology: Irreversible Electroporation, Electrochemotherapy, Gene Electrotransfer, Electrofusion, and Electroimmunotherapy," Radiology, vol. 295, No. 2, May 2020, pp. 254-272.
Giannone et al., "Calcium Oscillations Trigger Focal Adhesion Disassembly in Human U87 Astrocytoma Cells," Journal of Biological Chemistry, vol. 277, No. 29, Jul. 19, 2002, pp. 26364-26371.
Giannone et al., "Calcium Rises Locally Trigger Focal Adhesion Disassembly and Enhance Residency of Focal Adhesion Kinase at Focal Adhesions," Journal of Biological Chemistry, vol. 279, No. 27, Jul. 2, 2004, pp. 28715-28723.
Gissel et al., "Electroporation and Cellular Physiology," in: Clinical Aspects of Electroporation, Springer Publisher, 2011, pp. 9-17.
Goswami et al., "Influence of Pulsed Electric Fields and Mitochondria-Cytoskeleton Interactions on Cell Respiration," Biophysical Journal, vol. 114, Jun. 19, 2018, pp. 2951-2964.
Gothelf et al., "Electrochemotherapy: results of cancer treatment using enhanced delivery of bleomycin by electroporation," Cancer Treatment Reviews, vol. 29, 2003, pp. 371-387.
Graybill et al., "Cytoskeletal Disruption after Electroporation and Its Significance to Pulsed Electric Field Therapies," Cancers, vol. 12, 2020, 35 pages.
Guo et al., "Cell volume change through water efflux impacts cell stiffness and stem cell fate," PNAS, vol. 114, No. 41, Sep. 25, 2017, pp. E8618-E8627.
Harkin et al., "Effects of Electroporation on the Tubulin Cytoskeleton and Directed Migration of Corneal Fibroblasts Cultured Within Collagen Matrices," Cell Motility and the Cytoskeleton, vol. 35, 1996, pp. 345-357.
Hibino et al., "Time courses of cell electroporation as revealed by submicrosecond imaging of transmembrane potential," Biophysical Journal, vol. 64, Jun. 1993, pp. 1789-1800.
Hohenberger et al., "Plant actin controls membrane permeability," Biochimica et Biophysica Acta, vol. 1808, 2011, pp. 2304-2312.
Hu et al., "Cell electrofusion in microfluidic devices: A review," Sensors and Actuators B, vol. 178, 2013, pp. 63-85.
Hiu et al., "Model study of electroporation effects on the dielectrophoretic response of spheroidal cells," Journal of Applied Physics, vol. 106, 2009, p. 024701-1-024701-8.
Jana et al., "Crosshatch nanofiber networks of tunable interfiber spacing induce plasticity in cell migration and cytoskeletal response," FASEB Journal, vol. 33, Issue 10, Oct. 2019, pp. 10618-10632.
Jarm et al., "Antivascular effects of electrochemotherapy: implications in treatment of bleeding metastases," Expert Review of Anticancer Therapy, vol. 10, No. 5, 2010, pp. 729-746.
Kanduser et al., "Cell membrane fluidity related to electroporation and resealing," European Biophysics Journal, vol. 35, 2006, pp. 196-204.
Kanthou et al., "The endothelial cytoskeleton as a target of electroporation-based therapies," Molecular Cancer Therapeutics, vol. 5, Issue 12, Dec. 2006, pp. 3145-3152.
Kotnik et al., "Induced Transmembrane Voltage and Its Correlation with Electroporation-Mediated Molecular Transport," Journal of Membrane Biology, vol. 236, 2010, pp. 3-13.
Kotnik et al., "Membrane Electroporation and Electropermeabilization: Mechanisms and Models," Annual Review of Biophysics, vol. 48, 2019, pp. 63-91.
Kotnik et al., "Time course of transmembrane voltage induced by time-varying electric fields—A method for theoretical analysis and its application," Bioelectrochemistry and Bioenergetics, vol. 45, Mar. 1998, pp. 3-16.
Krassowska et al., "Modeling Electroporation in a Single Cell," Biophysical Journal, vol. 92, Jan. 2007, pp. 404-417.
Krishnan et al., "Fluidization, resolidification, and reorientation of the endothelial cell in response to slow tidal stretches," American Journal of Physiology: Cell Physiology, vol. 303, 2012, pp. C368-C375.
Krishnan et al., "Reinforcement versus Fluidization in Cytoskeletal Mechanoresponsiveness," PLoS One, vol. 4, Issue 5, May 2009, 8 pages.
Lan et al., "Transient stretch induces cytoskeletal fluidization through the severing action of cofilin," American Journal of Physiology Lung Cellular and Molecular Physiology, vol. 314, 2018, pp. L799-L807.
Lee et al., "Physically-Induced Cytoskeleton Remodeling of Cells in Three-Dimensional Culture," PLOS ONE, vol. 7, Issue 12, Dec. 2012, 12 pages.
Mali et al., "Antitumor effectiveness of electrochemotherapy: A systematic review and meta-analysis," European Journal of Surgical Oncology (EJSO), vol. 39, Issue 1, Jan. 2013, pp. 4-16.
Maswiwat et al., "Effects of cell orientation and electric field frequency on the transmembrane potential induced in ellipsoidal cells," Bioelectrochemistry, vol. 74, 2008, pp. 130-141.
Mermelstein et al., "Changes in cell shape, cytoskeletal proteins and adhesion sites of cultured cells after extracellular Ca2+ chelation," Brazilian Journal of Medical and Biological Research, vol. 36, No. 8, 2003, pp. 1111-1116.
Meulenberg et al., "Differential Cellular Effects of Electroporation and Electrochemotherapy in Monolayers of Human Microvascular Endothelial Cells," PLOS ONE One, vol. 7, Issue 12, Dec. 2012, 9 pages.
Murovec et al., "Modeling of Transmembrane Potential in Realistic Multicellular Structures Before Electroporation," Biophysical Journal, vol. 111, Nov. 15, 2016, pp. 2286-2295.
Mussauer et al., "Resistivity of Red Blood Cells Against High-Intensity, Short-Duration Electric Field Pulses Induced by Chelating Agents," Journal of Membrane Biology, vol. 170, 1999, pp. 121-133.
Nain et al., "Polymeric nanofibers: isodiametric design space and methodology for depositing aligned nanofiber arrays in single and multiple layers," Polymer Journal, vol. 45, 2013, pp. 695-700.
Neamtu et al., "Pore resealing inactivation in electroporated erythrocyte membrane irradiated with electrons," Bioelectrochemistry and Bioenergetics, vol. 48, 1999, pp. 441-445.
Needham et al., "Electro-mechanical permeabilization of lipid vesicles. Role of membrane tension and compressibility," Biophysical Journal, vol. 55, May 1989, pp. 1001-1009.
Nekouzadeh et al., "Stretch-activated force shedding, force recovery, and cytoskeletal remodeling in contractile fibroblasts," Journal of Biomechanics, vol. 41, 2008, pp. 2964-2971.

(56) References Cited

OTHER PUBLICATIONS

Nesin et al., "Manipulation of cell volume and membrane pore comparison following single cell permeabilization with 60-and 600-ns electric pulses," Biochimica et Biophysica Acta, vol. 1808, 2011, pp. 792-801.
Padhi et al., "Bioenergetics underlying single cell migration on aligned nanofiber scaffolds," American Journal of Physiology—Cell Physiology, vol. 318, 2020, pp. C476-C485.
Pakhomov et al., "Disassembly of actin structures by nanosecond pulsed electric field is a downstream effect of cell swelling," Bioelectrochemistry, vol. 100, Dec. 2014: 88-95, 8 pages.
Pavlin et al., "Theoretical and experimental analysis of conductivity, ion diffusion and molecular transport during cell electroporation—relation between short-lived and long-lived pores," Bioelectrochemistry, vol. 74, 2008, pp. 38-46.
Pehlivanova et al., "Multiple effects of electroporation on the adhesive behaviour of breast cancer cells and fibroblasts," Cancer Cell International, vol. 12, No. 9, 2012, 14 pages.
Perrier et al., "Response of an actin network in vesicles under electric pulses," Scientific Reports, vol. 9:8151, 2019, 11 pages.
Platonova et al., "Role of cytoskeleton network in anisosmotic volume changes of intact and permeabilized A549 cells," Biochimica et Biophysica Acta, vol. 1848, 2015, pp. 2337-2343.
Potter et al., "Transfection by Electroporation," Current Protocols in Molecular Biology, Chp. 9, Unit 9.3, May 2003, 12 pages.
Pucihar et al., "A Time-Dependent Numerical Model of Transmembrane Voltage Inducement and Electroporation of Irregularly Shaped Cells," IEEE Transactions on Biomedical Engineering, vol. 56, No. 5, May 2009, pp. 1491-1501.
Pucihar et al., "Numerical Determination of Transmembrane Voltage Induced on Irregularly Shaped Cells," Annals of Biomedical Engineering, vol. 34, No. 4, Apr. 2006, pp. 642-652.
Rems et al., "Cell electrofusion using nanosecond electric pulses," Scientific Report, vol. 3, No. 3382, 2013, 10 pages.
Rols et al., "Electropermeabilization of mammalian cells. Quantitative analysis of the phenomenon," Biophysical Journal, vol. 58, Nov. 1990, pp. 1089-1098.
Rols et al., "Experimental evidence for the involvement of the cytoskeleton in mammalian cell electropermeabilization," Biochimica et Biophysica Acta, vol. 1111, 1992, pp. 45-50.
Sano et al., "In-vitro bipolar nano-and microsecond electro-pulse bursts for irreversible electroporation therapies," Bioelectrochemistry, vol. 100, 2014, pp. 69-79.
Saulis et al., "Kinetics of pore resealing in cell membranes after electroporation," Journal of Electroanalytical Chemistry and Interfacial Electrochemistry, vol. 321, 1991, pp. 1-13.
Saulis, G., "Pore Disappearance in a Cell After Electroporation: Theoretical Simulation and Comparison with Experiments," Biophysical journal, vol. 73, Sep. 1997, pp. 1299-1309.
Schaub et al., "Comparative Maps of Motion and Assembly of Filamentous Actin and Myosin II in Migrating Cells," Molecular Biology of the Cell, vol. 18, Oct. 2007, pp. 3723-3732.
Scheffer et al., "Irreversible Electroporation for Nonthermal Tumor Ablation in the Clinical Setting: A Systematic Review of Safety and Efficacy," Journal of Vascular and Interventional Radiology, vol. 25, 2014, pp. 997-1011.
Sharma et al., "The mechanistic influence of aligned nanofibers on cell shape, migration and blebbing dynamics of glioma cells," Integrative Biology, vol. 5, 2013, pp. 1036-1044.
Sheets et al., "Nanonet Force Microscopy for Measuring Cell Forces," Biophysical Journal, vol. 111, Jul. 12, 2016, pp. 197-207.
Sheets et al., "Shape-dependent cell migration and focal adhesion organization on suspended and aligned nanofiber scaffolds," Acta Biomaterialia, vol. 9, 2013, pp. 7169-7177.
Sozer et al., "Asymmetric Patterns of Small Molecule Transport After Nanosecond and Microsecond Electropermeabilization," The Journal of Membrane Biology, vol. 251, 2018, pp. 197-210.
Stacey et al., "Nanosecond pulsed electric field induced cytoskeleton, nuclear membrane and telomere damage adversely impact cell survival," Bioelectrochemistry, vol. 82, 2011, pp. 131-134.
Steuer et al., "Elasticity and tumorigenic characteristics of cells in a monolayer after nanosecond pulsed electric field exposure," European Biophysics Journal, vol. 46, 2017, pp. 567-580.
Steuer et al., "Transient suppression of gap junctional intercellular communication after exposure to 100-nanosecond pulsed electric fields," Bioelectrochemistry, vol. 112, 2016, pp. 33-46.
Sweeney et al., "Characterization of Cell Membrane Permeability In Vitro Part II: Computational Model of Electroporation-Mediated Membrane Transport," Technology in Cancer Research & Treatment, vol. 17, 2018, pp. 1-13.
Sweeney et al., "Quantification of cell membrane permeability induced by monopolar and high-frequency bipolar bursts of electrical pulses," Biochimica et Biophysica Acta, vol. 1858, 2016, pp. 2689-2698.
Teissie et al., "An Experimental Evaluation of the Critical Potential Difference Inducing Cell Membrane Electropermeabilization," Biophysical Journal, vol. 65, Jul. 1993, pp. 409-413.
Teissie et al., "Manipulation of Cell Cytoskeleton Affects the Lifetime of Cell Membrane Electropermeabilization," Annals of the New York Academy of Sciences, vol. 720, 1994, pp. 98-110.
Teissie, J., "Membrane Permeabilization Lifetime in Experiments," In: Handbook of Electroporation, Springer Publishing, 2017, pp. 61-75.
Tekle et al., "Selective and asymmetric molecular transport across electroporated cell membranes," Proceedings of the National Academy of Sciences, vol. 91, Nov. 1994, pp. 11512-11516.
Thery et al., "Experimental and theoretical study of mitotic spindle orientation," Nature, vol. 447, May 2007, pp. 493-497.
Thompson et al., "Disruption of the Actin Cortex Contributes to Susceptibility of Mammalian Cells to Nanosecond Pulsed Electric Fields," Bioelectromagnetics, vol. 35, 2014, pp. 262-272.
Thompson et al., "Role of Cytoskeleton and Elastic Moduli in Cellular Response to Nanosecond Pulsed Electric Fields," In: Terahertz and Ultrashort Electromagnetic Pulses for Biomedical Applications, SPIE, 2013, 9 pages.
Towhidi et al., "Variability of the Minimal Transmembrane Voltage Resulting in Detectable Membrane Electroporation," Electromagnetic Biology and Medicine, vol. 27, 2008, pp. 372-385.
Tsong, T. Y., "Electroporation of cell membranes," Biophysical Journal, vol. 60, Aug. 1991, pp. 297-306.
Tu-Sekine et al., "Inositol polyphosphate multikinase is a metformin target that regulates cell migration," The FASEB Journal, vol. 33, Dec. 2019, pp. 14137-14146.
Usaj et al., "Cell size dynamics and viability of cells exposed to hypotonic treatment and electroporation for electrofusion optimization," Radiology and Oncology, vol. 43, No. 2, 2009, pp. 108-119.
Wang et al., "Suspended Micro/Nanofiber Hierarchical Biological Scaffolds Fabricated Using Non-Electrospinning STEP Technique," Langmuir, vol. 30, 2014, pp. 13641-13649.
Weaver et al., "Pore lifetimes in cell electroporation: Complex dark pores?" arXiv:1708.07478, 2017, 6 pages.
Weaver et al., "Theory of electroporation: A review," Bioelectrochemistry and Bioenergetics, vol. 41, 1996, pp. 135-160.
Xiao et al., "Effect of actin cytoskeleton disruption on electric pulse-induced apoptosis and electroporation in tumour cells," Cell Biology International, vol. 35, No. 2, 2011, pp. 99-104.
Yu et al., "Modeling Transport Across the Electroporated Membrane," In: Handbook of Electroporation, Springer International Publishing: 2017, pp. 1089-1110.

* cited by examiner

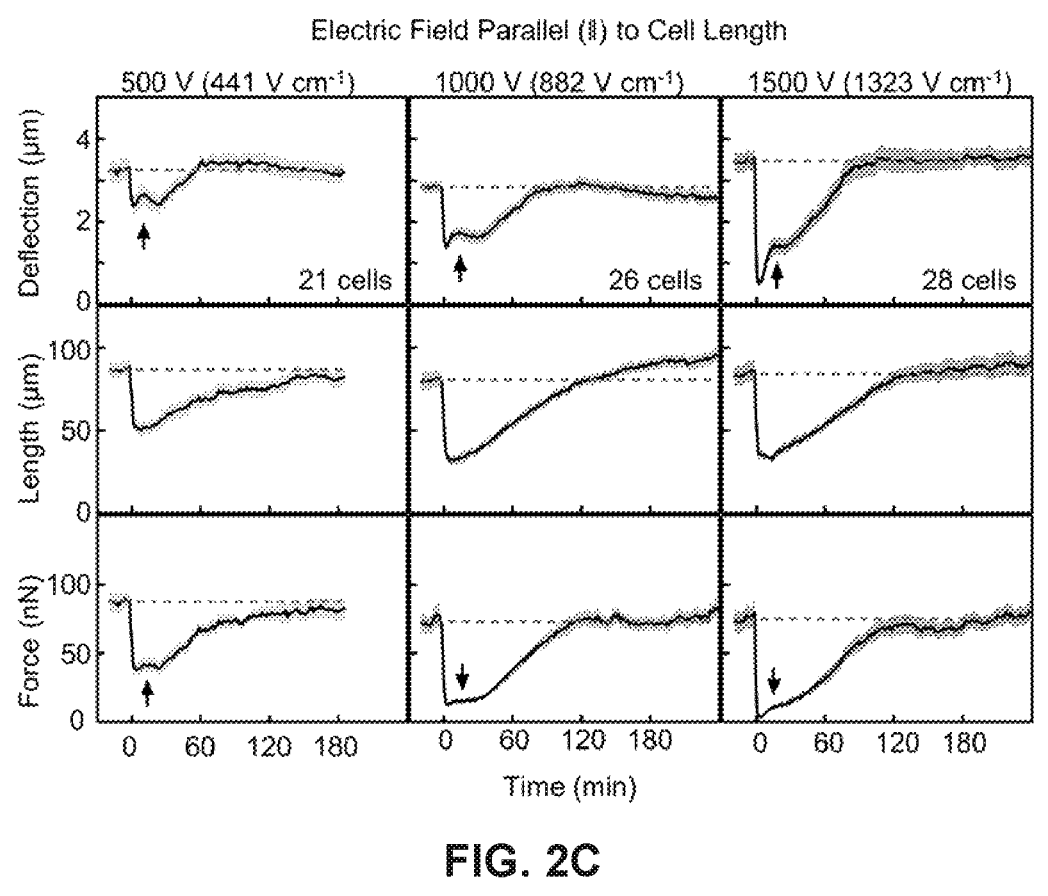

Electric Field Parallel (∥) to Cell Length

500 V (441 V cm⁻¹) 1000 V (882 V cm⁻¹) 1500 V (1323 V cm⁻¹)

Deflection (μm) 21 cells 26 cells 28 cells

Length (μm)

Force (nN)

Time (min)

FIG. 2C

Cell volume= Σ[(*Cell projected area in each slice*)x(*z-slice thickness*)]

METHOD FOR INTRACELLULAR DELIVERY OF COMPOUNDS USING CELL FORCE AND SHAPE WITH ELECTRIC FIELDS

CROSS REFERENCE TO RELATED APPLICATIONS

This application is a U.S. national phase application under 35 U.S.C. 371 of International Patent Application No. PCT/US2020/048625, filed Aug. 28, 2020, which claims priority upon U.S. Provisional Application No. 62/894,314, filed on Aug. 30, 2019, both of which are incorporated herein by reference in their entirety.

BACKGROUND

Electroporation is an electrical technique used for disrupting the lipid bilayer of cells via exposure to high electric fields and is useful for a variety of purposes including gene transection, electrofusion, electrochemotherapy, and tumor ablation. Electric fields destabilize the lipid bilayer and increase the membrane permeability by creating hydrophilic pores. Electroporation is reversible if the cell membrane is transiently permeabilized and the pores reseal over time leading to a return of homeostasis. Electroporation becomes irreversible if the magnitude of disruption exceeds the cells ability to regain membrane integrity and results in cell death. Gene transfection, electrofusion, and electrochemotherapy rely on the reversible effects of electroporation. Tumor ablation, however, exploits irreversible electroporation to create nonthermal ablation that preserve vascular and tissue structures.

Cellular recovery after electroporation has been primarily monitored by membrane permeability markers, most notably membrane-impermeant fluorescent stains (propidium iodide, cyanine nucleic acid stains, etc.) and brightfield dyes (trypan blue). However, membrane integrity is only one necessary condition for cell homeostasis, but does not indicate that homeostasis has been achieved. In fact, cells often must reestablish cell ionic gradients, excrete excess water, repolymerize cytoskeletal components, and rebuild ATP concentrations after electroporation before the cells has completely returned to a pre-treatment state. For this reason, it is sensible to look for an alternative metric for cellular recovery that provides a provides a more holistic metric of cell homeostasis, for example, by examining the relationship between electroporation and mechanical response in a controlled microenvironment.

Several studies suggest that the cytoskeleton is disrupted directly or indirectly by electroporation. Contractile forces are generated within cells by filamentous actin that anchor to the extracellular matrix by focal adhesions. Actin also interacts with the cell membrane to provide structural support for the lipid membrane. Actin interactions with the membrane have been hypothesized to impact the resealing time of pores. A mechanical analysis of the cell, for example via contractile forces, would therefore be an excellent means to investigate cytoskeletal effects and monitor cell recovery in a more holist manner. Mechanobiology has shown that cells exert quantifiable forces on the extracellular matrix that determine intracellular function, cell signaling, and cell behavior. Consequently, the contractile nature of cells may provide a new way to measure cell recovery after electroporation that is both dye-free and not reliant simply on membrane resealing.

The rapid emergence of genetic engineering in the past decade has been largely driven by ground-breaking gene editing techniques such as CRISPR/CAS9 and the zinc-finger nucleases platform. Gene transfection is poised to improve treatments for many diseases and disorders. It has become a standard laboratory task and is widely used by the research community for many purposes. Despite the current widespread use of genetic engineering and the anticipated growth of gene transfection applications, the efficiency almost all standard gene delivery methods is hindered by their shortcomings. Additionally, certain cell types such as pluripotent stem cells are recalcitrant to gene transfection and genetic engineering. Finding a method that could be used globally for effective delivery of genetic material to the cytoplasmic region remains a challenge.

Viral gene transfection is one of the most established transfection techniques; it involves loading a DNA vector into a genetically modified virus such as an adenovirus or retrovirus. Viral transfection is associated with high transfection efficiency and viability after transfection, and consequently is widely used for genetic engineering applications. However, viral transfection for clinical applications has significant drawbacks including immunogenicity and cytotoxicity. In fact, the first death in gene therapy was due to an immune reaction to the adenovirus used during therapy. Viral transfection is also associated with insertional mutagenesis, or ectopic integration of viral DNA that pose a significant concern for clinical applications. Furthermore, using viral vectors for transduction is limited to relatively small packaged genetic information.

Most non-viral transfection techniques that have been developed suffer from low transfection efficiencies, low expression levels, and/or involve other disadvantages such as complex procedures or safety concerns, with polymeric and lipid-based nanoparticles such as Lipofectamine 2000 and PEI being among the most popular non-viral delivery techniques. In addition, many physical delivery techniques that disrupt the cell membrane and enable transfection have been developed, including microinjection, photoporation, hydroporation, sonoporation, and electroporation. Most physical delivery methods are associated with high transfection efficiency but such techniques are also typically associated with low cell viability. Microinjection involves the direct injection of DNA into the cytoplasm or nucleus of a single cell and can yield efficiencies up to 100%. However, the technique is often not practical for transfection of large cell populations as it is a laborious process.

Transfection by electroporation is poised to become one of the most common techniques for delivery of Cas9-sgRNA ribonucleoprotein (RNP) complexes due to its acceptable efficiency and safety in vitro and in vivo. The abundant advantages of electroporation make this technique very attractive: it is technically simple; it can be used to treat a whole population of cells; it has a broad application for the transfer of any macromolecule; it provides greater efficiency of transfection for some cell lines; and it can be applied equally successfully to prokaryotic and eukaryotic cells without major modifications and adaptation to cell type and origin. The downside of classical bulk electroporation transfection is low transfection efficiency and low viability. Gene electrotransfer protocols typically prescribe 8 electrical pulses of ~200-700 V/cm that are in the order of microseconds. After pore formation, DNA molecules are thought to enter the cells due to electrophoretic forces. A transfection efficiency of between 40-89% has been reported based on the genetic material delivered as well as cell type. Conventional transfection by electroporation is performed on a cell suspension in a cuvette or well-plate-based system that is linked to a pulse generator. The major limitation of the electroporation method is that the transfection efficiency is very low.

Transfection of rare cell populations (such as primary pluripotent stem cells) requires both high transfection efficiency and high viability—an outcome that is not possible with current electro-transfection protocols. High electric fields lead to more successful transfection but also reduced cell viability; a problem that is exacerbated with use of primary cells from patients that are typically obtained in low numbers. Furthermore, many rare cell populations such as primary cells have limited replication potential, necessitating high efficiency. Optimization of pulsing parameters and electroporation buffer have yielded some increases in efficiency, yet low efficiency remains a central limitation of electroporation transfection. It would be desirable to develop a method for understanding contractile forces in cells, including the relationship between the cells and the extracellular environment, as a means to develop more efficient and more targeted electroporation techniques. The method would ideally be useful globally for effective delivery of genetic material to the cytoplasmic region and/or nucleus while avoiding the immunogenic and other drawbacks of methods such as viral transduction and would simultaneously applicable to large populations of cells. Furthermore, despite advances in electroporation research, there is still a scarcity of efficient methods that result in large populations of transfected, viable cells; that are capable of controlling the number, density, and colocalization of genes within cells; that synchronize cell mechanical response with gene delivery; and that allows various media perturbations to enhance cell viability and gene delivery. These needs and other needs are satisfied by the present disclosure.

SUMMARY

In accordance with the purpose(s) of the present disclosure, as embodied and broadly described herein, the disclosure, in one aspect, relates to methods for modifying cells such as, for example, changing shape, cell force, and/or modifying structural integrity of the cells. In a further aspect, the disclosure relates to controlling membrane permeability in cells by applying an electric current, where the cells are in contact with a polymeric nanofiber array and wherein direction and voltage of the electric current can be modified to induce the desired cellular response. In some aspects, the method results in higher survivability for cells during electroporation, greater permeability to molecules and/or drugs of different sizes, and greater transfection efficiencies for rare primary cells.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A shows a microfluidic PDMS device on a glass cover slide 102 encloses a nanofiber network 104 (with polystyrene nanofibers 106 enlarged in inset image) spun on a hollow substrate. The cells are electroporated via a high-voltage pulse generator 100 connected to two needle electrodes. Precisely controlled nanofiber networks are fabricated using the STEP technique: ø250 nm fibers (15 μm spacing) are deposited orthogonal to ø2 μm fibers (275 μm spacing) and fused at their intersections. Scale bar 20 μm (lower), and 1 μm (upper). FIG. 1B shows a parallel orientation, cell long-axis aligned with the electric field; Perpendicular orientation, cell long-axis perpendicular to the electric field. FIG. 1C shows single cells attach to parallel nanofibers, causing visible fiber deflection. Scale bar 25 μm. The deflecting fiber is modeled as a fixed-fixed beam with two point-loads, F, located at the attachment points of the cells and at an angle $\alpha_{Force}$. FIG. 1D shows finite element model indicates that the electric field is approximately uniform within the region of interest at the center of the scaffold. FIG. 1E shows an elongated cell shows f-actin stress fibers (red) and focal adhesions (green) along the fibers. Contractile force is applied along the f-actin stress fibers (bottom left), retraction fibers (bottom center), or at the bisection of the membrane angle (bottom right). The dashed lines indicate fiber location. Scale bars 10 μm (top) and 5 μm (bottom). FIG. 1F shows the angle $\alpha_{Force}$ is well approximated by a two-segment line when plotted against cell length. For cells longer than 63.4 μm, $\alpha_{Force}$ is constant at 12.4°. For cells shorter than 63.4 μm, $\alpha_{Force}$ is approximated as a linear function of cell length. Inset images show a round and elongated cell with corresponding data points. Scale bars 5 μm. EP, electroporation.

FIGS. 2A-2G show cell shape and contractile force response to electroporation. FIGS. 2A-2B shows cell responses to electroporation at 500 V, 1000 V, 1500 V in the (FIG. 2A) parallel orientation (441 V $cm^{-1}$, 882 V $cm^{-1}$, and 1323 V $cm^{-1}$ respectively) and (FIG. 2B) perpendicular orientation (455 V $cm^{-1}$, 911 V $cm^{-1}$, and 1366 V $cm^{-1}$ respectively). The onset of membrane disruption by electroporation is visualized for 1000 V ∥ by the inclusion of YO-PRO-1 (green, background subtraction and thresholding used to remove background signal). Cells show rounding, membrane blebbing, and an eventual return to a characteristic elongated state in a voltage- and orientation-dependent manner. Scale bars are 25 μm. FIGS. 2C-2D show average fiber deflection, cell length, and contractile force post-EP for cells in the parallel (FIG. 2C) and perpendicular orientation (FIG. 2D). Cells in the parallel orientation show rapidly decreased length and contractility, and recovery within 1-2 hours. For the perpendicular orientation, no response occurs at 500 V, a moderate response occurs at 1000 V, and an extreme response is seen at 1500 V. Unexpectedly, fiber deflection and force plots show a transitory increase shortly after electroporation (see arrows on plots) indicating multiple stages in the recovery process. Error bands show standard error. FIGS. 2E-2F show maximum percent decrease in force and cell length is greatest at high voltages. FIG. 2G shows electroporation at high electric fields causes significant cell death, particularly in the perpendicular orientation. Error bars in FIGS. 2E-2G show standard deviation.

FIG. 3A shows sample contractile force profile for a cell treated at 500V‖. The cell-rounding stage (Stage 1) begins after electroporation and ends at the first force minimum. Contractile forces increase during phase I of a biphasic stage (Stage 2) before decreasing again in phase II. The cell-spreading stage (Stage 3) begins after the second force minimum during which the cell recovers its pre-electroporation contractility. FIG. 3B shows images of a cell showing a multi-stage response (1000 V ‖). Corresponding force values are presented for each image and the stages of recovery are schematically represented above. Scale bar 25 μm. FIG. 3C shows contractile force and deflection for a representative cell from each treatment demonstrating a multi-stage response composed of a cell-rounding stage. Note a minimal response for 500 V ⊥. FIG. 3D shows cells in the perpendicular orientation have significantly less change in force and length in the first two minutes after electroporation, except at very high voltages (1500 V). FIG. 3E shows the biphasic stage lasts 20-30 minutes (longer for 1500 V ⊥) with higher voltages causing slightly longer durations. The duration of phase I is nearly equivalent to phase II. FIG. 3F shows force significantly increases during the biphasic response. The first and second minimum values are not significantly different. During the biphasic stage, cell length does not change significantly. FIG. 3G shows an image sequence of a representative cell electroporated (1000 V ‖) in calcium-free media. Scale bar 25 μm. Cell force and length remain unaffected in calcium-free DMEM during the first two minutes after electroporation (1000 V ‖).

FIG. 4A shows maximum intensity projections of cells stained for actin before electroporation and during various stages of recovery post-electroporation (1000 V ‖). FIG. 4B shows a single confocal z-slice taken in the nanofiber plane. Pre-EP, actin cytoskeleton consists primarily of well-defined stress fibers (yellow markers). During the cell-rounding stage (2, 8 min), both stress fibers and blebs (blue markers) are present. During the biphasic stage (8, 16 min), cells are rounded with cortical actin and no stress fibers. Eventually, stress fibers begin to reform (32 min) and blebbing is reduced as the cell enters the cell-spreading stage and regains its characteristic cytoskeletal structure. FIGS. 4C-4D show bleb size analysis. Large blebs form immediately after electroporation (maximum at 2 min) but are reduced to baseline values within 32 minutes. FIGS. 4E-4F show membrane roughness is quantified by the ratio of the contour length of the membrane along the nanofiber by the cell length end-to-end distance. Membrane roughness is at its maximum at 2 minutes after electroporation and returns to pre-EP values after 32 minutes. All scale bars 10 μm. EP, electroporation.

FIG. 5A demonstrates that cells show uptake of propidium iodide (PI) during and after the application of ten, 1000 V pulses (‖: 882 V $cm^{-1}$; ⊥: 911 V $cm^{-1}$) delivered at 1 Hz. Time t=0 indicates the end of the first pulse. PI uptake reveals distinct spatial distributions of membrane permeability for the parallel and perpendicular orientations. In the parallel orientation (a, left column), PI uptake is located near the cell attachment points. However, in the perpendicular orientation (a, right column), uptake is near the central sidewalls. White dashed lines show cell boundary pre-electroporation. The time series indicates that membrane permeability and the influx of PI precedes cell rounding. Scale bars 20 μm. FIG. 5B shows that representative intensity plots taken along the cell length (large white dashed lines) demonstrate the distinct spatial distributions of membrane permeability in the parallel and perpendicular orientations. FIG. 5C shows that PI uptake is biased toward the cathodic (depolarized) side of the cell. Error bands show standard error.

FIG. 6A shows brightfield images of cell responses to electroporation. FIG. 6B shows cell length and contractile force responses for five cell types after electroporation. Note that cell force is more dynamic than cell shape. All cell types demonstrate a robust loss and recovery of forces post-electroporation, but do not necessarily show significant changes in cell shape. FIG. 6C shows an example of a multi-stage response for each additional cell type.

FIG. 7A shows cells were treated with ten, 100 μs square wave pulses at 1 Hz. FIG. 7B shows actual voltage and current waveforms measured during the first pulse. Pulses approximate idealized square waves. FIG. 7C shows a finite element model shows the electric field distribution along the walls of the fluidic channel (FIGS. 7C, 7E) and in the plane of the nanofiber scaffold (FIGS. 7D, 7F). In FIGS. 7C-7D, the scaffold is modeled in the parallel orientation while FIGS. 7E-7F are modeled with the scaffold in the perpendicular orientation. The nanofiber region within the scaffold has an approximately uniform electric across the center of the scaffold. FIG. 7G shows that along the cutlines B-B and E-E the electric field magnitude is mostly constant, with asymptotic regions near the edges. FIG. 7H shows that along cutlines C-C and F-F, electric field is quite uniform. FIG. 7I shows that the voltage drop is nearly linear along cutlines B-B and E-E. The generated electric fields over the region of interest were approximately 440 V $cm^{-1}$, 882 V $cm^{-1}$, and 1323 V $cm^{-1}$ respectively across the scaffold region in the parallel orientation and 455 V $cm^{-1}$, 911 V $cm^{-1}$, and 1366 V $cm^{-1}$ respectively across the scaffold region in the perpendicular orientation.

FIGS. 8A-8B show data from FIGS. 2E-2F, represented to show significant differences due to electric field orientation. FIGS. 8C-8D show cells post-electroporation do not show significant differences in contractile force or length compared to pre-electroporation values. Post-electroporation data collected at 180 min for 500 V and 240 min for 1000 V and 1500 V. FIG. 8E shows that, for a given voltage and field orientation, high and low contractile cells show a similar force response in the first two minutes after EP. In the parallel orientation, the high contractile cells show a larger decrease in cell length immediately after electroporation when compared with low contractile cells, suggesting that contractility might increase the rate of rounding. However, high contractile cells also tend to also have longer initial lengths, so the rate of rounding may be dependent on both cell contractility and cell length. Stats not available for 1500 V ⊥ (n=1 for both bars). FIG. 8F shows response of control cells ('sham exposure') kept at the same culture conditions. In 2 hours cells demonstrated steady-state levels of contractility and maintained consistent cell shapes. EP, electroporation.

FIG. 9A shows a comparison of pre-electroporation forces for cells treated at 1500 V in the perpendicular orientation. The few cells that survived electroporation at 1500 V in the perpendicular orientation showed higher pre-electroporation forces than cells that did not survive electroporation FIG. 9B shows an example of cell death by accidental cell death. Very soon after electroporation, the cell takes on visual signs of cell death such as a loss of contrast and large membrane blebs. Additionally, the cell rapidly losses contractility as shown by the lack of fiber deflection after electroporation. Scale bar 25 μm. FIGS. 9C-9D show cell volume change during cell recovery. Volume was calculated in MATLAB using a z-stacks of fluorescent images (stained for actin, microtubules, and the nucleus) of fixed cells. The 2D area of the cell in each slice was used to estimate cell volume. FIG. 9D shows that cell volume seems to decrease after electroporation (1000 V ||), with the greatest decrease between 8 and 32 minutes after electroporation. However, cell volume is not statistically significant between timepoints. (n=6, 10, 8, 13, 7, 9 and 5 corresponding to pre-pulse, 0.5, 2, 8, 16, and 32-minute timepoints respectively) FIGS. 9E-9F show Joule heating due to the electric pulses results in a rapid increase in temperature that returns to near pre-electroporation levels within minutes. The maximum temperature increase within the device due to Joule heating was experimentally and analytically verified to be under 8° C. for all conditions. Experimental measurements of joule heating within the device was measured via a fiber optic temperature probe placed through the PDMS sidewall into the center of the electrode regions. FIG. 9F shows the maximum temperature occurs immediately after pulsing and then returns to near pre-electroporation levels within 5 minutes. Fiber optic data collected at room temperature.

FIG. 11A shows temporal dynamics of cell blebbing in Ca-free media (n=10 for each timepoint). The roughness ratio is defined in FIG. 4F. FIG. 11B shows a comparison of the blebbing dynamics during electroporation regular media versus Ca-free media. FIGS. 11C-11D show PI uptake after electroporation at 1000 V (parallel orientation) in (FIG. 11C) growth media (1.95 mM calcium, n=8) and (FIG. 11D) calcium-free DMEM (n=12). PI uptake dynamics were recorded every 5 seconds with a 20×0.8 NA objective. FIG. 11E shows a representative cell electroporated at 1000V || in growth media (1.95 mM Ca; DMEM+10% FBS+1% PS), DMEM (1.8 mM Ca), and Calcium-free DMEM (~0 mM Ca). Scale bar 25 μm.

Figure 1A:
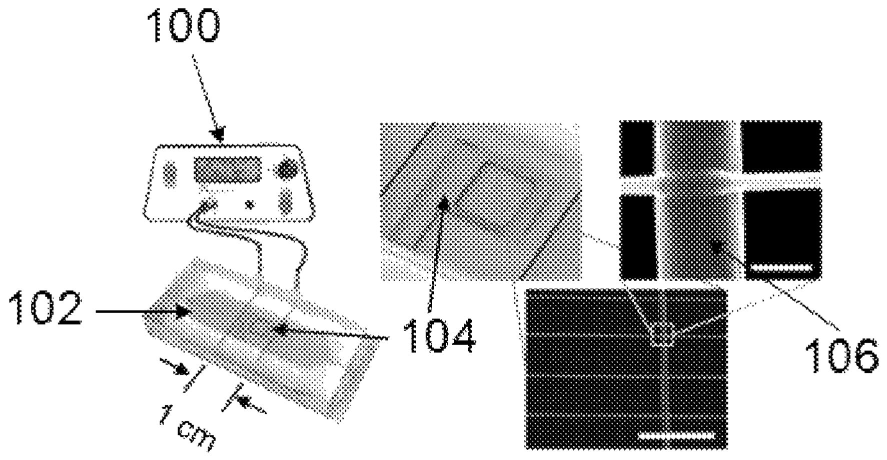
FIGS. 1A-F show nanofiber force sensing.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a cell," "a nanofiber," or "an electrode," includes, but is not limited to, mixtures or combinations of two or more such cells, nanofibers, or electrodes, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y°, and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a compound, such as, for example, a nucleic acid designated for cell uptake refers to an amount that is sufficient to achieve the desired improvement in the cell into which the compound is delivered, e.g. achieving the desired level of gene expression for exogenous nucleic acids. The specific level in terms of concentration in a composition required as an effective amount will depend upon a variety of factors including the number and type of cell, size of the compound, voltage of the applied electric field, and geometry of the nanofiber array.

As used herein, the terms "optional" or "optionally" means that the subsequently described event or circumstance can or cannot occur, and that the description includes instances where said event or circumstance occurs and instances where it does not.

A cell membrane separates the interiors of cells from the outside environment. A cell membrane under most circumstances is "selectively permeable" to ions and/or small organic molecules through processes such as, for example, diffusion including facilitated diffusion, as well a passive transport (e.g., through ion channels) and active transport (e.g., moving substances to areas of already higher concentration of the substances through the use of cellular energy). Some substances, meanwhile, are "membrane-impermeant," meaning that they do not typically cross cell membranes to enter cells. Membrane-impermeant substances can be large molecules including, but not limited to, pharmaceutical compositions, proteins, peptides, vectors, and nucleic acids including nucleic acids useful for gene therapy. In one aspect, "membrane disruption" by various means (e.g., presence of an electric field and/or current, chemical agents, mechanical stress, and the like) may allow substances that are typically membrane-impermeant to enter the cell.

"Electroporation" as used herein refers to application of an electrical field to cells to increase membrane permeability. In some aspects, electroporation is an efficient method for introduction of otherwise membrane-impermeant substances, such as, for example, foreign genes, into cells, including to the nucleus, the cytoplasm, or both. In other aspects, electroporation can be useful for tumor ablation. Other molecules that can be introduced into the cell include, but are not limited to, nucleic acids, a vector, a peptide or protein, a membrane-impermeant stain, a pharmaceutical compound, cryoprotectants, exogenous organelles, molecular probes, nanodevices, nanoparticles, and combinations thereof.

"Membrane potential" or "transmembrane potential" refers to the difference in electric potential between the inside of a cell and the extracellular environment. Membrane potential can vary depending on the extracellular environment including pH, solute identity, and solute concentration; type of cell; and the like. In one aspect, in the methods disclosed herein generate an "induced transmembrane potential" (ITP) in cells when an external electric field is applied to the cells. In some aspects, an ITP of sufficient magnitude can reversibly alter membrane permeability (e.g., induce "electropermeabilization").

The "cytoskeleton" is a network of protein filaments in the cytoplasm of all cells. The cytoskeleton is dynamic and functions to provide shape to cells as well as to provide resistance to deformation. Cytoskeletal connections between cells can stabilize tissues. In one aspect, "microfilaments" are components of the cytoskeleton made from the protein actin. In another aspect, "microtubules" are components of the cytoskeleton made from dimers of α- and β-tubulin. Both microfilaments and microtubules can undergo rearrangement in response to various stimuli including mechanical stress, presence of electric current, and the like. In one aspect, in the methods disclosed herein, application of an electric field can induce cytoskeletal rearrangement of microtubules or microfilaments. Meanwhile, actin can have multiple forms including "G-actin" (globular actin) and "F-actin" (filamentous actin). In one aspect, F-actin is composed of G-actin monomers and can build up higher order structures including, but not limited to, stress fibers and cell motility structures in motile cells.

"Focal adhesions" are sites where cytoskeletal components such as, for example, actin filaments, link to the extracellular matrix. In one aspect, focal adhesions can be large, multi-protein structures that form mechanical links. In another aspect, as used herein, focal adhesions can refer to sites where cells attach to polymeric nanofibers in the nanoarrays disclosed herein.

In one aspect, as used herein, "blebbing" refers to a bulge in the plasma membrane of a cell. In another aspect, blebbing can occur as a result of cytoskeletal rearrangement or contraction of cytoskeletal fibers. In some aspects, blebbing can be induced in the presence of an electric field. In other aspects, when the electric field is removed, blebbing reverses and the cell assumes its initial shape. In an alternative aspect, blebbing can occur during apoptosis as a dying cell's cytoskeleton begins to break up.

"Contractile force" as used herein refers to a force causing a change in cell shape. In one aspect, the contractile force can be an internal force such as one generated, for example, during cytoskeletal rearrangement or contraction of actin fibers. In another aspect, contractile force can be exogenous such as, for example, when the extracellular environment (e.g., extracellular matrix or nanofiber array to which the cell is attached) experiences movement or contraction. In a further aspect, contractile force with respect to cells is typically measured in nanonewtons (nN).

A "nanofiber" as used herein refers to a fiber such as, for example, a polymeric fiber, having a diameter of from about 100 nm to about 100 μm. In some aspects, the nanofibers disclosed herein are made from or include polystyrene or another extrudable polymer.

"Electrospinning" refers to a method of producing fibers wherein an electric force draws charged threads of polymer solutions or melts into fibers including nanofibers wherein diameter can be controlled based on electric current intensity, liquid flow rate, superficial tension of polymer solution, and dielectric permittivity of the polymer solution. In one aspect, the nanofibers disclosed herein are produced using a "non-electrospinning" method wherein control of fiber diameter can be tuned by altering polymeric solution concentration.

"Low conductivity" media as used herein refers to cell culture media with a conductivity value of from about 0.01 to about 0.2 S/m, or of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.2 S/m, or a combination of any of the foregoing values, or a range encompassing any of the foregoing values. In some aspects, low conductivity medium is useful in the methods disclosed herein.

"Joule heating" or "resistive heating" as used herein refers to a process by which passage of an electric current through a medium produces heat. In one aspect, joule heating in the methods disclosed herein is minimal and is not believed to affect operation of the devices disclosed herein. In another aspect, joule heating in the methods disclosed herein remains under 8° C. under all conditions tested herein. In one aspect, using a calcium-free or low-conductivity medium reduces the amount of heating that occurs during the methods disclosed herein.

"Engineered cells" as used herein refers to cells that have been manipulated to lose or gain functions and/or properties. Cells can be engineered or manipulated by any technique known in the art including, but not limited to, transformation; transfection; transduction; gene editing using transcription activator-like effector nucleases (TALEN), CRISPR/Cas, or another method; somatic fusion; somatic cell nuclear transfer; fusion of cells from two organisms using the Sendai virus or another virus; manipulation of the cellular environment through culture medium choice; manipulation of cell shape using the disclosed methods; and the like.

Unless otherwise specified, temperatures referred to herein are based on atmospheric pressure (i.e. one atmosphere).

Method for Modifying Cells

In one aspect, disclosed herein is a method for modifying a plurality of cells, the method including the step of applying an electric field to a nanofiber array comprising the plurality of cells, wherein the nanofiber array comprises a first array of first fibers and a second array of second fibers, wherein the first fibers are positioned at an angle of from about 0° to about 90° to the second fibers.

In a further aspect, "modifying" can include changing or controlling the shape of the cells, altering structural integrity of the cells (e.g., creating transient pores in the cell membrane), changing or controlling cell force, or any combination thereof. In another aspect, the cells can be mammalian cells such as, for example, glioblastoma cells and/or other brain cancer cells, liver cancer cells, breast cancer cells, cervical cancer cells, ovarian cancer cells, prostate cancer cells, skin cancer cells, mesothelioma cells, dendritic cells, hepatocytes, pancreatic islets, fibroblasts including cancer-associated fibroblasts, stem cells including totipotent, pluripotent, and/or multipotent stem cells, mouse myoblasts, smooth muscle cells, cardiomyocytes, Chinese hamster ovary cells, engineered cells, and any combination thereof.

In another aspect, the cell can be a non-mammalian vertebrate cell such as, for example, a bird cell, a reptile cell, an amphibian cell, a cartilaginous fish cell, or a bony fish cell. In an alternative aspect, the cell can be an invertebrate cell including, but not limited to, an arthropod cell (e.g., insect, spider, shrimp, crab, and the like), an annelid cell (e.g., earthworm, leech, and the like), an echinoderm cell (e.g., starfish, sea urchin, and the like), a mollusk cell (e.g., snail, octopus, squid, clam, and the like), a nematode cell, a flatworm cell, or a combination thereof.

In still another aspect, the cell can be a plant cell such as, for example, a grain crop plant, a fruit or vegetable crop plant, a plant used for animal feed, an ornamental plant, *Arabidopsis thaliana* or another common experimental plant, an invasive plant species, a woody plant, a fibrous plant (e.g., cotton, flax), or a combination thereof.

In another aspect, the cell can be a fungal cell such as, for example, a yeast cell (e.g., *Saccharomyces cerevisiae, Saccharomyces pombe*, another *Saccharomyces* species, or a *Candida* species), a mold cell, a mushroom cell, a symbiotic fungus, a mold cell, a pathogenic fungus, an ascomycete cell, or a combination thereof.

In yet another aspect, the cell can be a bacterial cell such as, for example, a common experimental organism (e.g., *Bacillus subtilis, Escherichia coli*), a pathogenic bacterium, a commercially useful bacterium, a probiotic bacterium, or a combination thereof.

In another aspect the cell can be an archaeal cell, a protozoal cell, or another common cell type.

Method for Constructinq a Scaffold

In another aspect, provided herein is a method for constructing a scaffold. In one aspect, the method includes at least the following steps:

a. providing a master mold;
b. casting a resin in the master mold;
c. curing the resin to form a cured resin;
d. removing the cured resin from the mold;
e. attaching the cured resin to a substrate; and
f. contacting the cured resin with at least two electrodes.

In some aspects, the resin can be a silicone or crosslinkable silicone such as, for example, polydimethylsiloxane (PDMS). In another aspect, the resin further contains a crosslinker. In one aspect, the resin and crosslinker can be present in a ratio of about 10:1 (wt/wt). In one aspect, crosslinking can be carried out by exposing the resin to a solvent, a solvent vapor, crosslinking, heating and/or melt-bonding, laser annealing, or exposure to electromagnetic radiation.

In another aspect, the resin can be cured at about 80° C. In another aspect, the resin can be cured for about 4 h.

In some aspects, the substrate can be glass. In another aspect, the cured resin can be attached to the substrate using a plasma cleaner.

In one aspect, the electrodes can be stainless steel, gold, platinum, a conductive epoxy, gold with a titanium adhesion layer, or any combination thereof. In another aspect, the electrodes can be placed on the scaffold at a distance of about 1 cm apart. In still another aspect, the electrodes can be placed from about 100 μm to about 1 cm apart, or about 100, 200, 300, 400, 500, 600, 700, 800, or about 900 μm apart, or a combination of any of the foregoing values, or a range encompassing any of the foregoing values. In one aspect, the electrodes can be placed at an angle of from about 0° to about 90° with respect to one another. In another aspect, the electrodes can be placed parallel to one another. In some aspects, multiple pairs of electrodes can be placed on the scaffold. Further in these aspects, different pairs of electrodes can be activated at different times in order to electroporate a subset of cells. In one aspect the electrodes can be fixed in place with an adhesive such as, for example, an epoxy. In another aspect, the electrodes are deposited using a lithography technique such as, for example, sputtering, deposition, or lift-off. In some aspects, the electrodes are passivated to mitigate electrochemical effects. In one aspect, the electrical field can be applied with pulses that are short or sinusoidal in order to penetrate the passivation layer.

Method for Constructinq a Nanofiber Array

In another aspect, provided herein is a method for constructing a nanofiber array on a scaffold. In a further aspect, the method can include at least the following steps:

a. mounting the scaffold on a motor and rotating the scaffold;
b. using a microneedle to extrude a first array of fibers;
c. turning the scaffold from 0° to an angle of from 1° to 90°;
d. using the microneedle to extrude a second array of fibers perpendicular to the first array of fibers; and
e. crosslinking the first array of fibers with the second array of fibers to form a nanofiber array.

In some aspects, the scaffold can be turned about 0, 5, 10, 15, 20, 25, 30, 35, 40, 45, 50, 55, 60, 65, 70, 75, 80, 85, or about 90°, or a combination of any of the foregoing values, or a range encompassing any of the foregoing values. In one aspect, the scaffold can be turned about 90°.

In one aspect, the first array of fibers, the second array of fibers, or both the first array of fibers and the second array of fibers are constructed from polystyrene or another extrudable polymer such as, for example, a polyester, a polyurethane, a polyacrylamide, a poly (methyl methacrylate), a polylactic acid, a poly(glycolic acid), a poly(lactic-co-glycolic acid), a polyaniline, a polypyrrole, a polyethylene oxide, fibrinogen, collagen, mixtures and/or copolymers thereof, carbon nanotubes, carbon black, metallic nanoparticles, or any combination thereof. In one aspect, the polymer can be dissolved in a solvent during extrusion. In some aspects, the solvent can be selected from p-xylene, n-octane, n-dodecane, cyclohexane, methylcyclohexane, benzene, toluene, o-xylene, ethyl benzene, p-diethyl benzene, chloromethane, methylene chloride, 1,1-dichloroethylene, ethylene dichloride, chloroform, 1,1-dichloroethane, trichloroethylene, carbon tetrachloride, chlorobenzene, o-dichlorobenzene, tetrahydrofuran, 1,4-dioxane, dibenzyl ether, acetone, methyl ethyl ketone, cyclohexanone, diethyl ketone, acetophenone, ethyl formate, ethyl acetate, nitrobenzene, pyridine, morpholine, N-methyl-2-pyrrolidone, N—N-dimethylformamide, dimethylsulfoxide, ethanol, allyl alcohol, 1-propanol, 2-propanol, 1-butanol, 2-butanol, benzyl alcohol, cyclohexanol, ethylene glycol monoethyl ether, diethylene glycol monomethyl ether, 1-decanol, benzoic acid, phenol, ethylene glycol, glycerol, propylene glycol, or some combination thereof.

In one aspect, the first array of fibers includes a plurality of first fibers having a diameter of from about 1 μm to about 100 μm, or of about 1, 5, 10, 15, 20, 25, 30, 35, 40, 45, 50, 55, 60, 65, 70, 75, 80, 85, 90, 95, or about 100 μm, or a combination of any of the foregoing values, or a range encompassing any of the foregoing values. In one aspect, the first fibers have a diameter of from about 2 μm to about 10 μm, or of about 2, 2.5, 3, 3.5, 4, 4.5, 5, 5.5, 6, 6.5, 7, 7.5, 8, 8.5, 9, 9.5, or about 10 μm, or a combination of any of the foregoing values, or a range encompassing any of the foregoing values. In another aspect, the first fibers are spaced from about 50 μm to about 1 mm apart, or from about 250 μm to about 350 μm apart, or about 50, 100, 150, 200, 250, 300, 350, 400, 450, 500, 550, 600, 650, 700, 750, 800, 850, 900, or about 950 μm apart, or about 1 mm apart, or a combination of any of the foregoing values, or a range encompassing any of the foregoing values.

In another aspect, the second array of fibers includes a plurality of second fibers having a diameter of from about 100 nm to about 2 μm, or of about 00, 150, 200, 250, 300, 350, 400, 450, 500, 550, 600, 650, 700, 750, 800, 850, 900, or about 950 nm, or about 1, 1.1, 1.2, 1.3, 1.4, 1.5, 1.6, 1.7, 1.8, 1.9, or about 2 μm, or a combination of any of the foregoing values, or a range encompassing any of the foregoing values. In one aspect, the second fibers have an average diameter of about 250 nm. In another aspect, the second fibers are spaced about 10 μm apart.

In another aspect, the fibers are non-polymeric. Non-polymeric fibers useful in the methods and structures described herein include any metallic nanofiber, such as gold nanowire, platinum nanofiber, $SiO_2$, carbon fibers, or any combination thereof.

According to one aspect, a nanofiber grid is pro-vided. In a further aspect, the nanofiber grid can be constructed from high aspect ratio fibers. Methods of preparing nanofiber grids having high aspect ratio fibers also are provided. In one non-limiting aspect, the scaffold includes high aspect ratio fibers that can find use as a biological scaffold. As used herein, the term "aspect ratio" refers to the ratio of the average length of fibers in a scaffold (L) and the average diameter of the fibers within the scaffold (D). The term "high aspect ratio" refers to an aspect ratio of LID to be more than 200. In one aspect, fibers with an average diameter of 500 nm would have an average length more than 100 μm. In another non-limiting aspect, fibers with an average diameter on the nanometer scale should have an average length on the millimeter scale.

As used herein, "nanofiber grid" or "nanofiber array" refers to a matrix of high aspect ratio fibers. The matrix can be of any useful geometry and orientation. In one aspect, the matrix can include nanofibers, a single layer of fibers, or multiple layers of fibers. In a further non-limiting aspect, the matrix includes fibers that are oriented generally parallel to one another. In another non-limiting aspect, the matrix comprises fibers that are oriented perpendicular to one another.

In certain aspects, the support fibers can be thicker than the cross fibers, for example in the range of from 1 μm to 100 μm in thickness, and when used, in some aspects, they act as anchors for the cross-fibers fused thereto. In another aspect, the cross fibers are of a thickness and composition such that under a typical force of a cell, or forces generated by the methods disclosed herein, the fiber is displaced a distance sufficient to permit calculation of the forces acting on the fiber. In one aspect, a cross-fiber deflects at least 2 μm and no more than 5% of its segment length between adjacent intersections with an applied force of 50 nano Newtons at a higher structural stiffness and 10 nano Newtons at a lower structural stiffness. In one aspect, polymer solutions mixed with fluorescent dyes form fibers with fluorescent dyes. In such a case, deflections of 20 nm, and possibly lower, can be detected. In a further aspect, fiber deflection of 100 nm corresponds to forces in the tens of pico Newton range ($10^{-12}$).

By "fused", in the context of crossed fibers of the nanofiber grid described herein, it is meant structurally connected, for example by melt-bonding or solvent bonding of crossed fibers of the nano fiber grid. A "grid" or "array," in the context of the nanofiber grid, refers to a crossed pattern on non-intersecting fibers, specifically the support or first fibers and the cross-fibers or second fibers as described herein. In one aspect, collectively, the support fibers are preferably parallel, meaning they do not cross in at least one portion of the nanofiber grid, and not necessarily meaning that that the fibers are perfectly geometrically parallel over their entire length. Likewise, in another aspect, the cross-fibers are preferably parallel, meaning they do not cross in the same portion of the nanofiber grid, and not meaning in all instances that that the fibers are perfectly geometrically parallel over their entire length. In one aspect, the support fibers can be perpendicular to the cross-fibers, meaning that the support fibers form a 90° angle or approximately 90° angle with the cross-fibers, but can form an angle of from 10° to 90°, or 45° to 90° with respect to the cross-fibers, including increments there between, including 10°, 20°, 25°, 30°, 40°, 45°, 50°, 60°, 70°, 75°, 80°, 85° and 90°, or a combination of any of the foregoing values, or a range encompassing any of the foregoing values.

In one aspect, the high aspect ratio fibers of the nano fiber grid can be prepared from any suitable high aspect ratio fibers, such as from metals, carbon fibers, inorganic materials or polymers. To facilitate visualization of certain fibers, for example with polymeric fibers, in some aspects, a label may be added to the polymer. In a further aspect, a label can be mixed with a polymer solution prior to preparation of the fibers, or it can be coated onto or otherwise adhered to the fiber. Non-limiting examples of labels include dyes, fluorescent dyes, and quantum dots. Other nanoparticles, such as radiopaque materials or carbon particles can be added to the fiber. In one aspect, a labeling composition can be integrated into the polymer, for example by mixing a fluorescent dye, quantum dot or nanoparticle into a polymer solution prior to preparing the fibers of the nanofiber grid, or by coating the composition onto the fiber, optionally with a cell adhesion-promoting composition, for example by applying the composition to the fibers after they are formed. In any of these aspects, a label facilitates accurate visualization and measurement of fiber location and displacement.

Method for Contacting a Nanofiber Array with Cells

In one aspect, contacting the nanofiber array with cells includes placing a droplet of solution containing the cells on the nanofiber array. In some aspects, the solution contains about 100,000 cells/mL, or from about 50,000 cells/mL to about 150,000 cells/mL, or about 50,000, 60,000, 70,000, 80,000, 90,000, 100,000, 110,000, 120,000, 130,000, 140,000, or about 150,000 cells/mL, or a combination of any of the foregoing values, or a range encompassing any of the foregoing values. In another aspect, the droplet is about 35 μL.

In some aspects, following contacting the nanofiber array with cells, the solution of cells and the nanofiber array can be incubated for about 4 h, or from about 1 h to about 48 h, or about 1, 2, 3, 4, 5, 6, 7, 8, 10, 12, 16, 20, 24, 28, 32, 36, 40, or about 48 h, or a combination of any of the foregoing values, or a range encompassing any of the foregoing values.

In some aspects, the cells have a major axis and a minor axis that intersects the major axis. In some aspects, the major axis extends along the longest part of the cell. In one aspect, the major axis extends through the center of the cell. In another aspect, the minor axis can be perpendicular to the major axis or can be at an angle of from about 1° to about 90° with respect to the major axis.

In one aspect, the major axis is longer than the minor axis. In one aspect, when the cells contact the nanofiber array, the cells orient in the nanofiber array such that the cells lie between the second fibers and the major axis of the cells is parallel to the second fibers. Further in this aspect, the minor axis of the cells can be at an angle of from about 0° to about 90° to the second fibers, or can be perpendicular to the second fibers. In other aspects, the cells can have a spindle shape, a polygonal shape, an elongated shape, or any combination thereof.

In an alternative aspect, the major axis and the minor axis are about the same length or are of similar lengths. In one aspect, when the cells contact the nanofiber array, the cells orient in the nanofiber array such that the cells lie between the second fibers and the major axis of the cells is parallel to the second fibers. Further in this aspect, the minor axis of the cells can be at an angle of from about 0° to about 90° to the second fibers, or can be perpendicular to the second fibers. Further in this aspect, the cells can have a kite or diamond shape, a square shape, a rounded shape, or any combination thereof.

In another aspect, the cells in any shape can grow as a monolayer, in spheroids contacting the scaffold, or any combination thereof.

In one aspect, the methods employ multiple cell types or cultures deposited on a single nanofiber grid. In another aspect, the methods employ a device having two or more discrete cell cultures at independently addressable physical locations, such as in a microfluidic device, an array or multi-well dishes, for example as are known in the art and are commercially available. In a multiwall device, in one aspect, cells are cultured on one or more nanofiber grids in a cell culture device with two or more wells, each well independently including a nanofiber grid. In some aspects, where the device is a microfluidic device, the microfiber grid can be placed inside the microfluidic device, which contains cells along with media and/or hydrogel. In a further aspect, the microfluidic device itself can be any useful configuration and in one aspect is constructed from biocompatible polymers that are liquid impermeable such as polydimethylsiloxane (PDMS) or liquid permeable hydrogels such as polyethylene glycol diacrylate (PEG-DA).

In another aspect, cells that are amenable to analysis by the methods include prokaryotic cells, eukaryotic cells, animal cells, fungal cells, plant cells, bacterial cells, protozoa cells, archaea cells, vertebrate cells, invertebrate cells, mammalian cells and human cells including cell lines, chimera, and genetically modified (e.g., recombinant) versions of any of these cell types. In one aspect, cells useful in the methods described herein are eukaryotic and in many aspects, mammalian, for example human, and can be a cell line, a primary cell culture, or a specimen, such as a biopsy obtained, for example, from a tumor or a suspected tumor. In a further aspect, non-limiting examples of mammalian, for example human cells include myocytes, hepatocytes, neurons, cell precursors, such as cardiac stem cells, myoblasts, neuronal stem cells, mesenchymal stem cells, cancer cells, and recombinantly-modified cells.

In one non-limiting aspect, the nanofiber grid can be treated with (e.g., coated with, or otherwise combined with) a cell adhesion-promoting composition, to provide a biocompatible surface. In a further aspect, the scaffold can be treated to provide a sterilized surface for proteins and/or cells. In a further aspect, non-limiting examples of sterilization treatments include, but are not limited to: exposure to ultraviolet light; autoclave; exposure to high heat; irradiation, such as gamma irradiation; exposure to aseptic solvents, such as ethanol; exposure to plasma; and combinations thereof. In another non-limiting example, the scaffold can be treated with an agent to provide for a biocompatible and/or cytocompatible surface. Non-limiting examples of agents include: proteins, such as collagen, vitronectin, laminin, fibronectin, fibrinogen, gelatin, and alginate; polymers, such as poly(ethylene glycol), poly (lysine), poly(omithine); cell adhesion peptides; and growth factors, such as one or more of: basic fibroblast growth factor (bFGF), acidic fibro-blast growth factor (aFGF), vascular endothelial growth fac-tor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis fac-tor (TAF), corticotrophin releasing factor (CRF), transform-ing growth factors α and β (TGF-α and TGF-β), interleukin-8 (IL-8), granulocyte-macrophage colony stimulating factor (GM-CSF), interleukins, and interferons.

Cell Culture

According to certain aspects of the methods described herein, cells can be placed onto a nanofiber grid, in a suitable aqueous medium or hydrogel medium suitable for conducting the methods. In one aspect, an aqueous medium suitable for the methods described herein can be isotonic, hypertonic or hypotonic. In a further aspect, the aqueous medium can be a water-containing liquid composition including suitable ingredients for conducting the methods. Further in this aspect, suitable ingredients can include, but are not limited to, salts, sugars, amino acids, nutrients, buffers, vitamins, antibiotics, cellular extracts, rheology modifiers and/or animal serum, which can be used to maintain a cell, and for purposes herein can be any suitable composition, including normal saline, phosphate-buffered saline (PBS), cell culture medium (e.g., serum-containing or serum-free medium), etc., so long as cells can be deposited onto the nanofiber grid for purposes described herein and is consistent with the particular assay being conducted. As used herein, a "hydrogel" is a water-swellable polymeric composition, and can be any composition, natural or synthetic, that does not interfere with the methods described herein. In one aspect, in use, a nanofiber grid as described herein can be used in any suitable vessel, such as a cell culture vessel, including plastic or glass vessels, such as flasks, plated, bottles, multi-well cell culture dishes, or any suitable container for culturing cells or tissue.

According to one aspect of the methods described herein, cells can be grown on the nanofiber grid. As used herein, "growing cells" refers to maintaining cells in culture, including but not limited to adhesion, proliferation, migration, dif-ferentiation, and/or aggregation of cells.

In one aspect, cells can be grown in culture media appropriate for growth and differentiation of any given cell type. In some aspects, growth factors and cytokines, as are known in the art, can be used to induce cellular growth and differentiation. In a further aspect, the choice of cells to propagate on the nanofiber grid depends on the intended use.

In one aspect, the cells can be grown in a low-conductivity medium as described herein. An exemplary low-conductivity medium can be or include a potassium phosphate electroporation buffer (e.g., 10 mM $KH_2PO_4/K_2HPO_4$ in a ratio of 40.5:9.5 with 1 mM $MgCl_2$ and 250 mM sucrose and a pH of 7.2) or DEP buffer (8.5% sucrose [w/v], 0.3% glucose [w/v], and 0.725% RPMI medium [v/v]); however, other low-conductivity media known in the art can also be used in the disclosed methods.

In another aspect, the medium can be a calcium-free medium. In one aspect, a calcium free medium contains no or substantially no measurable calcium. Without wishing to be bound by theory, when pulses of applied voltage are short (e.g., less than about 10 μs), the cell death mechanism can change. Further in this aspect, the cell death mechanism may become calcium-dependent under these circumstances. In one aspect, then, growing the cells in calcium-free media increases the viability of the cells during the performance of the disclosed methods.

In still another aspect, the medium can contain components that alter properties of the cytoskeleton (e.g. actin, myosin, microtubules, and the like), the nucleus, and/or other properties of the cell. In one aspect, the compound that alters properties of actin can be selected from a cytochalasin, latrunculin, jasplakinolide, or a combination thereof. In another aspect, the compound that affects properties of microtubules can be selected from colchicine, demecolcine, nocodazole, paclitaxel, vinblastine, or a combination thereof. In still another aspect, the compound that affects properties of myosin can be selected from blebbistatin, W-7 hydrochloride, or a combination thereof. In one aspect, the compound that affects cellular properties can be selected from a RhoGTPase inhibitor such as, for example, rho inhibitor I, CCG-1423, NSC 23766, ML 141, CPYPP, or a combination thereof. In still another aspect, the compound that affects cellular properties can be selected from LY294002 or another PI3K inhibitor, PF573,228, PF431,396, or another focal adhesion kinase inhibitor, or a combination thereof. In a further aspect, the medium can contain rho-associated protein kinase inhibitors (ROCK inhibitors), including, but not limited to, fasudil, ripasudil, netarsudil, RKI-1447, Y-27632, GSK429286A, Y-30141, or another ROCK inhibitor. In any of these aspects, properties and components of the medium, scaffold, cell growth form (e.g., spheroid, monolayer, individual cells), and the like can be used to change cell form, function, and/or shape prior to and/or during performance of the disclosed method. In some aspects, the changes may cause a loss of cellular function, a gain of cellular function, or a combination of losses in some functions and gains in other functions.

Application of Electric Field

In one aspect, the electric field can be applied in a parallel direction with respect to the major axis of the cells. In another aspect, the electric field can be applied in a perpendicular direction with the major axis of the cells. In still another aspect, the electric field can be applied at any angle from 0° to 90° with respect to the major axis of the cells such as, for example, 0, 5, 10, 15, 20, 25, 30, 35, 40, 45, 50, 55, 60, 65, 70, 75, 80, 85, or about 90°, or a combination of any of the foregoing values, or a range encompassing any of the foregoing values.

In one aspect, the electric field can have an applied voltage of from about 500 V to about 30,000 V/cm, or of about 500, 600, 700, 800, 900, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or about 30,000 V, or a combination of any of the foregoing values, or a range encompassing any of the foregoing values. In one aspect, when the cell is a mammalian cell, the applied voltage can be from about 500 V to about 3000 V. In another aspect, when the cell is a bacterial cell, the applied voltage can be up to about 30,000 V.

In one aspect, the electric field is applied as from 1 pulse to 10 pulses, or as 1, 2, 3, 4, 5, 6, 7, 8, 9, or 10 pulses, or a combination of any of the foregoing values, or a range encompassing any of the foregoing values. In another aspect, the electric field can be applied as from 1 pulse to 100 pulses, or as 1, 10, 15, 20, 25, 30, 35, 40, 45, 50, 55, 60, 65, 70, 75, 80, 85, 90, 95, or 100 pulses, or a combination of any of the foregoing values, or a range encompassing any of the foregoing values. In another aspect, each pulse is from about 500 ns to about 100 ms, or is about 500 ns, 1 μs, 25, 50, 100, 150, 200, 250, 300, 350, 400, 450, 500, 550, 600, 650, 700, 750, 800, 850, 900, or 950 μs, or about 1, 25, 50, 75, or 100 ms, or a combination of any of the foregoing values, or a range encompassing any of the foregoing values.

In another aspect, the electric field can be applied as a square waveform, triangle waveform, trapezoidal waveform, bipolar pulse, sinusoidal pulse, a continuous electric field, or any combination thereof.

Figure 1B:
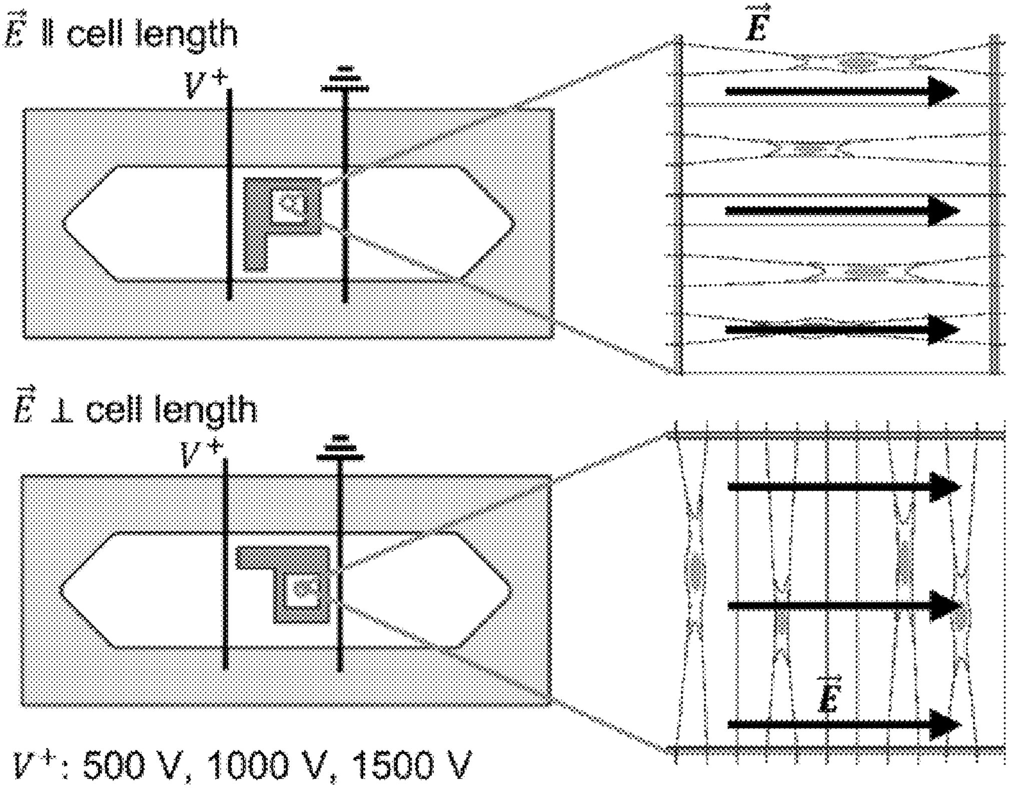
Figure 1C:
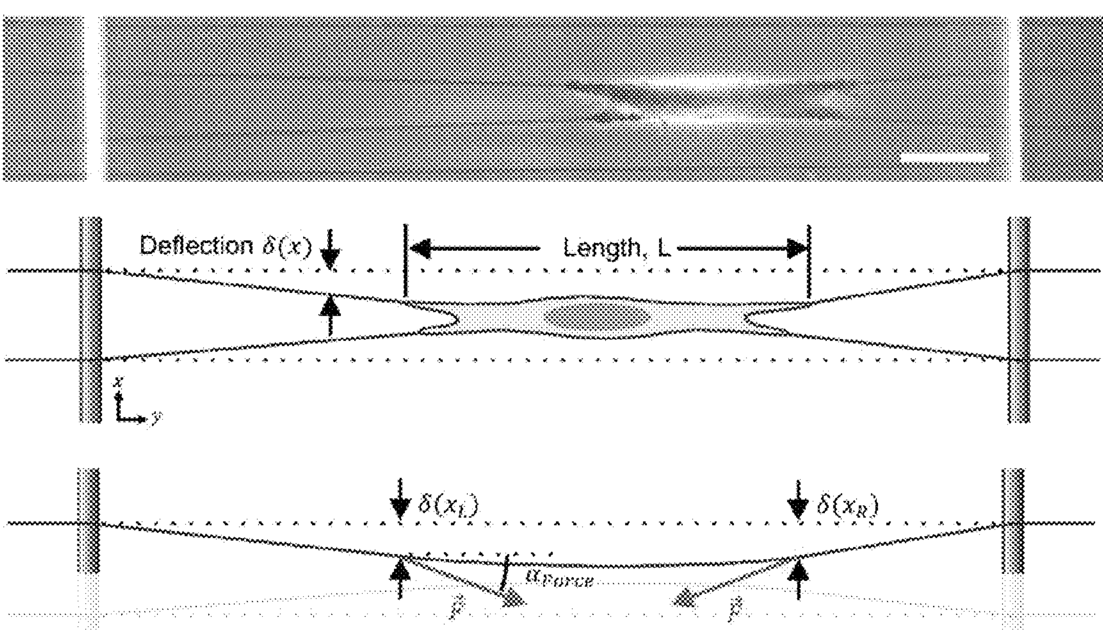
Figure 1D:
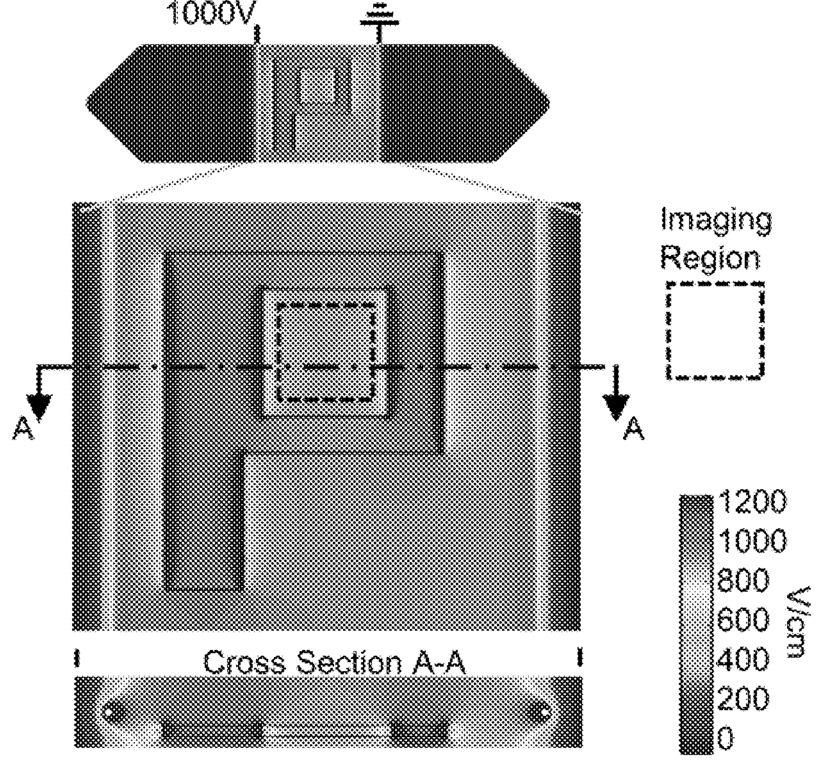
Figure 1E:
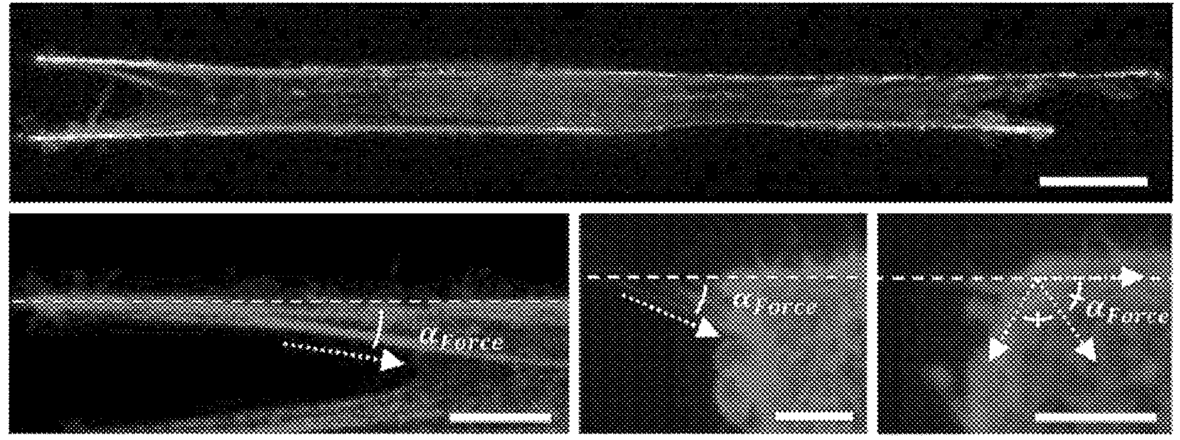
Figure 1F:
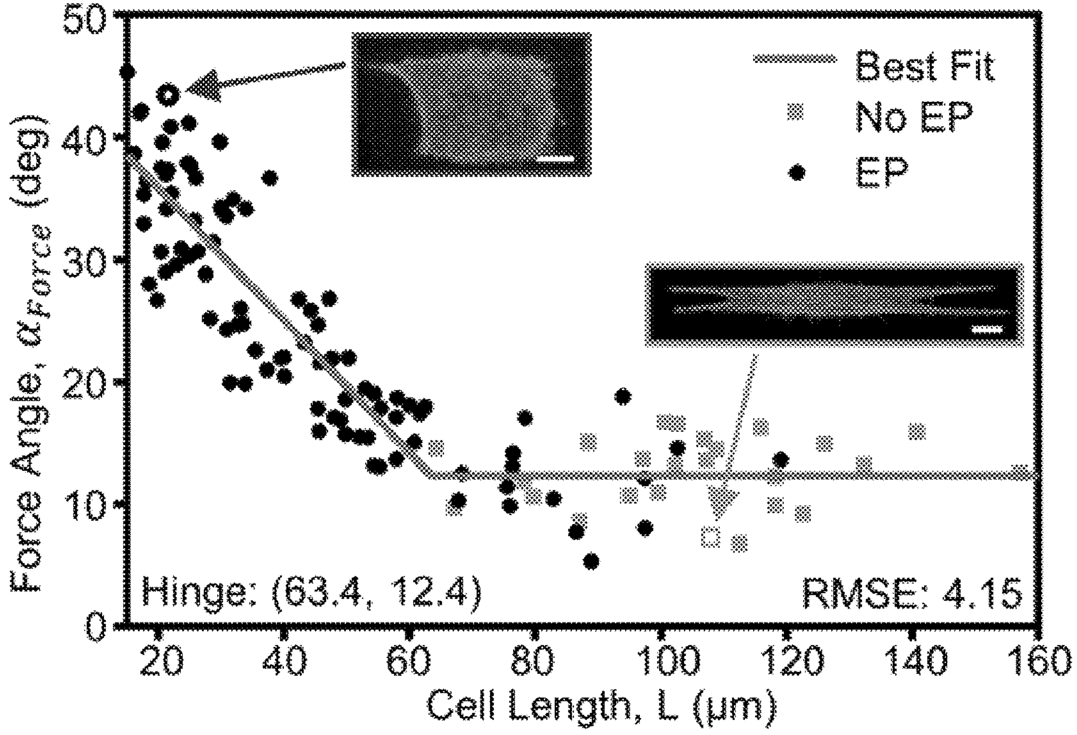
Figure 1G:
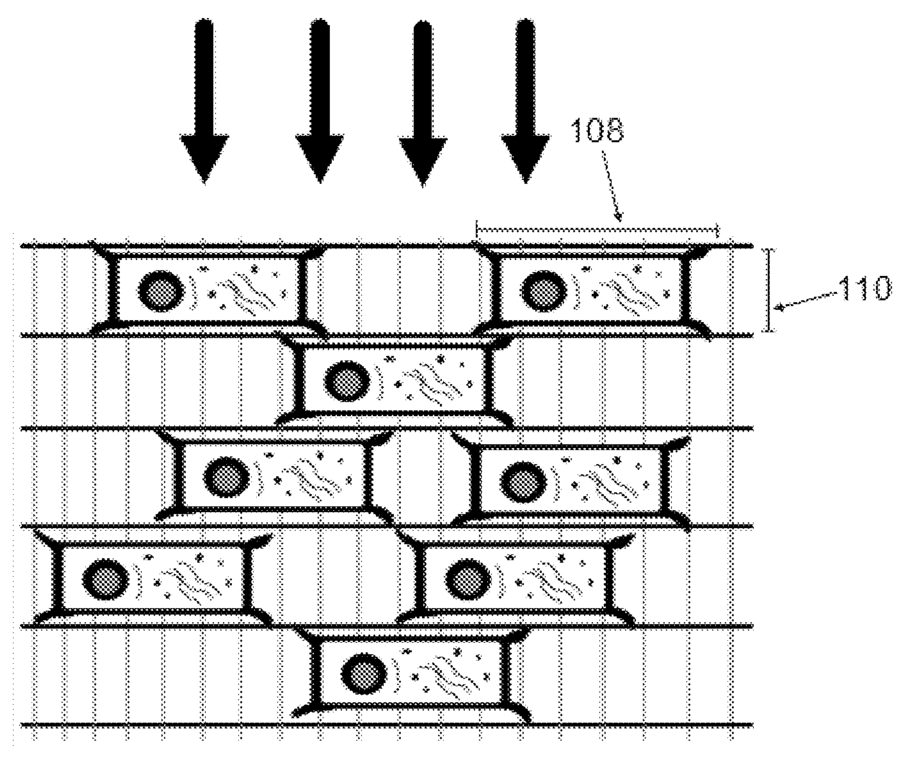
FIG. 1G shows a schematic of cells positioned in a nanofiber array with a perpendicular electric field applied as indicated by the thick black arrows.
Figure 1H:
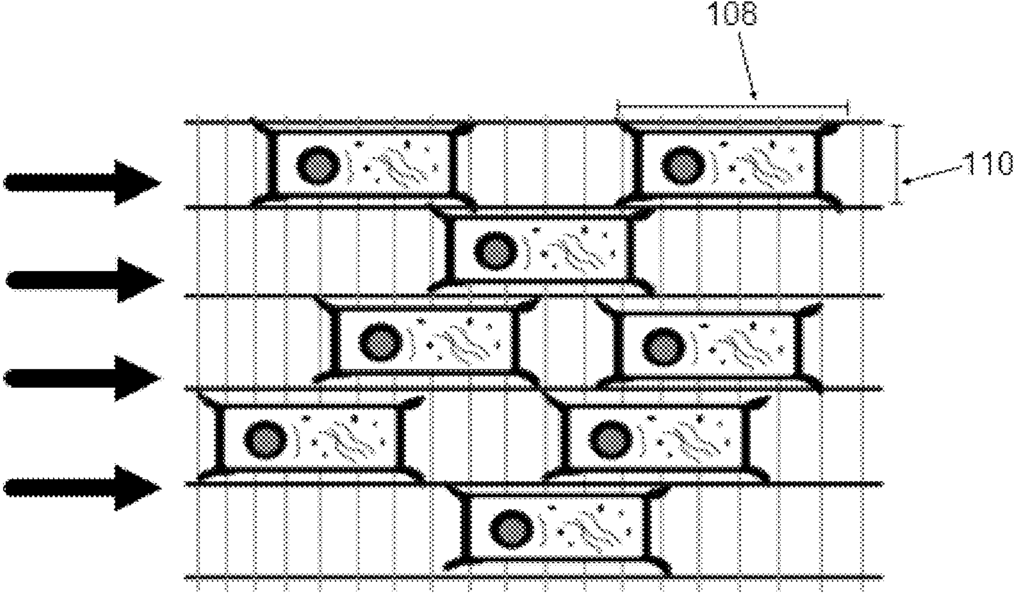
FIG. 1H shows a schematic of cells positioned in a nanofiber array with a parallel electric field applied as indicated by the thick black arrows. Nanofiber diameter in spacing in FIGS. 1G-1H is intended to be generic and is not to scale.
Figure 7A:
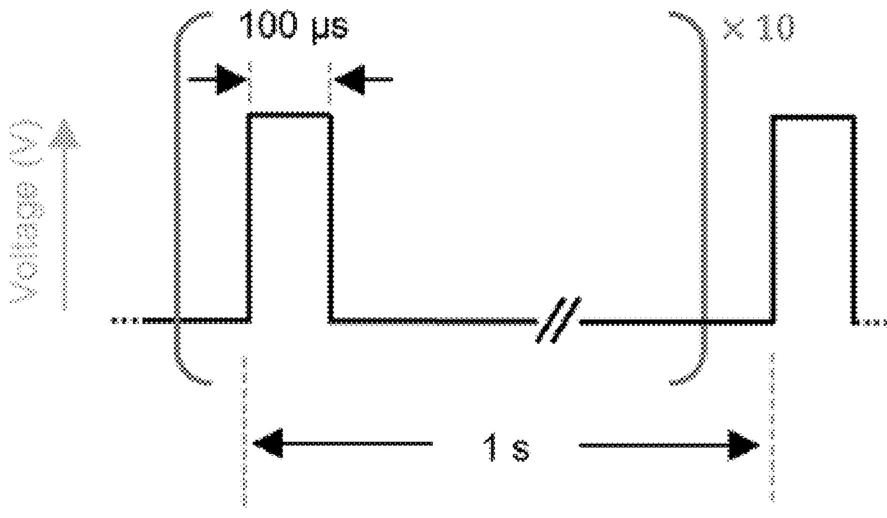
FIGS. 7A-7I show electroporation waveforms the electric field within the device.
Figure 7B:
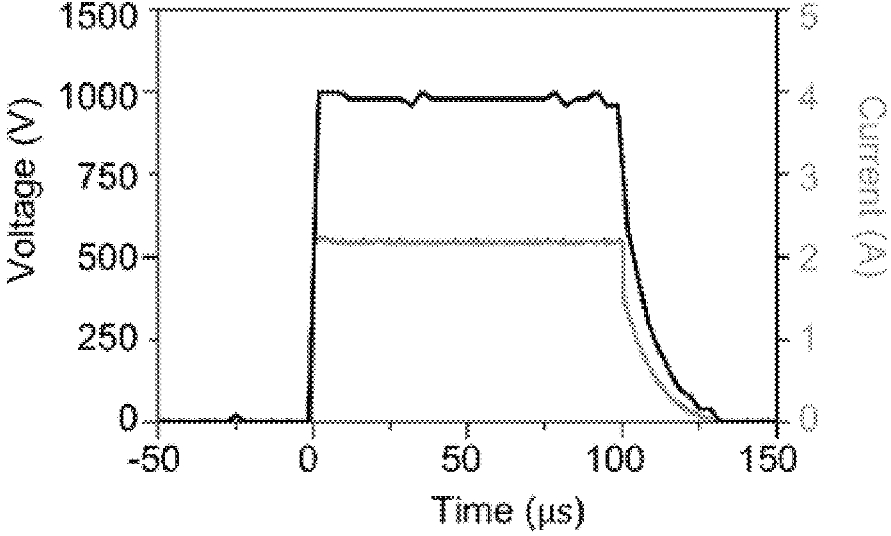
Figure 7C:
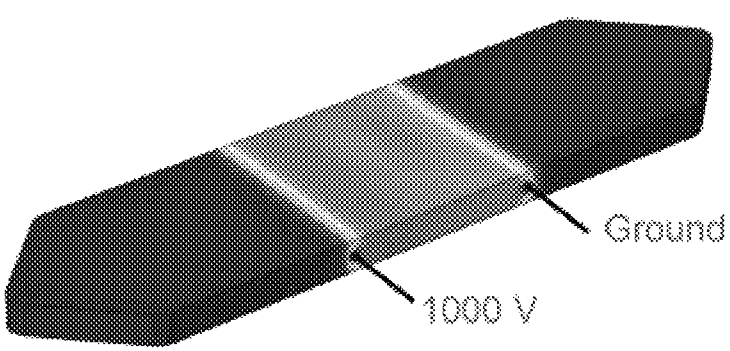
Figure 7C:
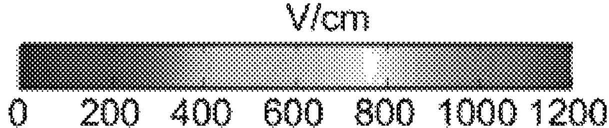
Figure 7D:
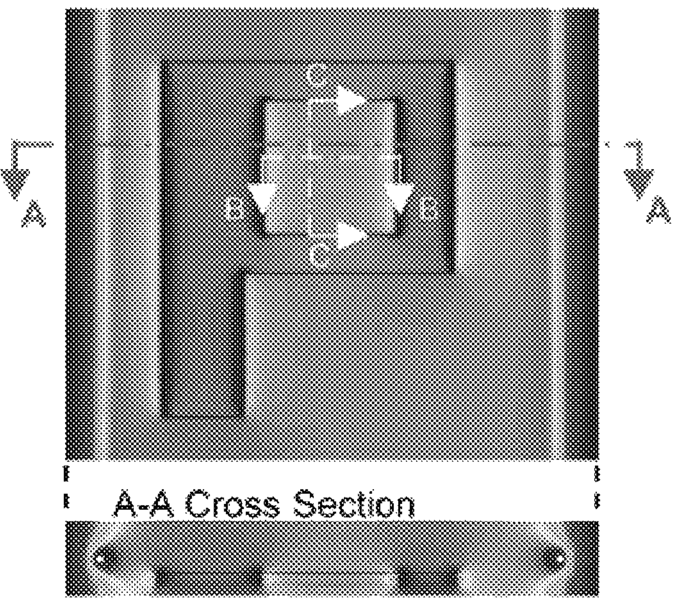
Figure 7E:
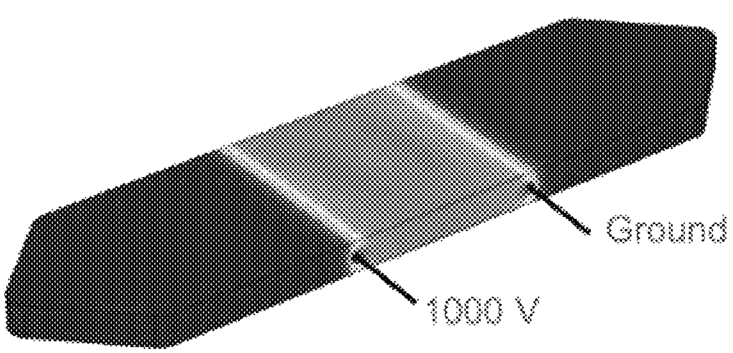
Figure 7E:
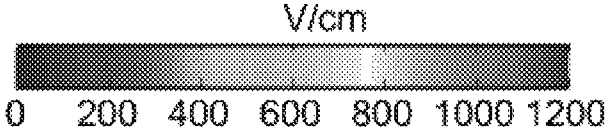
Figure 7F:
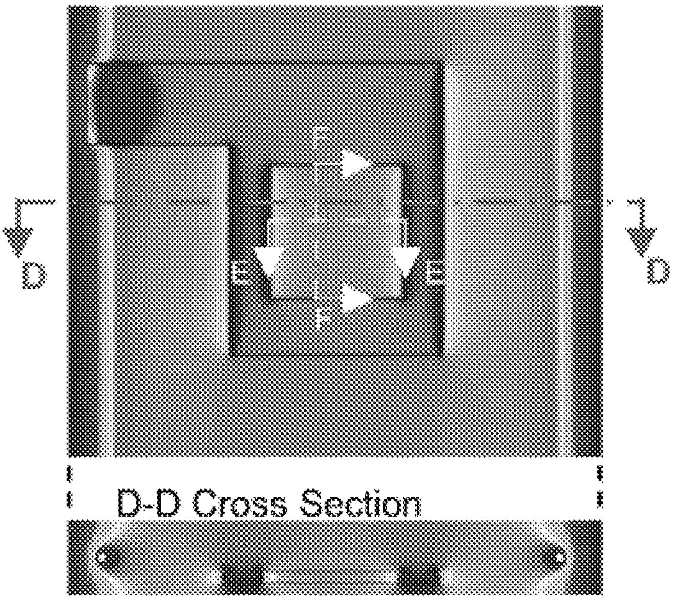
Figure 7G:
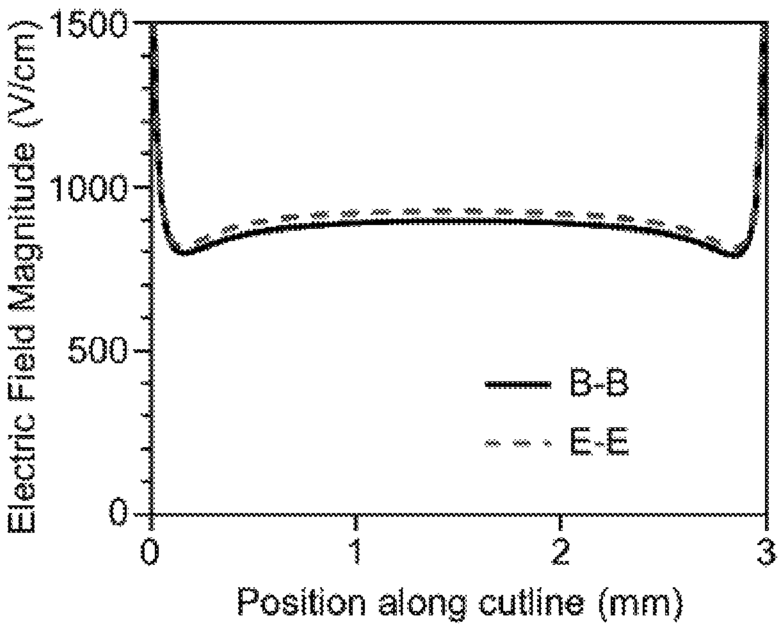
Figure 7H:
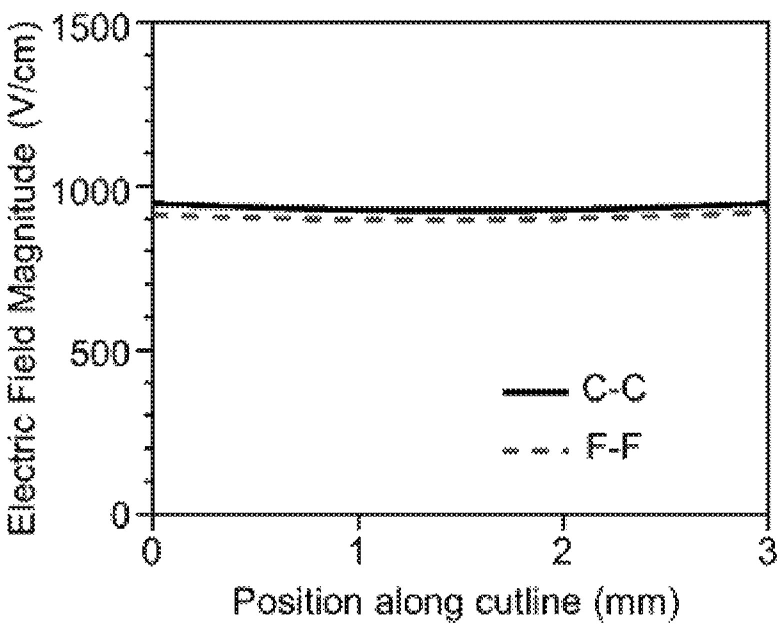
Figure 7I:
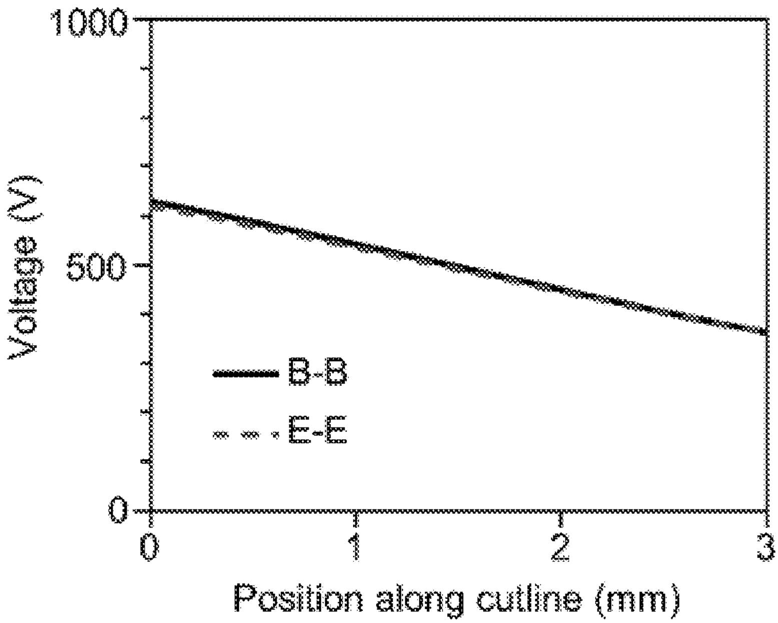

Schematics of cells in a nanofiber array are depicted in FIGS. 1G-1H, showing major axis 108 of cells, minor axis 110 of cells, and direction of electric field indicated by the black arrows (i.e., perpendicular to the major axis of cells in FIG. 1G and parallel to the major axis of cells in FIG. 1H). FIG. 7C shows a finite element model showing the electric field distribution along the walls of the fluidic channel (FIGS. 7C, 7E) and in the plane of the nanofiber scaffold (FIGS. 7D, 7F) according to various aspects of the present disclosure. In FIGS. 7C-7D, the scaffold is modeled in the parallel orientation while FIGS. 7E-7F are modeled with the scaffold in the perpendicular orientation. In one aspect, the nanofiber region within the scaffold has an approximately uniform electric across the center of the scaffold. FIG. 7G shows that along the cutlines B-B and E-E the electric field magnitude is mostly constant, with asymptotic regions near the edges. FIG. 7H shows that, in some aspects, along cutlines C-C and F-F, electric field is quite uniform. FIG. 7I shows that, in a further aspect, the voltage drop is nearly linear along cutlines B-B and E-E. In one aspect, the generated electric fields over the region of interest can be approximately 440 V $cm^{-1}$, 882 V $cm^{-1}$, and 1323 V $cm^{-1}$ respectively across the scaffold region in the parallel orientation and 455 V $cm^{-1}$, 911 V $cm^{-1}$, and 1366 V $cm^{-1}$ respectively across the scaffold region in the perpendicular orientation.

Mechanical Stress

In one aspect, the cells can be at rest and/or not under stress prior to performance of the disclosed methods. In an alternative aspect, the cells can be under mechanical stress prior to and/or during the performance of the disclosed methods. Without wishing to be bound by theory, electroporation can impart significant energy or tension to the cell membrane such that it becomes energetically more favorable for the cell to create hydrophilic pores. In some aspects, the membrane energy stored per unit surface area has mechanical ($T_m$) and electrical ($T_e$) contributions and can be represented as $T=T_m+T_e$. Further in this aspect, the electrical energy can be described as $T_e=\frac{1}{2}\times C\times V^2$, where C is the capacitance per unit area and V is the transmembrane potential. In one aspect, the transmembrane potential increases when an external electric field is applied. In a related aspect, the mechanical energy can be increased when a cell is stressed by a means such as, for example, pressure from a pipette, or extending the fibers of the nanofiber array to stretch the cell. In some aspects, by stretching the cells, the voltage threshold needed for electroporation can be reduced. In a further aspect, when T overcomes a critical threshold ($T_{crit}$), pores can form in the cell membrane.

In one aspect, single cells, cell-cell doublets, and multicellular aggregates can be stretched. In another aspect, stretching of the nanofiber array can be controlled by a computer-controlled probe. In some aspects, cells can be stretched to from about 1% strain to about 50% strain, or at about 1, 5, 10, 15, 20, 25, 30, 35, 40, 45, or about 50% strain, or a combination of any of the foregoing values, or a range encompassing any of the foregoing values. In another aspect, the strain rate for cell stretching can be from about 0.001 μm/s to about 100 mm/s, or can be about 0.001, 0.005, 0.01, 0.05, 0.1, 0.5, 1, 5, 10, 50, 100, or about 500 μm/s, or about 1, 5, 10, 15, 20, 25, 30, 35, 40, 45, 50, 55, 60, 65, 70, 75, 80, 85, 90, 95, or about 100 mm/s, or a combination of any of the foregoing values, or a range encompassing any of the foregoing values. In another aspect, stretching can occur as a cyclic or non-cyclic process.

Shape Change

In a further aspect, applying the electric field can cause the cells to undergo a shape change. In some aspects, the shape change can be rounding, membrane blebbing, cytoskeletal reorganization, or any combination thereof. In some aspects, cytoskeletal reorganization can be actin reorganization, microtubule reorganization, or any combination thereof.

In another aspect, removing the electric field can cause the cells to return to their initial shape. In an alternative aspect, removing the electric field does not cause the cells to return to their initial shape.

Cell Force Response

In one aspect, the methods disclosed herein further include controlling cell force response. In one aspect, actin fibers in the cells adhering to the nanofiber array at focal adhesions enables measurement of cell force response, and cell force response can be measured using nanonet force microscopy.

In one aspect, applying the electric field can cause a characteristic cell force response profile. In a further aspect, the cell force response profile includes a time lag stage, a force bump stage, and a recovery stage.

In one aspect, the time lag stage is from about 0 min to about 10 min after the electric field is applied, the force bump stage is from about 10 min to about 60 min after the electric field is applied, and the recovery stage is from about 60 min to about 150 min after the electric field is applied.

In another aspect, during the time lag stage, cell force response decreases by at least about 50% from an initial cell force response during the time lag stage, or by at least about 55, 60, 65, 70, 75, 80, or about 80% from an initial cell force response. In one aspect, during the time lag stage, cell force response reaches a minimum value of from about 0 nN to about 25 nN, or of about 0, 1, 2, 3, 4, 5, 6, 7, 8, 9, 10, 11, 12, 13, 14, 15, 16, 17, 18, 19, 20, 21, 22, 23, 24, or about 25 nN, or a combination of any of the foregoing values, or a range encompassing any of the foregoing values.

In a further aspect, during the force bump stage, cell force response increases to at least about 90% of the initial cell force response, or at least about 85% of the initial cell force response, or at least about 80% of the initial cell force response, and then decreases by about 50%.

In yet another aspect, during the recovery stage, cell force response increases to from about 90% to about 110% of the initial cell force response, or about 90, 95, 100, 105, or about 110% of the initial cell force response, or a combination of any of the foregoing values, or a range encompassing any of the foregoing values. In a further aspect, cell force response can reach a maximum value of from about 90 nN to about 110 nN during the recovery stage, or of about 90, 91, 92, 93, 94, 95, 96, 97, 98, 99, 100, 101,102, 103, 104, 105, 106, 107, 108, 109, or about 110, or a combination of any of the foregoing values, or a range encompassing any of the foregoing values.

In some aspects, cell force response is exerted by cells, felt by cells, or any combination thereof.

In one aspect, controlling cell shape and cell force response can impact the size and distribution of pores in the cell membrane. In another aspect, pore size can be fine-tuned by varying factors including (i) diameter of nanofibers in the nanofiber array, (ii) spacing of nanofibers, (iii) direction of electric field, and (iv) voltage magnitude of the electric field.

In one aspect, methods are provided herein for measuring single and multi-cell forces on a fused net of polymeric nano- and micro-fibers. In another aspect, methods and systems are provided where single and multi-cells are attached to a net of polymeric nano- and micro-fibers and forces generated by the cells can be observed and measured. Further in this aspect, methods and systems for measuring cellular forces in response to external perturbations at high magnifications and in real time are described herein.

In some aspects, cells receive physical and chemical cues from their surrounding microenvironment known as the extracellular matrix (ECM), which consists of protein fibrils (30-70 nm in diameter), which can bundle into 200 nm-1 μm fibers, with composition and structure that varies temporally and spatially in the body In another aspect, mechanical communication between a cell and its substrate may occur bi-directionally through integrin-mediated focal adhesions. Cells generate forces via actomyosin contractions that act on their surroundings (inside-out, IO) but also respond to forces originating outside the cell which are transmitted through adhesion sites to the cytoskel-etal network (outside-in, OI)

In a still further aspect, both directions are physiologically relevant, as seen in the example case of arteries where smooth muscle cells generate IO contractile forces that control vessel constriction to modulate blood pressure, but also experience OI forces from vessel expansion with each heartbeat that cause the cell to reorient actin stress fibers In one aspect, the influence of physical forces exerted or felt by cells on cell shape, cytoskeletal organization, and migration speed as well as disease onset is acknowledged and, without wishing to be bound by theory, hypothesized to occur due to modulation of cellular IO forces in response to changes in the external fibrous environment or OI forces. Various force measurement techniques have been developed to probe single and multi-cell behavior. For example, IO forces can be measured by measuring the deformation using such as traction force gels or micropillar arrays In another aspect, cells pull on the underlying sub-strate as they migrate, resulting in deflections which can be measured and converted to forces. In yet another aspect, conversely, OI platforms require an active component that applies forces to the cell or its substrate. In one aspect, such approaches include, but are not limited to, use of atomic force microscopy (AFM) cantilevers, microfluidic devices that incorporate fluid shear, active stretching of traction force gels or micropillar arrays substrates, a variety of micro-electromechanical systems (MEMS) devices, and combinations thereof. In some aspects, however, these meth-ods may be unable to capture the fibrous extra-cellular matrix (ECM) biophysical interactions, involving param-eters of curvature, structural stiffness (N/m), alignment and hierarchy, which have been shown to play key roles in disease and developmental biology.

In one aspect, force measurement platforms able to cap-ture both IO and OI forces can distinguish forces that cells exert from forces that they can withstand, with applications in the inves-tigation of disease models, such as, for example, disease states where progression from normal function to failure either occurs rapidly or without warning or detection, e.g., bone fracture, muscle or ligament tears, blood vessel aneurysms. In a further aspect, force measurement platforms using scaffolds having characteristics similar to those of the ECM are particularly useful to probe single and multi-cell behavior.

In one aspect, methods and systems are provided herein for measuring single and multi-cell outside-in forces on a fused net of polymeric nano- and micro-fibers. In a further aspect, outside-in cell forces, or forces that cells can with-stand upon an external perturbation, which may be symmet-ric or asymmetric, that can be measured on a fused net of polymeric nano- and micro-fibers include forces in response to single or multi-probe perturbation, force relax-ation upon strain, cell-cell junctions, and drug response. In a further aspect, the probes can be moved at prescribed strain rates and amplitudes with independent control. In some aspects, these platforms can use automated processes for any step of the methods described herein, including analyzing cells. In some optional aspects, the methods can be computer-imple-mented methods for calculating outside-in forces of cells according to the methods described herein.

In some aspects, in the disclosed methods of measuring single and multi-cell forces on a fused net of nano- and micro-fibers, a nanofiber grid having a plurality of high aspect ratio polymeric fibers can prepared, wherein the fibers are formed into a crossed pattern (at least one fiber crosses another fiber) and the fibers are fused where they intersect in the crossed pattern. In other aspects, the nanofiber grid can optionally be coated with an adhesive coating. In one aspect, a single cell or cell type, or multiple cells or cell types can be deposited on, or migrate onto the nanofiber grid, where the cell or cells are in contact with at least one fiber of the nanofiber grid. In a further aspect, the extent of deflection of the fiber in contact with the cell can be measured using deflection sensing strategy including, but not limited to, optical microscopy, electron microscopy, or capacitive sens-ing, leading to calculation of the corresponding forces acting on the displaced fiber.

In one aspect, described herein are methods for measuring single and multi-cell forces on a fused net of nano- and micro-fibers, e.g., polymeric fibers. In a further aspect, provided herein are apparatuses and systems where single and multi-cells can be attached to a net of nano- and micro-fibers and forces generated by the cells can be observed and measured. In a further aspect, a platform for measuring cellular forces in response to external perturba-tions at high magnifi-cations and in real time is described herein.

As used herein, the term "nanofiber grid", or "nanonet" refers to a scaffold that is prepared from nano- and micro-fibers. In one aspect, the fibers are polymeric, as can be produced, e.g., using the non-electrospinning technique as described herein. In a further aspect, using this technique, high aspect ratio polymeric fibers with controlled diameters are arranged in criss-cross (crossed) grids and fused at the fiber intersections can be used to create suspended force measurement structures of tunable structural stiffness (in N/m). In a further aspect, fibers are typically circular in cross-section, but in some aspects can have non-circular cross-sectional profiles, e.g., ribbon-like flat fibers. In one aspect, reference to a diameter of a fiber is in relation to the fiber's smallest cross-sectional dimension.

In certain aspects of the methods and systems described herein, these nanonets, which possess characteristics similar to those of the ECM, can be seeded with single and multi-cells, which allows cellular forces to be evaluated via Nanonet Force Microscopy or other methods. As used herein, the term "Nanonet Force Microscopy (NFM)" refers to the technique of using fiber deflections to calculate the forces exerted or felt by cells attached to nanon-ets. In one aspect, the properties of nanonets including elastic modulus and structural stiffness can be measured using Atomic Force Microscopy (AFM) or another technique.

In certain aspects of the methods and systems described herein, cells can exert 10 forces via actomyosin contractions and they may also be able to withstand O forces originating outside the cell, which can be transmitted through adhesion sites to the cytoskeletal network. In addition to observing contractile 10 forces generated by cells attached to nanonet fiber segments (attachment, protrusions, migration, division, apoptosis, leader cell, cell aspiration, debris, drug response), in one aspect, external micropipette-based perturbation (symmetric and asymmetric) can be used to measure the cell's mechanical response, load distribution, and/or failure behavior. In another aspect, perturbations of single cells and cell-cell pairs attached to nanonets of different diameters reveal that bias (asymmetric loading) does not affect the maximum adhesion force of the cell, but rather redistributes the forces within the cell in a diameter-dependent manner. In some aspects, these effects may be due to curvature-induced reorientation and redistribution of focal adhesion sites In one aspect, the non-electrospinning technique used herein allows the production of hierarchical assemblies of aligned nanofibers, to which single cells and multi-cell can be attached. In some aspects, suspended fibers may provide cells with simultaneous 1, 2, and 3D mechanistic cues and are known to elicit changes in cell behaviors such as adhesion, migration, and cytoskeletal arrangement. In one aspect, cells attached to suspended fibers are able to sense and respond to changes in fiber curvature and structural stiffness as evidenced by alterations to focal adhesion cluster lengths.

In one aspect, contractility-based inside-out forces can be evenly distributed at the edges of the cell and overall force magnitudes may be dependent on fiber structural stiffness. In another aspect, external perturbation in symmetric and asymmetric modes biases cell-fiber failure location, without affecting the outside-in forces of cell-fiber adhesion.

In one aspect, the amount of force applied by a probe to a fiber can be determined a number of ways. In one aspect, the force applied to the fiber can be used as feedback to limit motion of the probe. In another aspect, the force sensor can be included within the robotic device used to control the probe, for example by attaching a force sensor to the probe. In still another aspect, the displacement of the fiber by the probe can be used to determine the amount of force applied. Further in this aspect, the displacement of the fiber, and position of the probe can be tracked by analyzing images of the fiber and probe.

According to one aspect of the disclosure, a method is provided for measuring a cell force, that is an outside-in and/or an inside-out force as described herein. In a further aspect, the method includes depositing a cell or cells on a nanofiber array suspended in an aqueous medium in a vessel comprising a plurality of high aspect ratio polymeric fibers having diameters of between about 10 nm and 10 μm, wherein the fibers are formed into a crossed pattern having one or more intersections, and wherein the fibers are fused at the intersections of the crossed pattern, wherein the at least one cell is in contact with a first fiber; measuring deflection of the first fiber in contact with the at least one cell; and calculating from the deflection of the first fiber a force applied to the fiber by the cell. In an alternative aspect, the cell can be attached to multiple fibers; and calculating the deflections of multiple fibers to obtain the forces applied to multiple fibers.

In a further aspect, the cell can also be attached to a second fiber, and the method further includes, prior to measuring the deflection of the at least one fiber, moving a second fiber attached to the cell using a first probe placed at a point on the second fiber adjacent to the cell on a first side of the cell between the cell and a first intersection adjacent to the cell. In one aspect, the cell, as well as the points on the first and second fiber, can be located between two adjacent intersections (the closest intersections). A “probe” in the context of use to move one or more of the described fibers can be any rigid or semi-rigid structure able to move a fiber in a controlled manner, and which does not interfere with the operation of the described methods. In some aspects, a probe can be constructed any material that does not perturb the operation of the described methods, and is therefore preferably non-reactive, and can be glass, ceramic, amorphous, polymeric, metallic, crystalline, carbon fiber, composite, or any combination thereof.

Cell Length

In some aspects, the initial cell shape includes an initial cell length. In another aspect, the initial cell length can be about 100 μm. In another aspect, applying the electric field causes the cell to adopt a second length. In some aspects, the second length is shorter than the initial length.

In one aspect, during the time lag stage, the second length is from about 50% to about 75% of the initial length, or is about 50, 55, 60, 65, 70, or 75% of the initial length, or a combination of any of the foregoing values, or a range encompassing any of the foregoing values. In one aspect the second length is from about 25 μm to about 50 μm during the time lag stage, or is about 25, 26, 27, 28, 29, 30, 31, 32, 33, 34, 35, 36, 37, 38, 39, 40, 41, 42, 43, 44, 45, 46, 47, 48, 49, or about 50 μm, or a combination of any of the foregoing values, or a range encompassing any of the foregoing values.

In one aspect, during the recovery stage, the second length is from about 90% to about 110% of the initial length, or is about 90, 91, 92, 93, 94, 95, 96, 97, 98, 99, 100, 101, 102, 103, 104, 105, 106, 107, 108, 109, or about 110% of the initial length, or a combination of any of the foregoing values, or a range encompassing any of the foregoing values. In another aspect, the second length can be from about 90 μm to about 110 μm, or can be about 90, 91, 92, 93, 94, 95, 96, 97, 98, 99, 100, 101, 102, 103, 104, 105, 106, 107, 108, 109, or about 110 μm, or a combination of any of the foregoing values, or a range encompassing any of the foregoing values.

Membrane Permeability

In one aspect, applying the electric field increases membrane permeability of the cells relative to an initial state of membrane permeability. In another aspect, the cells can return to the initial state of membrane permeability following removal of the electric field.

In one aspect, assessing membrane permeability includes:

a. visualizing the cells a first time;
b. contacting the cells with a membrane-impermeant stain;
c. visualizing the cells a second time; and
d. quantifying a difference n images produced by steps (a) and (c).

In some aspects, the cells can be visualized by fluorescence microscopy, brightfield microscopy, or another method. In one aspect, the membrane-impermeant stain can be propidium iodide, a modified green fluorescent propidium iodide (e.g. YO-PRO™-1 from Thermo Fisher Scientific), or any combination thereof.

In one aspect, visualizing the cells a second time can result in an increased signal compared to visualizing the cells a first time. In another aspect, the increased signal correlates with increased membrane permeability.

In another aspect, visualizing the cells a second time results in a decreased signal compared to visualizing the cells a first time. In a further aspect, the decreased signal correlates with decreased membrane permeability or a return to the initial state of membrane permeability.

In one aspect, membrane permeability increases within about 10 sec of applying the electric field. In another aspect, membrane permeability can return to the initial state within about 30 min of removing the electric field.

In a still further aspect, disclosed herein is a method for introducing a compound into cells, the method including at least the following steps:

a. performing the method for controlling cell shape as disclosed herein; and
b. exposing the cells to the compound.

In a further aspect, the compound can be or include a nucleic acid, a vector, a peptide or protein, a membrane-impermeant stain, a pharmaceutical compound, a cryoprotectant, one or more exogenous organelles, a molecular probe, nanodevices, nanoparticles, or any combination thereof. Also disclosed are cells produced by the methods disclosed herein.

Cell Viability and Reversible Electroporation

In one aspect, following applying the electric field, the cells remain viable. In another aspect, following applying the electric field, the cells do not remain viable.

In one aspect, previously, large cells were associated with more favorable reversible electroporation outcomes. In another aspect, it has been unexpectedly discovered that in the methods disclosed herein, more favorable reversible electroporation outcomes can result from applying an electric field along the shorter axis of cells.

In one aspect, when the cells remain viable and include an inserted nucleic acid (i.e., are “transfected”), when the cells reproduce, the nucleic acid can also reproduce and be present in any progeny cells of the transfected cells.

In one aspect, viability in cells attached to nanofibers while undergoing electroporation and/or other exposure to an electric field can be enhanced versus the same cells undergoing electroporation and/or electric field exposure in the absence of nanofibers.

In one aspect, reversible electroporation (i.e., achieving viable cells following application of the disclosed methods) is a function of a number of parameters including pulse shape, number, cell geometry, cell size, and combinations thereof. In one aspect, if the induced transmembrane potential is on the order of 300 mV, the pulses can reversibly electroporate the cell membrane. In another aspect, an induced potential on the order of 1 V can induce irreversible electroporation (i.e., leading to cell death). In one aspect, in an idealized spherical cell where the pulse length is much longer than the charging time of the cell membrane, then the maximum induced transmembrane potential can be modeled as $V_{m,i}=1.5\times E\times a$, where E is the local electrical field and a is the radius of the cell. In one exemplary aspect, if a 10 μm cell is exposed to a field of 1 kV/cm, the induced transmembrane potential is 1V.

In a further aspect, the local field is a function of the applied voltage and the distance between the electrodes. In one example aspect, the electrodes can be about 1 cm apart, so a voltage of 1000 V would be required to achieve a local field on the order of 1 kV/cm. In another aspect, using lithography techniques, the spacing can be much closer (for example, on the order of from about 100 μm to about 1000 μm). Further in this aspect, the applied voltage can be from about 10 V to about 100 V, respectively.

In another aspect, when performing the disclosed methods on cells, the electric field strength can be from about 25 V/cm to about 30,000 V/cm, or can be about 25, 50, 100, 500, 1000, 1500, 2000, 2500, 5000, 10,000, 15,000, 20,000, 25,000, or about 30,000 V/cm, or a combination of any of the foregoing values, or a range encompassing any of the foregoing values. In one aspect, when the cells are mammalian cells, the field strength can be from about 25 V/cm to about 3000 V/cm. In another aspect, when the cells are bacterial cells, the field strength can be up to about 30,000 V/cm.

In one aspect, when performing reversible electroporation on mammalian cells, the electric field strength can be from about 25 V/cm to about 1000 V/cm, or from about 200 V/cm to about 500 V/cm, or can be about 25, 50, 100, 150, 200, 250, 300, 350, 400, 450, 500, 550, 600, 650, 700, 750, 800, 850, 900, 950, or about 1000 V/cm, or a combination of any of the foregoing values, or a range encompassing any of the foregoing values. In some aspects, when the electrodes are closer together than 1 cm, an electric field with a higher magnitude can be achieved with a lower applied voltage. Thus, for example, an electric field of 500 V/cm could be achieved with an application of only 25 V. In one aspect, in reversible electroporation, the cells are viable following performance of the disclosed method.

Electroporation and Cellular Contraction

In one aspect, it has been suggested that the cytoskeleton is disrupted directly or indirectly by electroporation. Further in this aspect, during electroporation, contractile forces are generated within cells by filamentous actin that anchor to the extracellular matrix by focal adhesions. In another aspect, actin also interacts with the cell membrane to provide structural support for the lipid membrane. Further in this aspect, actin interactions with the membrane have been hypothesized to impact the resealing time of pores. In one aspect, then, mechanical analysis of the cell, for example via contractile forces, is therefore a useful means to investigate cytoskeletal effects and monitor cell recovery in a more holistic manner. In some aspects, mechanobiology has shown that cells exert quantifiable forces on the extracellular matrix that determine intracellular function, cell signaling, and cell behavior. Still further in this aspect, the contractile nature of cells may provide a new way to measure cell recovery after electroporation that is both dye-free and not reliant simply on membrane resealing.

In one aspect, conventionally, electroporation in vitro is delivered to cells in a suspension, adherent to a flat 2D surface, or in a 3D hydrogel setting. Disclosed herein is the use of nanofibers to study the mechanical response due to electric fields of cells in a precisely engineered environment. In one aspect, unlike with conventional electrospinning techniques, a non-electrospinning technique known as Spinneret based Tunable Engineered Parameters (STEP) can be useful herein. In a further aspect, scaffolds having highly-controlled scaffold geometries can be constructed. In one aspect, disclosed herein are parallel nanofibers bonded to larger orthogonal fibers form a scaffold that enables cells to adhere between two parallel fibers and deflect the fibers according to the cell's contractile force. In a further aspect, using this nanofiber scaffold, cell recovery after electroporation can be measured by calculating the contractile force response. In one aspect, the contractile force of cells suspended between parallel nanofibers after applying electroporation pulses at three magnitudes (500 V/cm, 1000 V/cm, and 1500 V/cm) and two electric field directions (parallel and perpendicular to the cell's long-axis can be investigated.

In one aspect, contractile forces can provide significant insight into cell recovery. Further in this aspect, cytoskeletal staining reveals significant disruption within 30 minutes after pulsing. In another aspect, cells display significantly different contractile behavior based on the orientation of their long-axis to the electric field. In another aspect, surprisingly, computational models of induced transmembrane potential do not well predict the viability differences due to orientation. In one aspect, mechanical force recovery is a multi-stage process having an initial unexpected bi-phasic recovery and relaxation followed by a gradual recovery to pre-electric field application cell contractile forces. In another aspect, the force signature during the initial bi-phasic phase correlates with the strength of electrical pulse, coincides with microtubule disruption driven blebbing, and is almost exclusive to in-line electric perturbation. In one aspect, almost negligible cell viability observed in transverse high electric fields contradict current predictions from models.

In one aspect, disclosed herein is a new method for evaluating cell recovery by quantifying the mechanical response of elongated cancer cells to membrane disruption by electroporation. In another aspect, the disclosed mechanics-based approach to cell recovery can provide further understanding about how cells respond to electric fields. In a still further aspect, engineering cell shape to maximize both membrane disruption and viability could enable higher transfection efficiencies than current electroporation transfection strategies. In one aspect, understanding the relationship between cell mechanics and survival can yield valuable information for optimizing cell death during tumor ablation by irreversible electroporation.

In another aspect, electroporation incorporating the methods disclosed herein can increase efficiency in gene transfection. In a further aspect, the methods disclosed herein can control the density and colocalization of exogenous genes within cells. In a still further aspect, the methods disclosed herein are capable of synchronizing cell mechanical response (e.g., by shape change or length change or another form of cytoskeletal reorganization) with gene delivery.

In some aspects, the disclosed methods allow various media perturbations in order to enhance cell viability and gene delivery via electroporation. In one aspect, calcium has been implicated in disassembly of focal adhesions. In a further aspect, the disclosed methods can enable the use of calcium-free media, thereby maintaining focal adhesions, for example, to a nanofiber array. In another aspect, calcium concentration in the growth media can be tuned to the particular cell type and/or growing conditions. In one aspect, increased calcium concentration can enhance cell permeability to molecules and/or drugs during electroporation. In a still further aspect, other media perturbations can also be employed in the disclosed methods.

In one aspect, the method can be conducted in a chamber that is open, or that has a removable lid, in order to allow pipetting of cells into the chamber or removal of cells from the chamber. In some aspects, the chamber can be incubated post-transfection to culture cells. In some aspects, the cells can be incubated at about 37° C. for mammalian cells. In another aspect, the cells can be incubated at another temperature such as, for example, 30° C., or at any temperature established for culturing a specific cell type.

Aspects

The present disclosure can be described in accordance with the following numbered Aspects, which should not be confused with the claims.

Aspect 1. A method for modifying at least one cell, the method comprising applying an electric field to a nanofiber array comprising the plurality of cells, wherein the nanofiber array comprises a first array of first fibers and a second array of second fibers, wherein the first fibers are positioned at an angle of from about 0° to about 90° to the second fibers.

Aspect 2. The method of aspect 1, wherein the at least one cell comprises a mammalian cell, a non-mammalian vertebrate cell, an invertebrate cell, a plant cell, a fungal cell, a bacterial cell, an archaeal cell, a protozoal cell, an engineered cell, or a combination thereof.

Aspect 3. The method of aspect 2, wherein the mammalian cell comprises a glioblastoma cell and/or another brain cancer cell, a liver cancer cell, a breast cancer cell, an ovarian cancer cell, a prostate cancer cell, a cervical cancer cell, a skin cancer cell, a mesothelioma cell, a dendritic cell, a hepatocyte, a pancreatic islet, a fibroblast including a cancer-associated fibroblast, a stem cell including a totipotent, pluripotent, and/or multipotent stem cell, a mouse myoblast, a smooth muscle cell, a cardiomyocyte, a Chinese hamster ovary cell, or any combination thereof.

Aspect 4. The method of any of aspects 1-3, wherein providing a scaffold comprises:

a. providing a master mold;
b. casting a resin in the master mold;
c. curing the resin to form a cured resin;
d. removing the cured resin from the mold;
e. attaching the cured resin to a substrate; and
f. contacting the cured resin with at least two electrodes.

Aspect 5. The method of aspect 4, wherein the resin comprises a silicone.

Aspect 6. The method of aspect 5, wherein the silicone comprises a crosslinkable silicone.

Aspect 7. The method of aspect 5 or 6, wherein the silicone comprises polydimethylsiloxane.

Aspect 8. The method of any of aspects 5-7, wherein the resin further comprises a crosslinker.

Aspect 9. The method of aspect 8, wherein the silicone and crosslinker are present in a ratio of about 10:1 (wt/wt).

Aspect 10. The method of any of aspects 4-9, wherein the resin is cured at about 80° C.

Aspect 11. The method of any of aspects 4-10, wherein the resin is cured for about 4 h.

Aspect 12. The method of any of aspects 4-11, wherein the substrate comprises glass.

Aspect 13. The method of any of aspects 4-12, wherein the cured resin is attached to the substrate using a plasma cleaner.

Aspect 14. The method of any of aspects 4-13, wherein the electrodes comprise stainless steel, gold, platinum, a conductive epoxy, gold with a titanium adhesion layer, or any combination thereof.

Aspect 15. The method of any of aspects 4-14, wherein the electrodes are placed on the scaffold at a distance of from about 100 μm to about 1 cm apart.

Aspect 16. The method of any of aspects 4-15, wherein the electrodes are placed on the scaffold at an angle of from 0° to 90° with respect to one another.

Aspect 17. The method of any of aspects 4-16, wherein the electrodes are parallel.

Aspect 18. The method of any of aspects 4-17, wherein the electrodes are fixed in place with an adhesive, deposited using a lithography technique including sputtering, deposition, or lift-off.

Aspect 19. The method of aspect 18, wherein the adhesive comprises epoxy.

Aspect 20. The method of any of aspects 1-19, wherein contacting the scaffold with a nanofiber array comprises:

a. mounting the scaffold on a motor and rotating the scaffold;
b. using a microneedle to extrude a first array of fibers;
c. turning the scaffold from 0° to an angle of from 1° to 90°;
d. using the microneedle to extrude a second array of fibers perpendicular to the first array of fibers; and
e. crosslinking the first array of fibers with the second array of fibers to form a nanofiber array.

Aspect 21. The method of aspect 19, wherein the first array of fibers, the second array of fibers, or both the first array of fibers and the second array of fibers comprise polystyrene, a polyester, a polyurethane, a polyacrylamide, a poly(methyl methacrylate), a polylactic acid, a poly(glycolic acid), a poly(lactic-co-glycolic acid), a polyaniline, a polypyrrole, a polyethylene oxide, fibrinogen, collagen, mixtures and/or copolymers thereof, carbon nanotubes, carbon black, metallic nanoparticles, or any combination thereof.

Aspect 22. The method of aspect 21, wherein the polystyrene is dissolved in a solvent during extrusion.

Aspect 23. The method of aspect 22, wherein the solvent comprises p-xylene, n-octane, n-dodecane, cyclohexane, methylcyclohexane, benzene, toluene, o-xylene, ethyl benzene, p-diethyl benzene, chloromethane, methylene chloride, 1,1-dichloroethylene, ethylene dichloride, chloroform, 1,1-dichloroethane, trichloroethylene, carbon tetrachloride, chlorobenzene, o-dichlorobenzene, tetrahydrofuran, 1,4-dioxane, dibenzyl ether, acetone, methyl ethyl ketone, cyclohexanone, diethyl ketone, acetophenone, ethyl formate, ethyl acetate, nitrobenzene, pyridine, morpholine, N-methyl-2-pyrrolidone, N—N-dimethylformamide, dimethylsulfoxide, ethanol, allyl alcohol, 1-propanol, 2-propanol, 1-butanol, 2-butanol, benzyl alcohol, cyclohexanol, ethylene glycol monoethyl ether, diethylene glycol monomethyl ether, 1-decanol, benzoic acid, phenol, ethylene glycol, glycerol, propylene glycol, or any combination thereof.

Aspect 24. The method of any of aspects 20-23, wherein the first array of fibers comprises a plurality of first fibers having a diameter of from about 2 μm to about 10 μm.

Aspect 25. The method of aspect 24, wherein the first fibers are spaced from about 50 μm to about 1 mm apart.

Aspect 26. The method of any of aspects 20-25, wherein the second array of fibers comprises a plurality of second fibers having a diameter of from about 100 nm to about 2 μm.

Aspect 27. The method of aspect 26, wherein the second array of fibers comprises a plurality of second fibers having a diameter of about 250 nm.

Aspect 28. The method of aspect 26, wherein the second fibers are spaced about 10 μm apart.

Aspect 29. The method of any of aspects 1-28, wherein contacting the nanofiber array with cells comprises placing a droplet of a solution containing the at least one cell on the nanofiber array.

Aspect 30. The method of aspect 29, wherein the solution contains from about 50,000 cells/mL to about 150,000 cells/mL.

Aspect 31. The method of aspect 28 or 29, wherein the droplet is about 35 μL.

Aspect 32. The method of any of aspects 28-31, further comprising incubating the droplet of solution containing the at least one cell and the nanofiber array for from about 1 h to about 48 h.

Aspect 33. The method of any of the preceding aspects, wherein the at least one cell comprises a major axis and a minor axis, and wherein the major axis intersects the minor axis.

Aspect 34. The method of aspect 33, wherein the major axis is longer than the minor axis.

Aspect 35. The method of aspect 33, wherein the major axis and the minor axis are about the same length.

Aspect 36. The method of any of aspects 33-35, wherein the at least one cell is oriented in the nanofiber array such that the cell lies between the second fibers, the major axis of the cell is parallel to the second fibers, and the minor axis of the cell is perpendicular to the second fibers.

Aspect 37. The method of aspect 36, wherein the cell comprises a spindle shape, a polygonal shape, an elongated shape, or any combination thereof.

Aspect 38. The method of any of aspect 33-37, wherein the at least one cell grows as an individual cells, as a monolayer, in spheroids, or any combination thereof.

Aspect 39. The method of any of aspects 1-38, wherein the electric field is applied at an angle of from about 0° to about 90° with respect to the major axis of the at least one cell.

Aspect 40. The method of any of aspects 1-38, wherein the electric field is applied in a parallel direction with respect to the major axis of the at least one cell.

Aspect 41. The method of any of aspects 1-38, wherein the electric field is applied in a perpendicular direction with respect to the major axis of the at least one cell.

Aspect 42. The method of any of the preceding aspects wherein the electric field comprises an applied field strength of from about 250 V/cm to about 30,000 V/cm.

Aspect 43. The method of aspect 42, wherein the electric field strength is about 250 V/cm.

Aspect 44. The method of aspect 42, wherein the electric field strength is about 500 V/cm.

Aspect 45. The method of aspect 42, wherein the electric field strength is about 1000 V/cm.

Aspect 46. The method of aspect 42, wherein the electric field strength is about 2000 V/cm.

Aspect 47. The method of any of the preceding aspects, wherein the electric field is applied as from 1 pulse to 100 pulses for from about 500 ns to about 100 ms per pulse.

Aspect 48. The method of any of the preceding aspects, wherein the electric field is applied as from 1 pulse to 10 pulses for from about 500 ns to about 100 ms per pulse.

Aspect 49. The method of aspect 47 or 48, wherein the electric field is applied as from 1 pulse to 100 pulses for from about 1 μs to about 10 μs.

Aspect 50. The method of any of the preceding aspects, wherein the electric field is applied as a square waveform, triangle waveform, trapezoidal waveform, bipolar pulse, a sinusoidal pulse, a continuous electric field, or any combination thereof.

Aspect 51. The method of any of aspects 1-50, wherein applying the electric field causes the at least one cell to undergo a shape change.

Aspect 52. The method of aspect 51, wherein the shape change comprises rounding, membrane blebbing, cytoskeletal reorganization, or any combination thereof.

Aspect 53. The method of aspect 52, wherein cytoskeletal reorganization comprises actin reorganization, microtubule reorganization, or any combination thereof.

Aspect 54. The method of any of aspects 1-53, wherein removing the electric field causes the at least one cell to return to the initial shape.

Aspect 55. The method of any of aspects 1-53, wherein removing the electric field does not cause the at least one cell to return to the initial shape.

Aspect 56. The method of any of aspects 1-55, wherein the method further comprises controlling cell force response.

Aspect 57. The method of aspect 56, wherein actin fibers in the at least one cell adhering to the nanofiber array at focal adhesions enables measurement of cell force response.

Aspect 58. The method of aspect 56 or 57, wherein cell force response is measured using nanonet force microscopy.

Aspect 59. The method of any of aspects 56-58, wherein applying the electric field causes a characteristic cell force response profile.

Aspect 60. The method of aspect 59, wherein the characteristic cell force response profile comprises a drop in cell force and a recovery stage.

Aspect 61. The method of aspect 60, wherein during the recovery stage, cell force response increases to from about 90% to about 110% of the initial cell force response.

Aspect 62. The method of any of aspects 56-61, wherein cell force response is exerted by cells, felt by cells, or any combination thereof.

Aspect 63. The method of any of aspects 1-62, wherein the initial shape comprises an initial cell length.

Aspect 64. The method of aspect 63, wherein the initial cell length is about 100 μm.

Aspect 65. The method of aspect 63 or 64, wherein applying the electric field causes the at least one cell to adopt a second length.

Aspect 66. The method of aspect 65, wherein during the time lag stage, the second length is from about 50% to about 75% of than the initial length Aspect 67. The method of aspect 65 or 66, wherein the second length is from about 25 μm to about 50 μm during the time lag stage.

Aspect 68. The method of aspect 67, wherein during the recovery stage, the second length is from about 90% to about 110% of the initial length.

Aspect 69. The method of aspect 65 or 68, wherein the second length is from about 90 μm to about 110 μm during the recovery stage.

Aspect 70. The method of any of aspects 1-69, wherein applying an electric field increases membrane permeability of the at least one cell relative to an initial state of membrane permeability.

Aspect 71. The method of aspect 70, wherein the cells return to the initial state of membrane permeability following removal of the electric field.

Aspect 72. The method of aspect 70 or 71, wherein assessing membrane permeability comprises (i) visualizing the at least one cell a first time, (ii) contacting the at least one cell with a membrane-impermeant stain, (iii) visualizing the at least one cell a second time, and (iv) quantifying a difference in images produced by steps (i) and (iii).

Aspect 73. The method of aspect 72, wherein the at least one cell is visualized by fluorescence microscopy, brightfield microscopy, or a combination thereof.

Aspect 74. The method of aspect 72 or 73, wherein the membrane-impermeant stain comprises propidium iodide, a modified green fluorescent propidium iodide, or any combination thereof.

Aspect 75. The method of any of aspects 72-74, wherein visualizing the at least one cell a second time results in an increased signal compared to visualizing the cells a first time.

Aspect 76. The method of aspect 75, wherein the increased signal correlates with increased membrane permeability.

Aspect 77. The method of any of aspects 72-74, wherein visualizing the at least one cell a second time results in a decreased signal compared to visualizing the at least one cell a first time.

Aspect 78. The method of aspect 77, wherein the decreased signal correlates with decreased membrane permeability or a return to the initial state of membrane permeability.

Aspect 79. The method of any of aspects 72-78, wherein membrane permeability increases within 10 seconds of applying the electric field.

Aspect 80. The method of any of aspects 72-79, wherein membrane permeability returns to the initial state within 30 minutes of removing the electric field.

Aspect 81. The method of any of the preceding aspects, wherein the method is conducted in a low-conductivity medium.

Aspect 82. The method of any of the preceding aspects, wherein the method is conducted in a calcium-free medium.

Aspect 83. The method of any of the preceding aspects, wherein the method is conducted in the presence of at least one compound that affects cellular properties.

Aspect 84. The method of aspect 83, wherein the at least one compound that affects cellular properties comprises a cytochalasin, lactrunculin, jasplakinolide, colchicine, demecolcine, nocodazole, paclitaxel, vinblastine, blebbistatin, W-7 hydrochloride, rho inhibitor I, CCG-1423, NSC 23766, ML 141, CPYPP, LY294002, PF573,228, PF431,396, fasudil, ripasudil, netarsudil, RKI-1447, Y-27632, GSK429286A, Y-30141, or a combination thereof.

Aspect 85. A method for introducing a compound into at least one cell, the method comprising (i) performing the method of any of aspects 72-84 and (ii) exposing the cell to the compound.

Aspect 86. The method of aspect 85, wherein the compound comprises nucleic acids, a vector, a peptide or protein, a membrane-impermeant stain, a pharmaceutical compound, a cryoprotectant, one or more exogenous organelles, a molecular probe, nanodevices, nanoparticles, or any combination thereof.

Aspect 87. The method of aspect 85 or 86, wherein the compound is delivered to the cytoplasm, the nucleus, or a combination thereof.

Aspect 88. The method of any of the preceding aspects, wherein the at least one cell is mechanically stressed prior to performing the method.

Aspect 89. The method of any of the preceding aspects, wherein the at least one cell is mechanically stressed while performing the method.

Aspect 90. A cell produced by the method of any of the preceding aspects.

Aspect 91. The cell of aspect 90, wherein the cell is viable following applying the electric field.

Aspect 92. The cell of aspect 90, wherein the cell is not viable following applying the electric field.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Device Fabrication and Fiber Deposition

Scaffold bases consisting of a hollow square region (see FIGS. 1A-1F). Outer scaffold dimensions: 8×8 mm; inner region: 3×3 mm) were laser cut from ~250 μm-thick polystyrene coverslips (Fisher Scientific). Using a previously reported non-electrospinning Spinneret based Tunable Engineered Parameters (STEP) technique, force-sensing nanofiber networks were fabricated consisting of a horizontal array of densely-spaced (inter-fiber spacing: 14.5±0.7 μm) small diameter (~250 nm, 233±4 nm) nanofibers deposited on a vertical array of widely-spaced (inter-fiber spacing: 279±9 μm) large diameter (diameter ~2 μm, 1.92±0.11 μm) support fibers. Fiber networks were fused at their junctions. Fiber networks were fused at their junctions using a custom fusing chamber. The 250 nm-diameter fibers were prepared using a 7 wt % solution of polystyrene (MW: 2,000,000 g/mol; Category No. 829; Scientific Polymer Products, Ontario, NY, USA) in p-xylene (X5-500; Thermo Fisher Scientific, Waltham, MA, USA), while a 2 wt % solution (Polystyrene MW: 15,000,000 g/mol; Category No. PL2014-9001, Agilent Technologies, Santa Clara, CA, USA) was used for the large, 2 μm support fibers. Individual fiber diameter and inter-fiber spacing were confirmed via Scanning Electron Microscopy (SEM) images. Mechanical properties of the fibers are listed in Table 1.

TABLE 1

Mechanical Properties of Polystyrene Fibers for Force Calculation

| Property | Value |
|---|---|
| Length (μm) | 275 |
| Diameter (nm) | 250 |

TABLE 1-continued

Mechanical Properties of Polystyrene Fibers for Force Calculation

| Property | Value |
|---|---|
| Young's Modulus (GPa) [1] | 0.97 |
| Pre-Tension (nN) [1] | 201.2 |

A single channel in polydimethylsiloxane (PDMS) was bonded to a glass coverslip to contain a plastic scaffold placed between two electrodes spaced 1-cm apart. A master mold for the PDMS channel was fabricated on a glass slide using acrylic. A 1/16" acrylic sheet was laser-cut to form the channel region (30×10×1.6 mm), and epoxied onto the glass slide. Acrylic walls surrounding the channel region were laser cut from 3/16" acrylic and epoxied in place. PDMS was mixed in 10:1 (wt/wt) base to cross-linker, degassed, and cast-molded using the master mold. After curing at 80° C. for 2-3 hours, the PDMS was removed from the mold and inlet and outlet holes were punched with at 0.75 mm biopsy punch. Before bonding to a glass cover slip, high-vacuum grease (Dow Corning, Midland, MI) was used to tack the scaffold in place on the glass slide. Bonding of the PDMS to the cover slip was achieved using a plasma cleaner (Harrick Plasma). To complete the device assembly, stainless steel acupuncture needles (diameter 0.18 mm) were carefully inserted through the device at a spacing of 1 cm and epoxied in place. The assembled device was placed under vacuum until use.

Example 2: Cell Culture and Experimental Procedure

The glioblastoma cell line U251 (ATCC) was cultured according to standard practices in growth media consisting of Dulbecco's Modified Eagle Media (DMEM) with L-Glutamine, 4.5 g/L Glucose and Sodium Pyruvate (Corning) supplemented with 10% Fetal Bovine Serum (FBS, R&D Systems) and 1% Penicillin Streptomycin (Gibco). Growth media had a conductivity of 12.8 mS/cm, an osmolarity of 355 mOsm, and contained 1.95 mM calcium. U251 cells tested negative for mycoplasma. Cells were passaged at 70-90% confluency. Both C2C12 mouse myoblasts (ATCC) and HeLa cells (kindly provided by Dr. Jennifer DeLuca, Colorado State University) were cultured in growth media consisting of DMEM with L-Glutamine, 4.5 g/L Glucose and Sodium Pyruvate (Corning) supplemented with 10% Fetal Bovine Serum (FBS, R&D Systems). VAMT (mesothelioma cell line kindly provided by Dr. Emil Lou, University of Minnesota Twin Cities) cells were cultured in RPMI 1640 medium supplemented with 10% Fetal Bovine Serum (FBS, R&D Systems). Chinese Hamster Ovary (CHO-K1, ATCC) cells were cultured in growth media consisting of DMEM/F12 (Dulbecco's Modified Eagle Medium: Nutrient Mixture F-12, Thermo Fischer Scientific) supplemented with 10% Fetal Bovine Serum (FBS, R&D Systems). B57 thyroid cancer cells (isolated from young mouse tumors and kindly provided by Dr. Aime Franco, Children's Hospital of Philadelphia) were cultured in F12 medium (Ham's F-12 Nutrient Mixture, Thermo Fischer Scientific) supplemented with 10% Fetal Bovine Serum (FBS, R&D Systems).

Figure 9A:
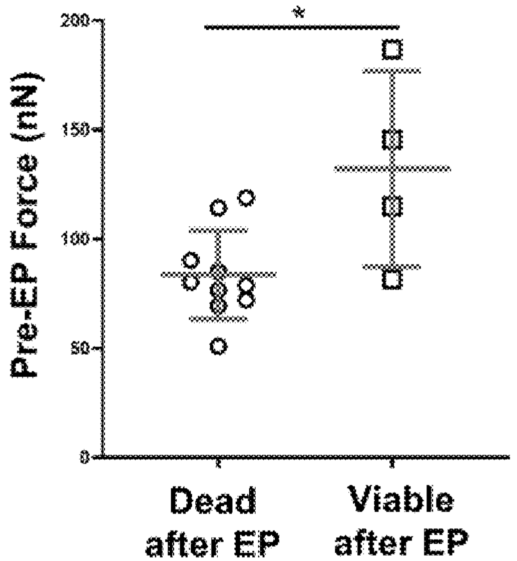
FIGS. 9A-9F show additional analysis of cell death, cell volume and device Joule heating.
Figure 9B:
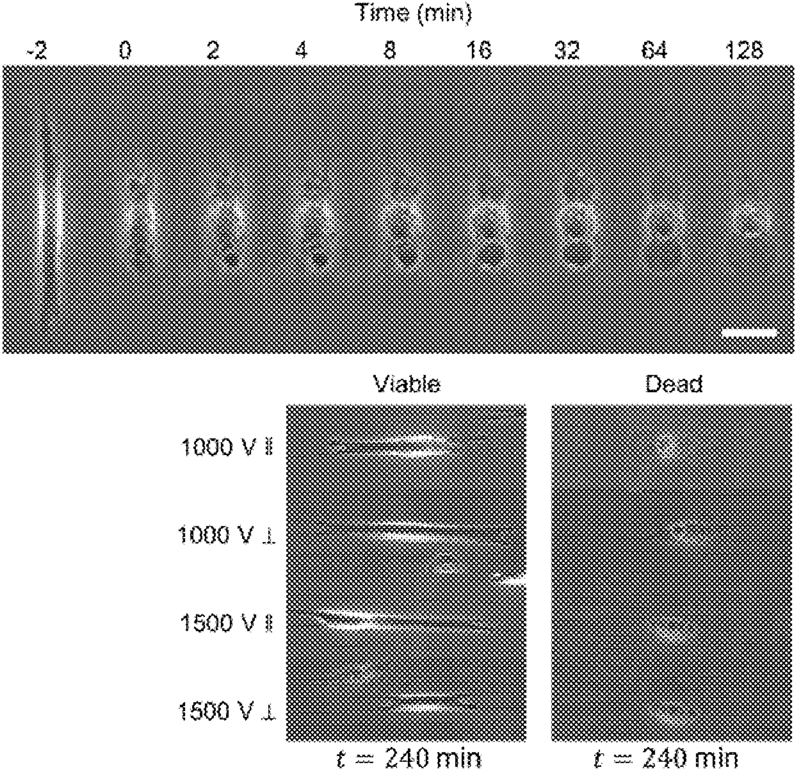
Figure 9C:
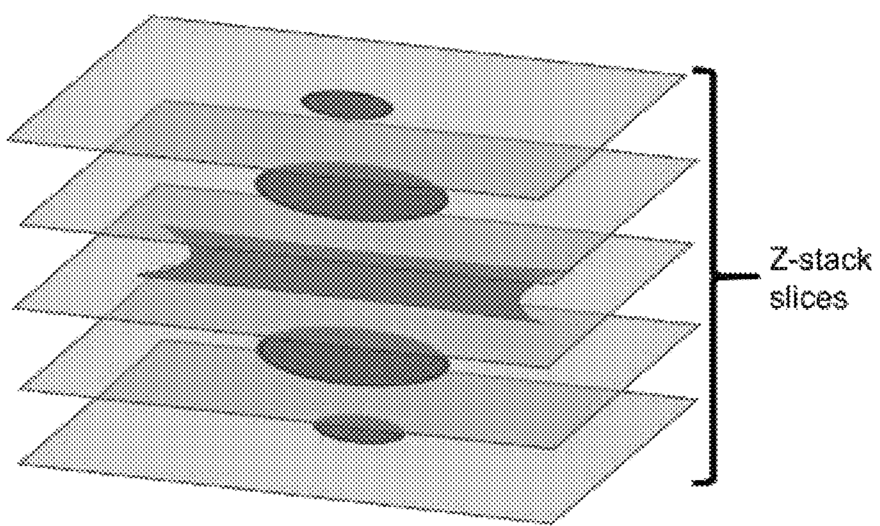
Figure 9C:
Figure 9D:
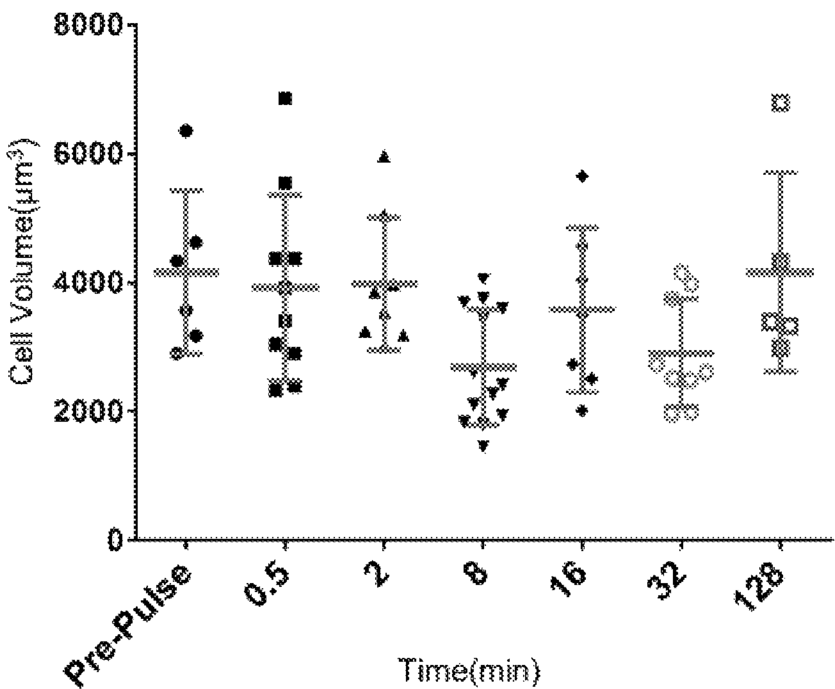
Figure 9E:
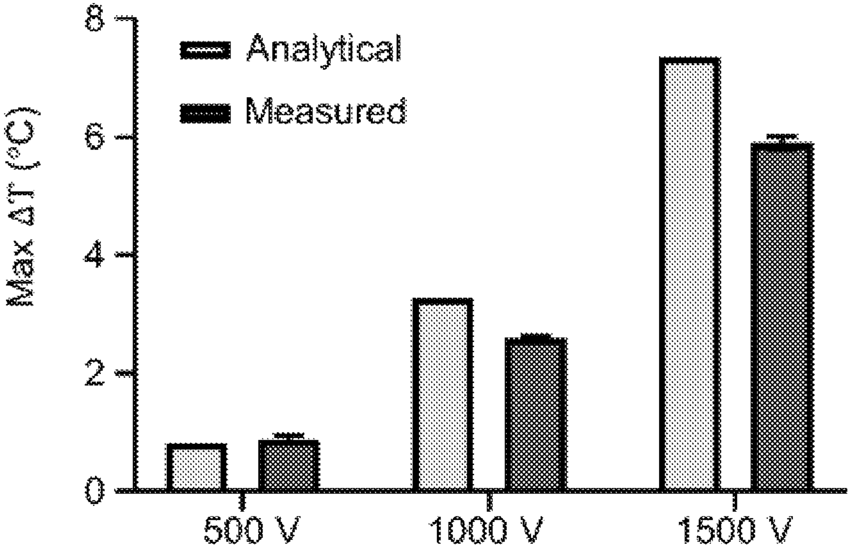
Figure 9F:
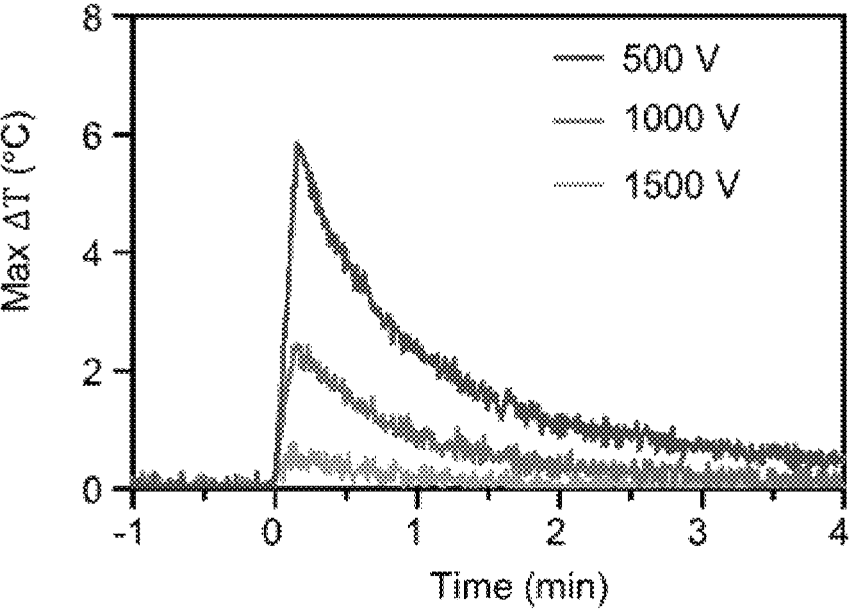

To prepare a device, the device was sterilized with ethanol, washed with PBS, and incubated for 45 minutes with 4 μg/ml Fibronectin in PBS. Cells were trypsinized, centrifuged at 150×g for 5 minutes, and resuspended in media at $0.1\times10^6$ cells/ml. Cells in suspension were added to the device and incubated at 37° C. and 5% $CO_2$ for 20-40 minutes. The device was then transferred to the microscope and incubated for 2 hours at 30° C. and 5% $CO_2$ before data collection. Contractile force experiments were performed on a Zeiss microscope (Zeiss AxioObserver Z1) with an incubation chamber maintaining a 30° C. and 5% $CO_2$ environment throughout the entirety of the experiments. The incubation temperature was decreased from standard 37° C. incubation to 30° C. to remove the potential of thermal damage caused by Joule heating during pulsing (FIGS. 9E-9F). Brightfield data was captured at 20× (phase objective, 0.8 NA) at intervals of 2 minutes. For each experiment, approximately 25 to 50 locations on the fiber network were imaged every 2 minutes. Imaging locations frequently contained more than one cell. For U251 experiments, twenty minutes of baseline data were collected before electroporation and cells were maintained in growth media for the duration of the experiment. For experiments with additional cell types, ten minutes of baseline data were collected, and cells were maintained in DMEM growth media (U251 media) for the duration of the experiment. Cell types not cultured in DMEM growth media were flushed with DMEM growth media approximately 20 minutes before beginning experiments.

To prepare cells for treatment in calcium-free DMEM, cells were seeded in complete growth media and allowed to adhere and spread on the fibers for at least 2 hours under incubation at 37° C. and 5% $CO_2$. After incubation, devices were removed from the incubator and flushed thoroughly (2×, each flush with 2× device volume) with calcium-free DMEM (DMEM with 4.5 g/L Glucose and without L-Glutamine, Sodium Pyruvate, Calcium Chloride. Gibco, 21068-028). Residual calcium was not chelated to prevent alterations in cell morphology. The device was then immediately placed on the microscope, incubated at 30° C. and 5% $CO_2$ as in the other experiments. A brief acclimation period of approximately 20 minutes was given prior to data collection. Baseline (pre-electroporation) images were acquired for 10 minutes before applying the electroporation pulses. Cells were maintained in calcium-free DMEM for the duration of the experiment.

Example 3: Sample Size and Inclusion Criteria

We analyzed U251 cells from three independent experiments for each voltage (500 V, 1000 V, 1500 V) and orientation (||, ⊥) condition. Table 2 presents the number of cells analyzed for the force analysis from each independent experiment. For each voltage and orientation tested, three independent experiments were conducted, with 20 or more total cells analyzed where possible. Ultra-low viability for the 1500 V ⊥ condition limited sample number. Cells selected for analysis were well-centered on the fibers (for the duration of the experiment), had no interference from other cells, were adhered to nanofibers with fixed endpoints (orthogonal fibers well-fused), and showed an elongated and contractile phenotype. Three independent experiments were performed the 1000 V || condition in calcium-free DMEM and analyzed the response of 24 cells. Additionally, a control ("sham") experiment was performed (FIG. 8F). For force analysis on additional cell types presented in FIGS. 6A-6C, ≥8 cells were analyzed from a single experiment for each cell type. C2C12 cells were electroporated at 2000 V due to their greater resistance to against electroporation effects.

TABLE 2

| Sample Size for Force Analysis of U251 Cells | | | | |
|---|---|---|---|---|
| | Number of cells analyzed per independent experiment | | | Total Cells |
| Condition | Exp1 | Exp2 | Exp3 | Analyzed |
| 500 V ∥ | 6 | 6 | 9 | 21 |
| 1000 V ∥ | 9 | 6 | 11 | 26 |
| 1500 V ∥ | 9 | 11 | 8 | 28 |
| 500 V ⊥ | 7 | 7 | 9 | 23 |
| 1000 V ⊥ | 8 | 6 | 8 | 22 |
| 1500 V ⊥ | 0* | 0* | 4 | 4 |
| 1000 V ∥ $Ca^{+2}$-free | 13 | 7 | 4 | 24 |
| Control (Sham) | 8 | 5 | — | 13 |

*No cells viable for analysis

Viability of U251 cells post-electroporation was analyzed from at least three independent experiments for each voltage (500 V, 1000 V, 1500 V) and orientation (∥, ⊥, 2D Flat). Table 3 presents the number for cells analyzed for each independent experiment. Viability was assessed 180 minutes post-electroporation for 500 V experiments and 240 minutes post-electroporation for 1000 V and 1500 V experiments. (Note, 2D Flat data were collected from experiments investigating the ⊥ or ∥ orientations.)

High-resolution brightfield data of individual cells enabled us to assess viability without the need for conventional live/dead staining. Viability was assessed at the single-cell level from brightfield data based on several criteria. Cells considered viable had (visually) intact membranes, had re-spread on the fibers, and were able to apply contractile forces to the fibers (i.e. deflected parallel nanofibers). Cells considered "dead" did not have (visually) intact membranes (cell lysis), did not re-spread on the fibers, and did not apply contractile forces (no fiber deflections). Using these criteria, cells considered "viable" were very distinct from cells considered "dead." FIGS. 9A-9F show several examples of "viable" vs "dead" cells. As shown in this figure, cell death generally occurred immediately following electroporation, suggesting necrosis (accidental cell death). For all experiments, all cells elongated between two parallel fibers with the characteristic elongated shape shown in FIG. 1C were included in the viability analysis.

TABLE 3

| Sample Size for Viability Analysis | | | | | | | | |
|---|---|---|---|---|---|---|---|---|
| | Number of cells analyzed per independent experiment | | | | | | | Total Cells |
| Condition | Exp1 | Exp2 | Exp3 | Exp4 | Exp5 | Exp6 | Exp 7 | analyzed |
| 500 V ∥ | 66 | 55 | 112 | — | — | — | — | 223 |
| 500 V ⊥ | 68 | 25 | 37 | 26 | 25 | — | — | 181 |
| 500 V 2D Flat | 34 | 26 | 32 | 103 | — | — | — | 195 |
| 1000 V ∥ | 60 | 62 | 60 | 33 | 27 | 48 | 126 | 416 |
| 1000 V ⊥ | 39 | 45 | 93 | 21 | — | — | — | 198 |
| 1000 V 2D Flat | 37 | 23 | 42 | — | — | — | — | 102 |
| 1500 V ∥ | 101 | 65 | 71 | — | — | — | — | 237 |
| 1500 V ⊥ | 33 | 74 | 201 | — | — | — | — | 308 |
| 1500 V 2D Flat | 15 | 24 | 20 | 93 | 48 | 126 | — | 326 |

Example 4: Electroporation Parameters

Cells were electroporated with a high voltage pulse generator (BTX ECM 830, Harvard Apparatus). Ten, 100 μs square-wave pulses were delivered at 500 V, 1000 V, or 1500 V to the device electrodes. Pulses were delivered at a frequency of 1 Hz. Measured current and voltage waveforms approximated ideal square waves (FIGS. 7A-7B). Voltage waveforms were not affected by pulse number. Current increased slightly with pulse number due to Joule heating. Finite Element modeling of the electric field within the device indicated that at applied voltages of 500 V, 1000 V, and 1500 V, the cells within the scaffold region-of-interest (cut-out region of scaffold, 250 μm from edges) experienced electric field magnitudes of 441±12 V $cm^{-1}$, 882±23 V $cm^{-1}$, and 1323±35 V $cm^{-1}$ respectively for the parallel orientation, and 455±12 V $cm^{-1}$, 911±24 V $cm^{-1}$, and 1366±36 V $cm^{-1}$ respectively for the perpendicular orientation. See the Finite Element Modeling subsection for model details and electric field magnitudes of cells in the 2D Flat configuration.

Pulse application resulted in micron-diameter bubble formation on both electrodes, but did not result in electrical arcing. Undesired electrochemical effects were minimized via low surface area electrodes (diameter 0.18 mm), a large volume of fluid outside the electrode region (~2.5 times the volume of fluid between the electrodes), and locating the fiber network region several millimeters away from both electrodes. Media pH was minimally affected by electroporation (Sham: 7.11±0.06; 1500 V: 7.16±0.06. pH measured 3 hours after electroporation).

Example 5: Immunostaining and Confocal Microscopy

Some cells were fixed and stained for actin, paxillin, and microtubules according to standard practices. YO-PRO-1 and Propidium Iodide (PI), both membrane-impermeant dyes, were used to confirm membrane disruption and show permeability distribution. Cells were fixed with 10% Formalin for 10 minutes, permeabilized with 0.1% Triton-X 100 in PBS for 15 minutes, and blocked with 5% goat serum in PBS for 30 minutes. Focal adhesion antibody (Paxillin, TYR31) (5 μg/ml) and microtubule antibody (beta tubulin) (1 μg/ml) were prepared in an antibody dilution buffer (PBS with 10 mg/ml BSA and 1 μl/ml Triton X-100) and were added to the cells and incubated at room temperature for three hours. The device was washed with PBS and antibody dilution buffer supplemented with actin stain (rhodamine phalloidin, sc-301530; Santa Cruz Biotechnology, Dallas, TX, USA) diluted in a 1:80 ratio and secondary antibodies (Alexa Fluor 488 Goat Antibody (Green), Alexa Fluor 647 Goat Antibody (Cyan) both 5 μg/ml) were added for 45 minutes at room temperature while protected from light. The device was then washed with PBS and 3 nM DAPI diluted in PBS was added to the device for 5 minutes in the dark. The device was then washed with PBS and imaged using a 63× (1.15 NA) water-immersion objective on a confocal microscope (Zeiss LSM 880). The z-slice thickness was kept at either 0.36 μm or 0.5 μm.

Cell volume calculations were performed in MATLAB from z-stacks of fluorescent images (stained for actin, microtubules, and the nucleus) of fixed cells at various time points (pre-pulse, 0.5, 2, 8, 16, 32, and 128-minutes) after electroporation. (n=6, 10, 8, 13, 7, 9 and 5 cells corresponding to pre-pulse, 0.5, 2, 8, 16, 32, and 128-minute timepoints respectively.) Cells were imaged with a 63×1.15 NA water immersion objective on a confocal microscope (Zeiss LSM 880). In MATLAB, images were converted into grayscale and subsequently binarized using a custom MATLAB routine to calculate the projected cell area as shown in FIG. 9C. Cell volume was calculated as volume=Σ(projected cell area)*z-slice thickness.

Bleb analysis was performed in ImageJ. Bleb area was measured on the z-slice corresponding to the bleb's greatest diameter (n=82, 126, 214, 131 and 23 blebs from 12, 12, 13, 11 and 4 cells for 0.5, 2, 8, 16 and 32-minute timepoints respectively). A membrane roughness ratio (FIG. 4E) was used to quantify the increased length of the cell contour along the nanofiber due to the presence of blebs, and was measured as the ratio of the contour length to the cell end-to-end length (n=6, 14, 16, 9, 10 and 6 for −2 (pre-pulse), 0.5, 2, 8, 16 and 32-minute timepoints respectively). Non-electroporated cells demonstrated negligible blebbing and thus had a roughness ratio very close to 1. Bleb analysis for calcium-free experiments (FIGS. 11A-11B) followed the same procedure, however brightfield images were used to calculate the roughness ratio.

Example 6: Membrane Permeability Imaging

To experimentally confirm membrane disruption by electroporation, YO-PRO-1 and Propidium Iodide (PI) were used, both membrane-impermeant dyes. Membrane disruption by electroporation was visually demonstrated by the fluorescence of the membrane-impermeant dye YO-PRO-1 (1000 V ∥ condition shown in FIG. 2A). For clarity in FIG. 2A, a background subtraction technique (via a gaussian-blur) was used as well as a lower intensity threshold to remove background YO-PRO-1 signal and thus these images are for illustration purposes only. Experiments were performed with 1 μl/ml (1 μM) YO-PRO-1 (Thermo Fisher Scientific) in media.

The spatial distribution of PI uptake was visualized during the first 60 seconds after electroporation at 1000 V (∥: 882 V/cm; ⊥: 911 V/cm). A high concentration of PI (0.17 mg/ml) (Fisher Scientific) was used as in similar studies to enable high frame-rate data collection (short exposure times) while maintaining strong fluorescence signal. Media containing PI was added immediately prior to imaging and electroporating the cells. Ten, 1000 V pulses were delivered at 1 Hz. Images were captured at 1.2 s intervals at 63× magnification.

Example 7: Force Calculation

Contractile force is calculated in MATLAB by comparing the deflection profile of the fiber with the best fit profile of a loaded fixed-fixed beam subjected to the cell forces at an angle, $\alpha_{Force}$, measured as the angle between the resultant force vector and the undeflected nanofiber direction. Details on force analysis formulation and numerical scheme have been published previously. The cell's applied load to the fiber is assumed to be at each endpoint of the cell's protrusions where the f-actin stress fibers are anchored to the nanofibers via focal adhesions (FIG. 1E).

The direction of the resultant force, $\alpha_{Force}$, is estimated based on physiological structures from fixed cells. Elongated cells (cell before electroporation or long after electroporation) have well defined stress fibers which are ~12.4° from the horizontal (FIG. 1E, bottom left). In instances where stress fibers are not present in recovering cells, deference is made to the angle of the dominant retraction fibers, (FIG. 1E bottom center) known for their force bearing capabilities. In cases where neither stress fibers or retraction fibers are visible, and the cell is highly rounded, the resultant angle is taken to be the bisection of the angle created by the membrane at the point of attachment to the fiber (FIG. 1E, bottom right). For these situations, mechanical forces must be applied in-line with the membrane, thus, the resultant force would be the sum of the vectors radiating outward along the membrane, resulting in half the angle formed by the membrane. For a completely spherical cell, the half angle created by the membrane would point the force vector directly to the cell centroid. Cells were fixed and their cytoskeletons imaged under no-electroporation conditions and 0.5, 2, 8, 16, 32, 128 minutes after electroporation at 1000 V ⊥. When $\alpha_{Force}$ was averaged for each cell, the plot in FIG. 1F results (n=119). When cell length (L) is less than 63.4 μm in length, the angle of force application increases, and can be approximated as linear. Minimizing error for the data results in the following best fit:

$$\alpha_{Force}(L) = \begin{cases} 12.4 + .54(63.4 - L), & L < 63.4 \\ 12.4, & L \geq 63.4 \end{cases} \quad (1)$$

Where $\alpha_{Force}$ is in degrees and L is in μm. At each timepoint during cell recovery, the cell length is computed and the corresponding force angle is an input to the finite element model.

The deflection profiles are measured by marking the fiber endpoints and eight points along the fiber length including the two endpoints of the cell. Fiber properties used in the computation of contractile force can be found in Table 1. Cell elongation was defined to be the length between a cell's endpoints on a fiber.

Example 8: Finite Element Modeling

COMSOL 5.4 was used to model the electric field distribution in the device. The AC/DC module was used to perform a steady-state simulation. Computational models of the electric field within the device are shown in FIGS. 1D and 8A-8F. At applied voltages of 500 V, 1000 V, and 1500 V, the models indicated that the scaffold region-of-interest (cut-out region of scaffold, 250 μm from edges) experienced electric field magnitudes of 441±12 V $cm^{-1}$, 882±23 V $cm^{-1}$, and 1323±35 V $cm^{-1}$ respectively for the parallel orientation, and 455±12 V $cm^{-1}$, 911±24 V $cm^{-1}$, and 1366±36 V $cm^{-1}$ respectively for the perpendicular orientation (Mean±STD). Cells on the flat experienced electric field magnitudes of 463±6 V $cm^{-1}$, 925±13 V $cm^{-1}$, and 1388±19 V $cm^{-1}$ respectively for the parallel orientation, and 449±4 V $cm^{-1}$, 897±9 V $cm^{-1}$, and 1345±13 V $cm^{-1}$ respectively for the perpendicular orientation. Scaffold rotation is the cause of the slight increase in the electric field in the perpendicular orientation.

COMSOL was used to model the induced transmembrane potential (ITP) on cells. An accurate cell volume was reconstructed using 3D Slicer from a z-stack images of a fixed, actin-stained cell. Cell volume was meshed using 3-Matic. A steady state model was performed while the effect of electroporation-induced conductivity changes to the cell membrane was neglected. Over the volume, the Laplace equation (2) was solved:

$$\nabla^2 V = 0 \quad (2)$$

where V is voltage. A contact impedance boundary condition was used to model the boundary condition across the cell membrane:

$$n \cdot J = \frac{\sigma_m}{d_m}(V - V_{ref}) \tag{3}$$

where $\sigma_m$ and $d_m$ are the conductivity and thickness of the cell membrane respectively and V and $V_{ref}$ are the voltages on either side of the cell membrane. Model parameters are presented in Table 4.

TABLE 4

Parameters for Induced Transmembrane Potential (ITP) COMSOL Model

| Parameter | Symbol | Value | Reference | Parameter |
|---|---|---|---|---|
| Extracellular media conductivity | $\sigma_e$ $(S \cdot m^{-1})$ | 1.28 | Measured | Extracellular media conductivity |
| Extracellular media relative permittivity | $\varepsilon_e$ | 80 | [2, 3] | Extracellular media relative permittivity |
| Cytoplasm conductivity | $\sigma_c$ $(S \cdot m^{-1})$ | 0.5 | [3] | Cytoplasm conductivity |
| Cytoplasm relative permittivity | $\varepsilon_c$ | 60 | [3, 4] | Cytoplasm relative permittivity |
| Cell membrane conductivity | $\sigma_m$ $(S \cdot m^{-1})$ | 3e−7 | [3] | Cell membrane conductivity |
| Cell membrane relative permittivity | $\varepsilon_{cm}$ | 8.57 | [3, 5] | Cell membrane relative permittivity |
| Cell membrane thickness | $d_m$ (nm) | 5 | a. [3] | Cell membrane thickness |

Example 9: Mitigation of Thermal Effects

We performed experiments at 30° C. to mitigate thermal effects due to Joule heating. Joule heating was determined to be no greater than 8° C. (FIGS. 9A-9F). The worst-case scenario for Joule heating was calculated by assuming that all electrical energy is immediately converted to thermal energy to cause an instantaneous temperature rise. Worst-case Joule heating was calculated for the delivery of 10 pulses at 1500 V using the equation:

$$\Delta T = IVt_{on}/(C_p m) \tag{4}$$

where ΔT is the change in temperature within the device, V is the voltage applied (measured), I is the current through the device (measured), $c_p$ is the specific heat capacity of the media (approximated as water: 4.184 kJ/(kg·K)), and m is the mass of the media being heated. Mass is calculated as m=ρlwh, where ρ is the density (approximated as water: 1 $kg/m^3$), l is distance between electrodes (1 cm), w is width of the channel (1 cm), and h is height of the channel (1.6 mm). Worst-case scenario Joule heating was expected to cause a temperature rise of less than 8° C.

Fiber optic temperature probe measurements within the device demonstrated that at the maximum electroporation condition of 10 pulses at 1500 V cm−1, temperature rise was under 7° C. (FIGS. 9A-9F). The analytical temperature rise calculation is thus in good agreement with experiments. The rapid temperature rise was quickly dissipated by the surrounding fluid in the channel, and the temperature returned to within 2° C. of the pre-treatment temperature within a few minutes.

Example 10: Fabrication of Microfluidic Chip Integrating Force-Sensing Nanofibers A custom microfluidic device was fabricated that integrates the nanofiber scaffold between two needle electrodes spaced 1 cm apart (FIG. 1A). Using the previously reported non-electrospinning STEP technique, suspended polystyrene nanofiber networks were generated: 250 nm-diameter nanofibers spaced 15 μm apart were fused to larger, 2 μm-diameter orthogonal fibers spaced 275 μm apart. Rotation of the nanofiber scaffold 90 degrees reoriented the electric field from a "parallel" configuration that aligned the electric field direction from being parallel to the nanofibers to a "perpendicular" orientation that placed the nanofibers perpendicular to the field (FIG. 1B). These orientations are referred to simply as the parallel (‖) and perpendicular (⊥) orientations. Cells elongate between adjacent nanofibers and deflect them according to the cell's inherent contractility (FIG. 1C). In this study, human glioblastoma cells were subjected (U251, ATCC) to ten, 100 μs square-wave pulses at 1 Hz delivered at 500 V, 1000 V, or 1500 V, generating approximately uniform electric fields across the scaffold region (FIGS. 1D, 7A). At applied voltages of 500 V, 1000 V, and 1500 V, these models indicated that the scaffold region-of-interest (cut-out region of scaffold, 250 μm from edges) experienced electric field magnitudes of 441±12 V $cm^{-1}$, 882±23 V $cm^{-1}$, and 1323±35 V $cm^{-1}$ respectively for the parallel orientation, and 455±12 V $cm^{-1}$, 911±24 V $cm^{-1}$, and 1366±36 V $cm^{-1}$ respectively for the perpendicular orientation. The contractile force of a cell was calculated by the deflection of the flexible nanofibers. To calculate the contractile force from fiber deflection, a deflecting nanofiber is modeled as a fixed-fixed beam with two point-source loads, $\vec{F}$, acting at the two primary adhesion sites, one at either end of the cell. The direction of the force application, $\alpha_{Force}$, was determined from the orientation of the actin stress fibers, actin-rich retraction fibers, or as specified in the Experimental section (FIG. 1E). In general, $\alpha_{Force}$ is approximately linearly-dependent on the cell length (L) for L<63.4 μm, but constant (~12.40) for L≥63.4 μm (FIG. 1F).

Figure 2A:
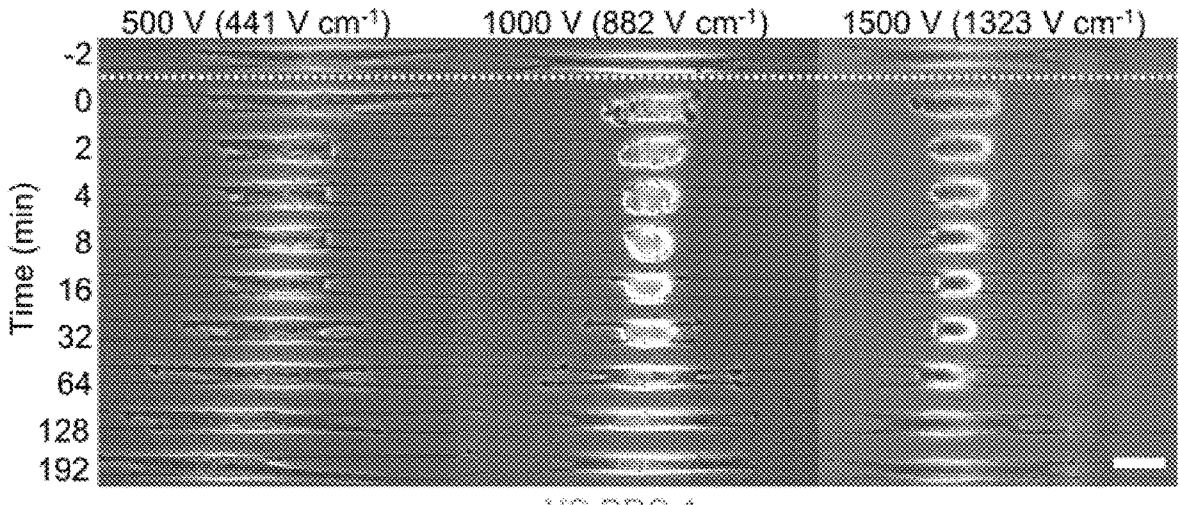
Figure 2B:
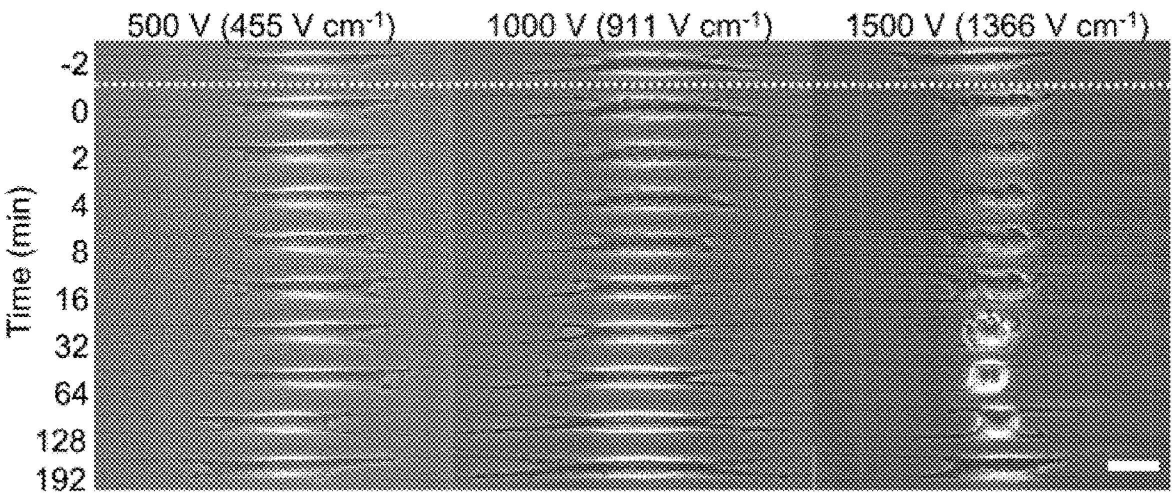
Figure 2D:
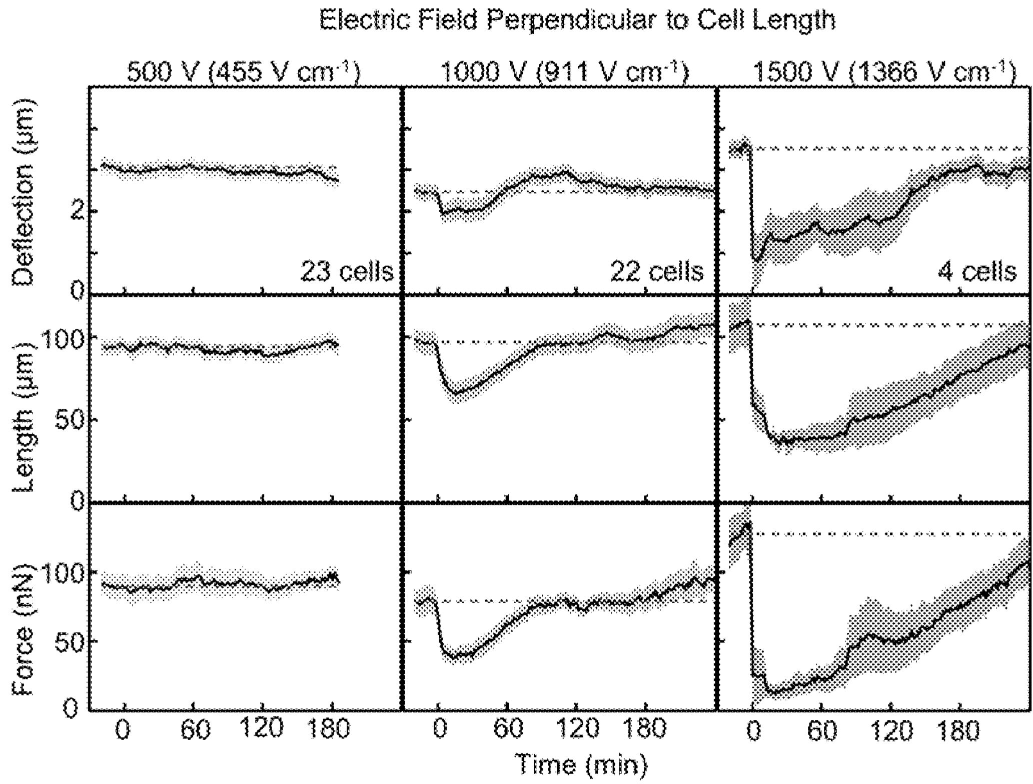

Almost immediately after electroporation, cell elongation decreased and membrane blebs formed. In the parallel orientation, cell rounding became appreciable with increasing field strengths (FIG. 2A). Interestingly, in the perpendicular orientation, cells largely retained their elongated morphology (FIG. 2B) unless the field strength was high (1500 V), which resulted in high levels of blebbing and cell rounding. Membrane blebbing decreased over a span of several minutes, after which the cells re-spread along the fibers. The temporal dynamics of the cell length, average fiber deflection (measured at cell attachment points), and contractile force response were quantified for different field strengths both in the parallel (FIG. 2C) and perpendicular orientations (FIG. 2D).

Example 11: Contractility as a Biophysical Metric of Electroporation

Figure 2E:
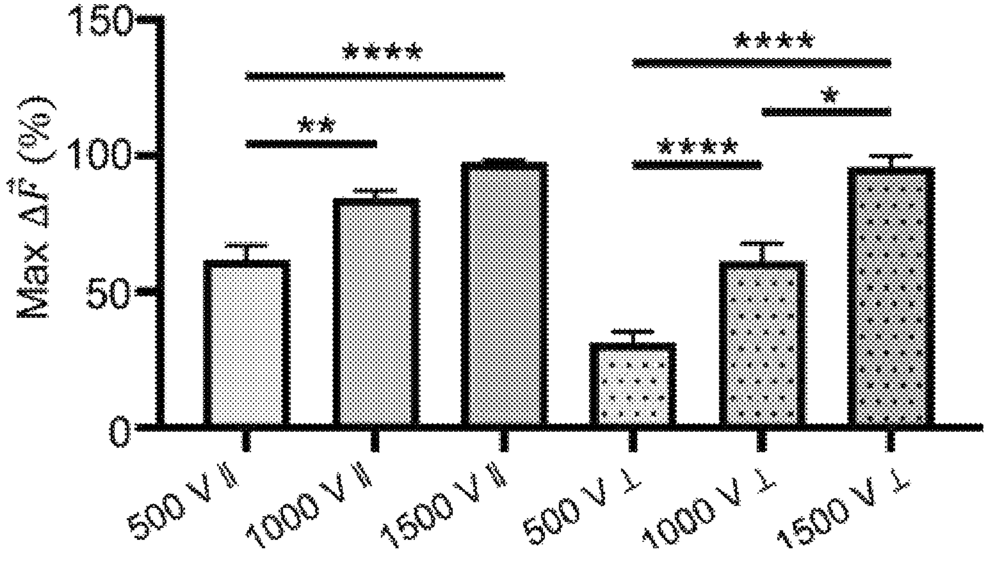
Figure 2F:
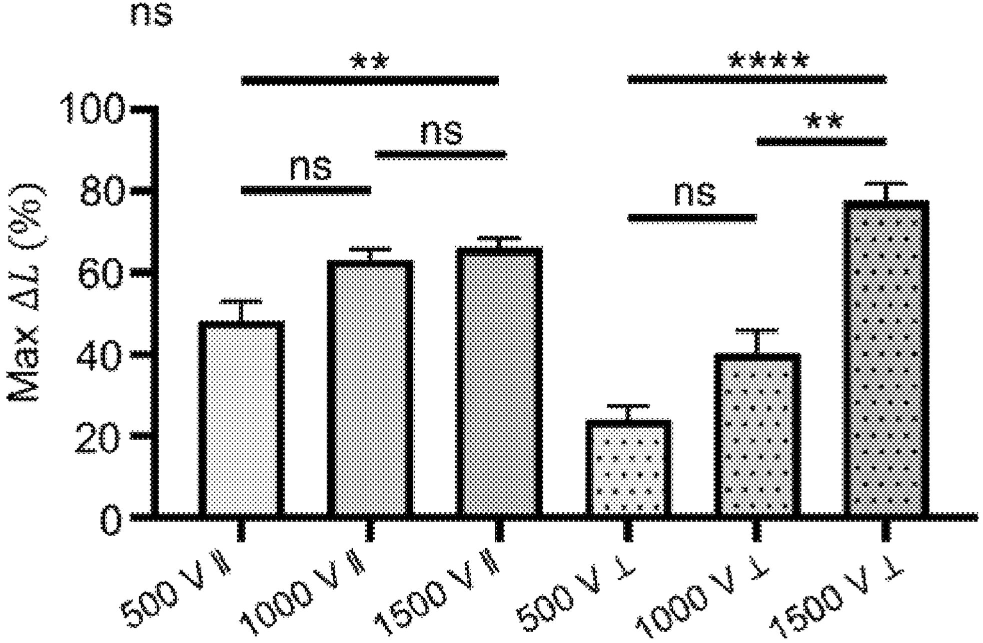

In the parallel orientation, all applied voltages immediately reduced the average contractile force, and showed complete recovery within 1-2 hours (FIG. 2C). Increasing the applied voltage caused a larger decrease in the cell force (FIG. 2E) and length (FIG. 2F). Unexpectedly, a transitory biphasic rebound was discovered in the cell contractile force immediately after the initial decrease in force post-electroporation, as indicated by the black arrows in FIG. 2C. Analysis of individual force responses in the parallel orientation reveals that a majority of the cells (50 of 75 of sampled cells, 67%) underwent a multi-stage force response, discussed in detail later in this paper.

Figure 2G:
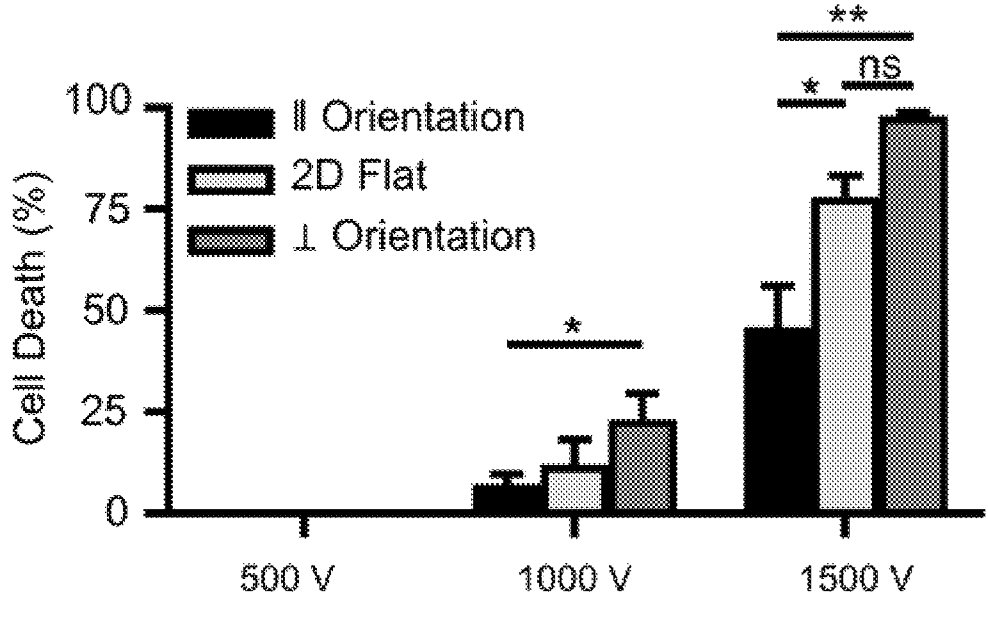

In the perpendicular orientation, higher electric fields caused a greater decrease in force (FIG. 2E) and length (FIG. 2F) after electroporation, however cell response was quite different from the parallel orientation. Contractile force and cell length did not change after electroporation of 500 V, similar to steady-state behavior observed in untreated cells (FIG. 8F). Application of 1000 V ⊥ decreased contractile force and elongation, but this decrease was smaller (FIGS. 2E, 8A, 8B), more gradual, and recovery occurred sooner than 1000 V ||. Few cells survived 1500 V ⊥, but surviving cells showed higher-than-average pre-pulse contractility (FIG. 9A), had dramatically reduced force and lengths after treatment, and had a long recovery to near pre-electroporation conditions. Interestingly, cell death (FIG. 9B) was higher for cells treated in the perpendicular orientation than in the parallel orientation (FIG. 2G, Table 5). At 1500 V, the percent cell death increased dramatically from 46±10% (|| orientation) to 98±1% (⊥ orientation). At the end of data collection post-electroporation (3-4 hours), no significant differences were found in cell length or contractile force compared to pre-electroporation values for either cell orientation (FIGS. 9C-9D).

TABLE 5

Sample Size of Cells Analyzed for Viability Response and Percent Cell Death for Each Experiment

| Condition | Ratio of dead cells to live cells (% cell death) | | | | | | | Total Cells | Percent |
|---|---|---|---|---|---|---|---|---|---|
| | Exp1 | Exp2 | Exp3 | Exp4 | Exp5 | Exp6 | Exp 7 | analyzed | cell death |
| 500 V \|\| | 0:66 (0%) | 0:55 (0%) | 0:112 (0%) | — | — | — | — | 233 | 0 ± 0% |
| 500 V ⊥ | 0:68 (0%) | 0:25 (0%) | 0:37 (0%) | 0:26 (0%) | 0:25 (0%) | — | — | 181 | 0 ± 0% |
| 500 V 2D Flat | 0:34 (0%) | 0:26 (0%) | 0:32 (0%) | 0:103 (0%) | — | — | — | 195 | 0 ± 0% |
| 1000 V \|\| | 11:49 (18%) | 2:60 (3%) | 6:54 (10%) | 0:33 (0%) | 0:27 (0%) | 4:44 (8%) | 13:113 (10%) | 416 | 7 ± 2% |
| 1000 V ⊥ | 13:26 (33%) | 11:34 (24%) | 28:65 (30%) | 1:20 (5%) | — | — | — | 198 | 23 ± 6% |
| 1000 V 2D Flat | 0:37 (0%) | 4:19 (17%) | 8:34 (19%) | — | — | — | — | 102 | 12 ± 5% |
| 1500 V \|\| | 63:38 (62%) | 18:47 (28%) | 34:37 (48%) | — | — | — | — | 237 | 46 ± 10% |
| 1500 V ⊥ | 33:0 (100%) | 72:2 (97%) | 194:7 (97%) | — | — | — | — | 237 | 98 ± 1% |
| 1500 V 2D Flat | 13:2 (87%) | 14:10 (58%) | 15:5 (75%) | 66:27 (71%) | 46:2 (96%) | 102:24 (81%) | — | 326 | 78 ± 5% |

Figure 8A:
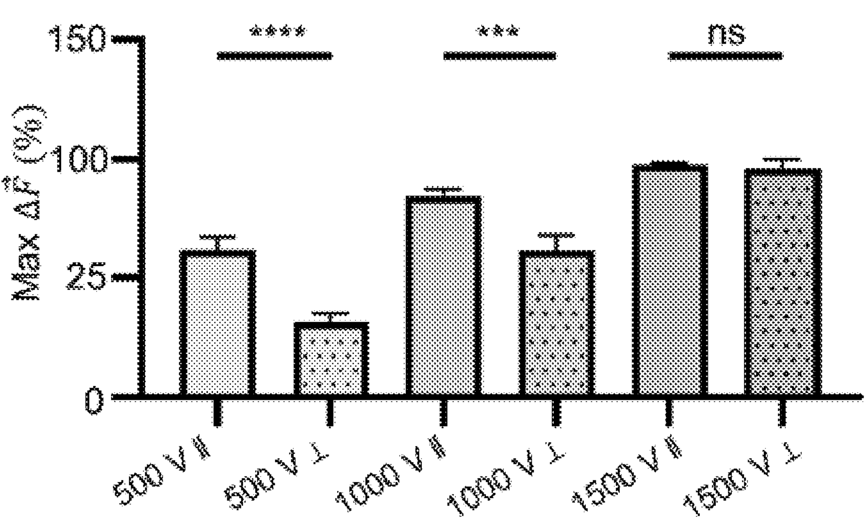
FIGS. 8A-8F show force and length changes after electroporation.
Figure 8B:
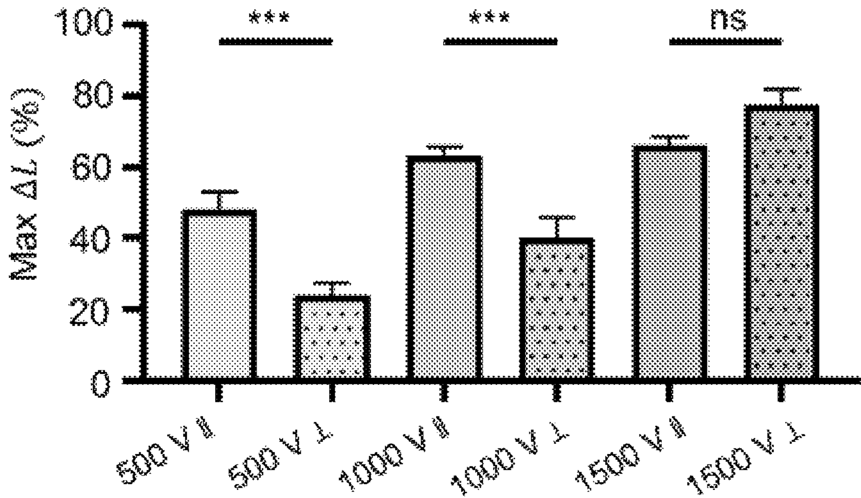
Figure 8C:
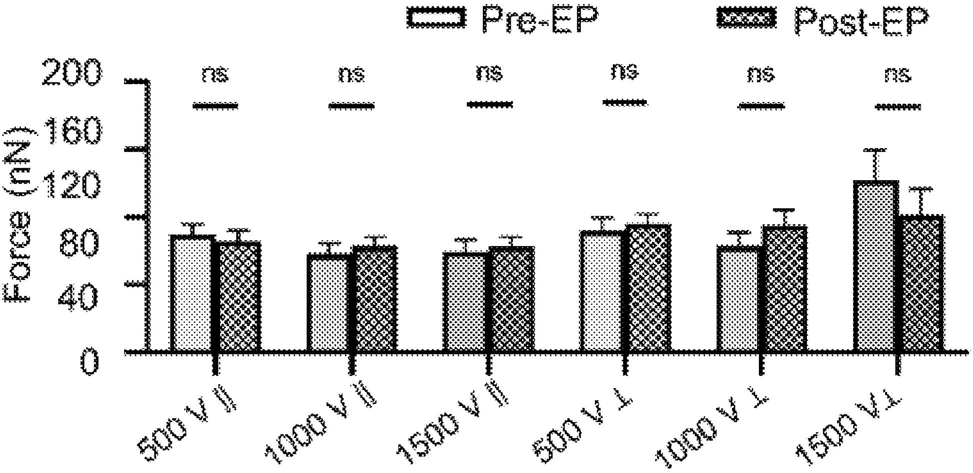
Figure 8D:
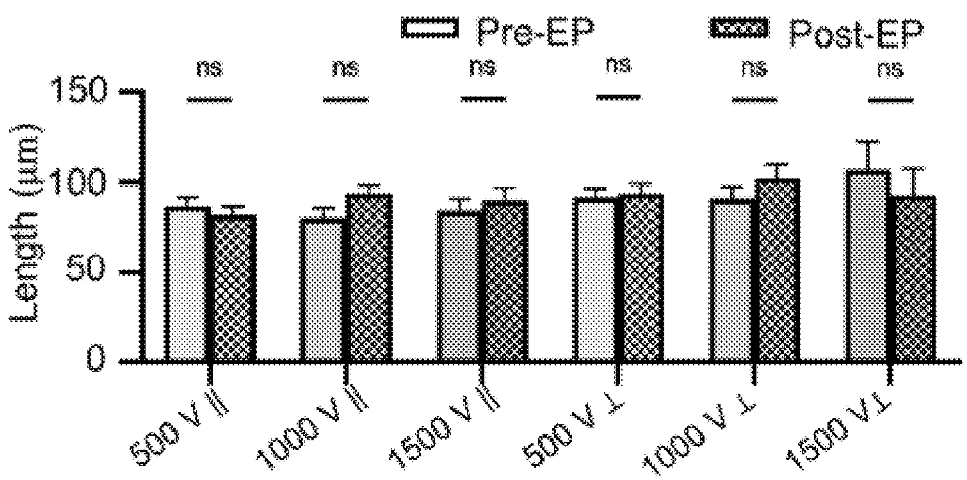
Figure 8E:
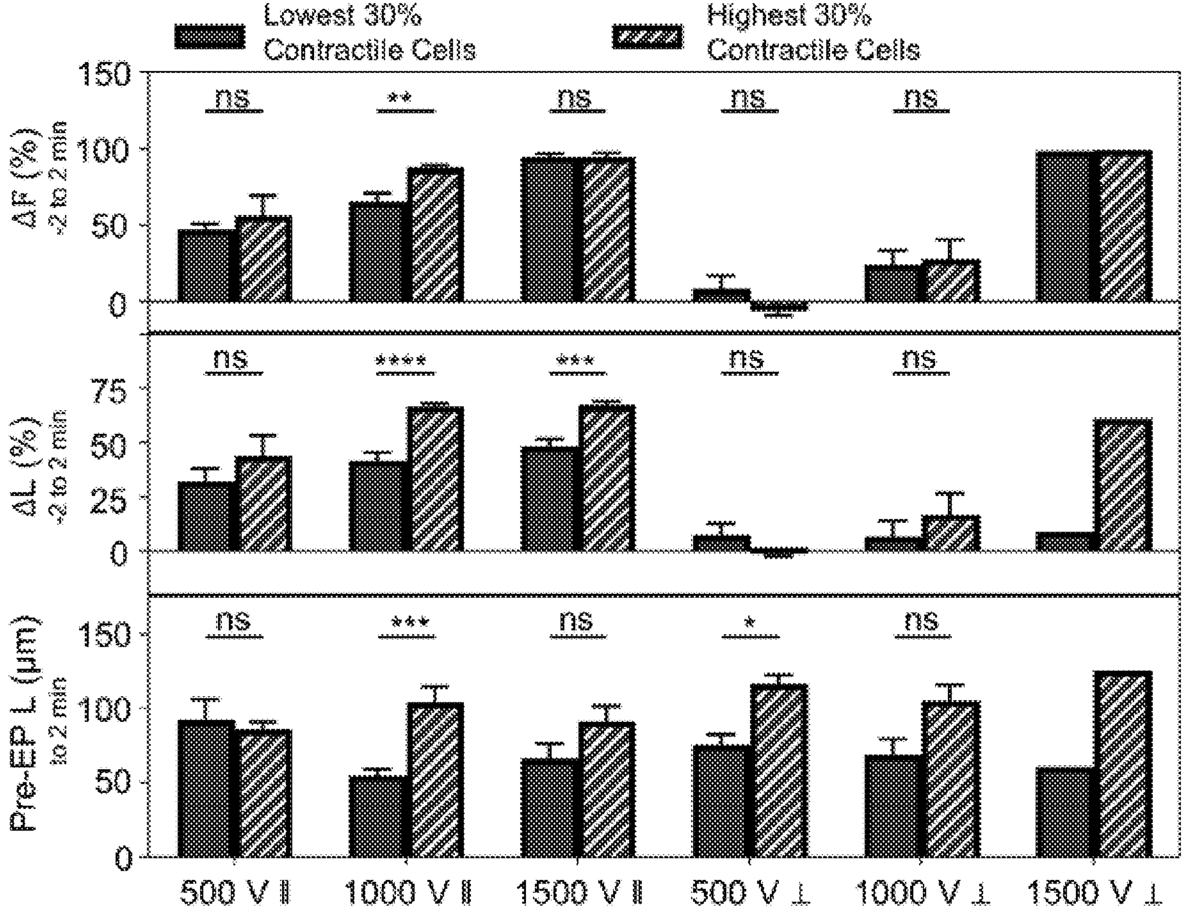
Figure 8F:
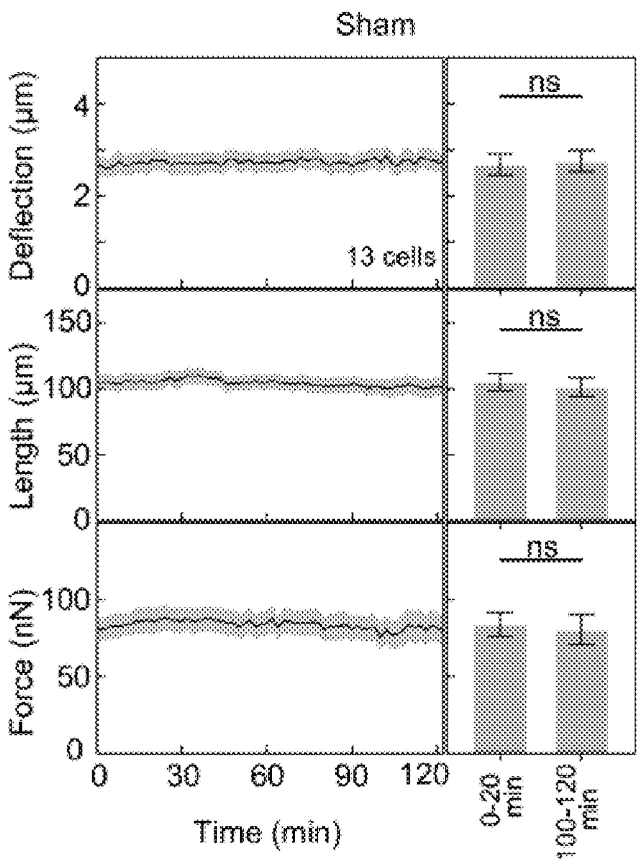

Cells post-electroporation do not show significant differences in contractile force or length compared to pre-electroporation values (FIGS. 8C-8D). Post-electroporation data collected at 180 min for 500 V and 240 min for 1000 V and 1500 V. FIG. 8E shows that, for a given voltage and field orientation, high and low contractile cells show a similar force response in the first two minutes after EP. In the parallel orientation, the high contractile cells show a larger decrease in cell length immediately after electroporation when compared with low contractile cells, suggesting that contractility might increase the rate of rounding. However, high contractile cells also tend to also have longer initial lengths, so the rate of rounding may be dependent on both cell contractility and cell length. Stats not available for 1500 V ⊥ (n=1 for both bars).

Example 12: Contractility and Multi-Stage Cell Recovery Post-Electroporation

Figure 3A:
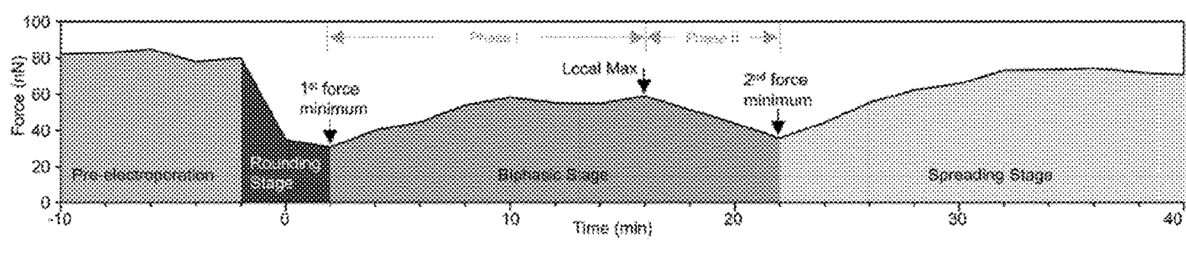
FIGS. 3A-3G shows electroporated cells show a biphasic force recovery.
Figure 3B:
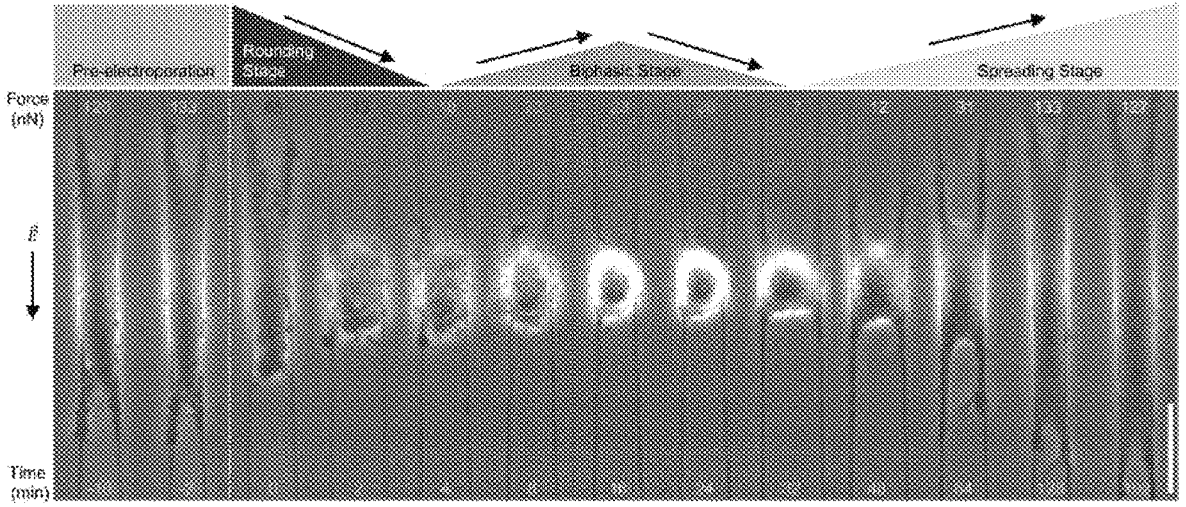
Figure 3C:
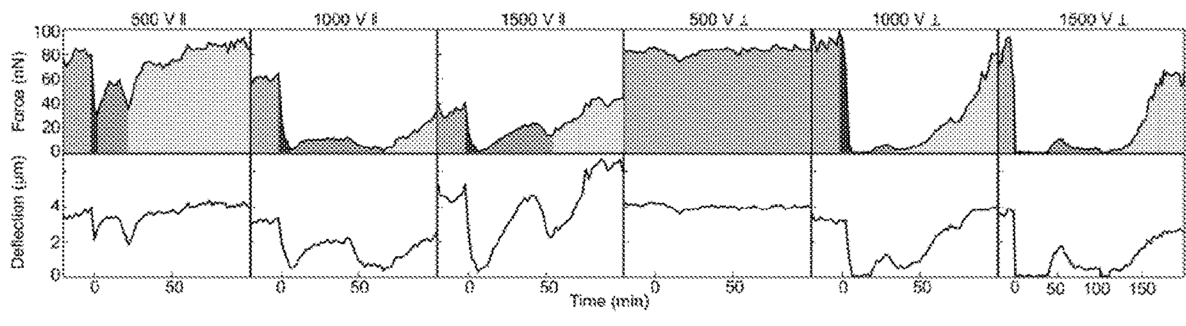

The recovery process can be divided into the following stages (FIGS. 3A-3B): a cell-rounding stage (Stage 1) of decreasing force and cell rounding, a biphasic stage (Stage 2) characterized by a transient rebound of force and subsequent relaxation, and a cell-spreading stage (Stage 3) during which the cell recovers its pre-electroporation force and length. In FIG. 3C, the multi-stage dynamics of contractile force and fiber deflection for a single cell in each treatment condition are shown. This response occurs more frequently in the parallel orientation (for example, 20 of 26 cells for 1000 V ||(77%) versus 8 of 22 cells for 1000 V ⊥ (36%)). See Table 6 for all percentages.

TABLE 6

Sample Size of Cells Analyzed for Force Response and Percentage of Cells Indicating a Biphasic Response Stage

| Condition | Number of cells analyzed per independent experiment | | | Number of cells with biphasic stage | | | Total cells with biphasic | Total Cells | Total % of cells showing biphasic |
|---|---|---|---|---|---|---|---|---|---|
| | Exp1 | Exp2 | Exp3 | Exp1 | Exp2 | Exp3 | stage | Analyzed | stage |
| 500 V \|\| | 6 | 6 | 9 | 5 | 2 | 4 | 11 | 21 | 52% |
| 1000 V \|\| | 9 | 6 | 11 | 6 | 6 | 8 | 20 | 26 | 77% |
| 1500 V \|\| | 9 | 11 | 8 | 7 | 8 | 4 | 19 | 28 | 67% |
| 500 V ⊥ | 7 | 7 | 9 | 0 | 0 | 0 | 0 | 23 | 0% |

TABLE 6-continued

Sample Size of Cells Analyzed for Force Response and Percentage of Cells Indicating a Biphasic Response Stage

| Condition | Number of cells analyzed per independent experiment Exp1 | Exp2 | Exp3 | Number of cells with biphasic stage Exp1 | Exp2 | Exp3 | Total cells with biphasic stage | Total Cells Analyzed | Total % of cells showing biphasic stage |
|---|---|---|---|---|---|---|---|---|---|
| 1000 V ⊥ | 8 | 6 | 8 | 5 | 2 | 1 | 8 | 22 | 36% |
| 1500 V ⊥ | 0* | 0* | 4 | 0 | 0 | 3 | 3 | 4 | 57% |

Figure 3D:
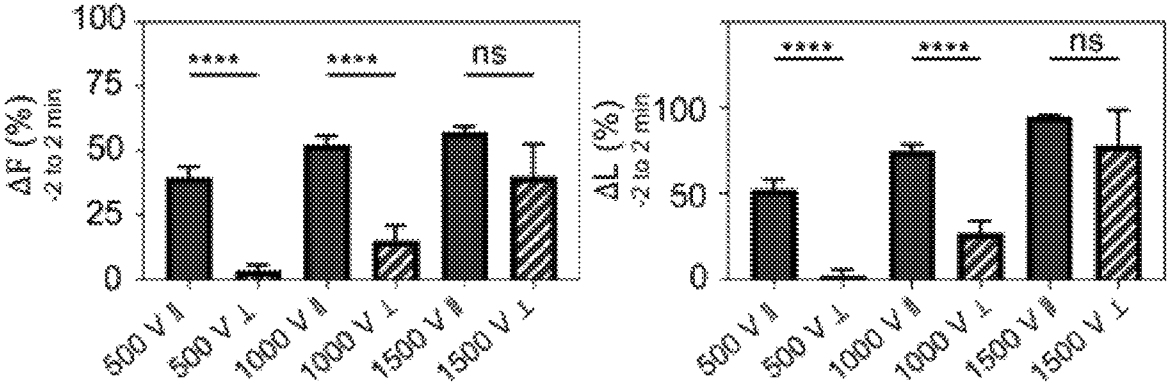

Stage 1: Recovery begins with a cell-rounding stage that typically occurs within the first 5 minutes (longer for 1500 V ⊥) after pulsing and is characterized by a rapid reduction of force. Cell extremities retract along the fibers (via actin retraction fibers (FIG. 1E)) causing rounding and membrane blebbing (FIG. 3B, t=0-2 min). At 500 V and 1000 V, cell length decreases significantly more in the parallel orientation than the perpendicular orientation during the first two minutes post-electroporation (FIG. 3D). Since calcium is known to breakdown cell focal adhesions and is also an important ion regulating cell response to electroporation, experiments were repeated in calcium-free conditions. For electroporation of 1000 V ‖ in serum-free media with no extracellular calcium, cells universally remained elongated on the fibers shortly after electroporation (FIG. 3G), in stark contrast to the ubiquitous rounding that occurred after the same electroporation conditions in standard cell culture media.

Figure 3E:
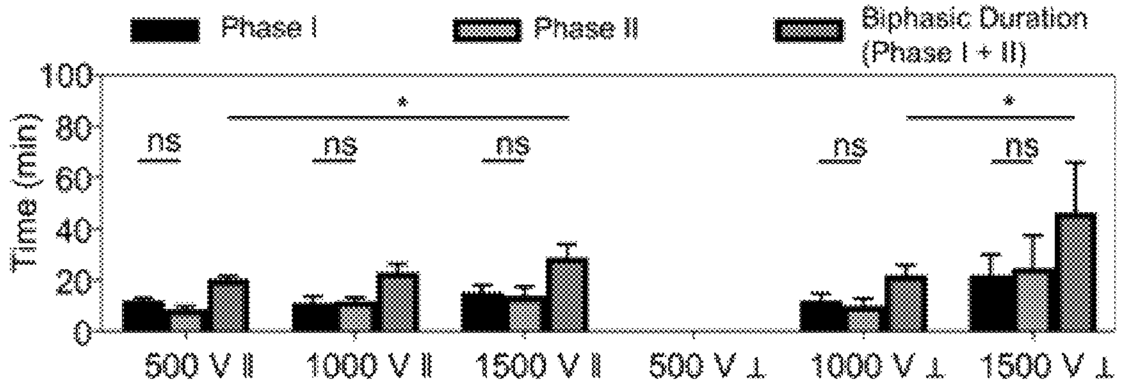
Figure 3F:
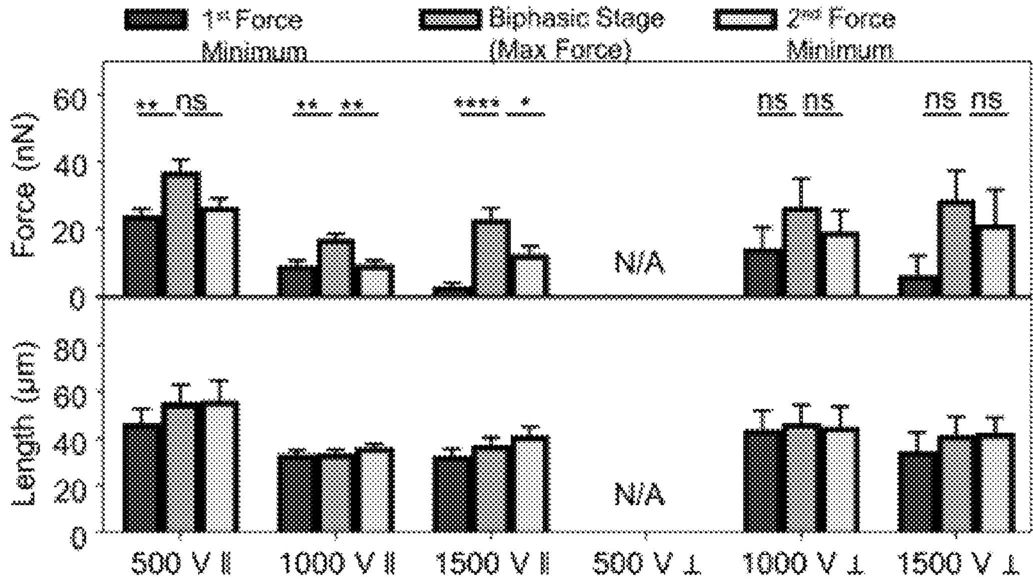
Figure 3G:
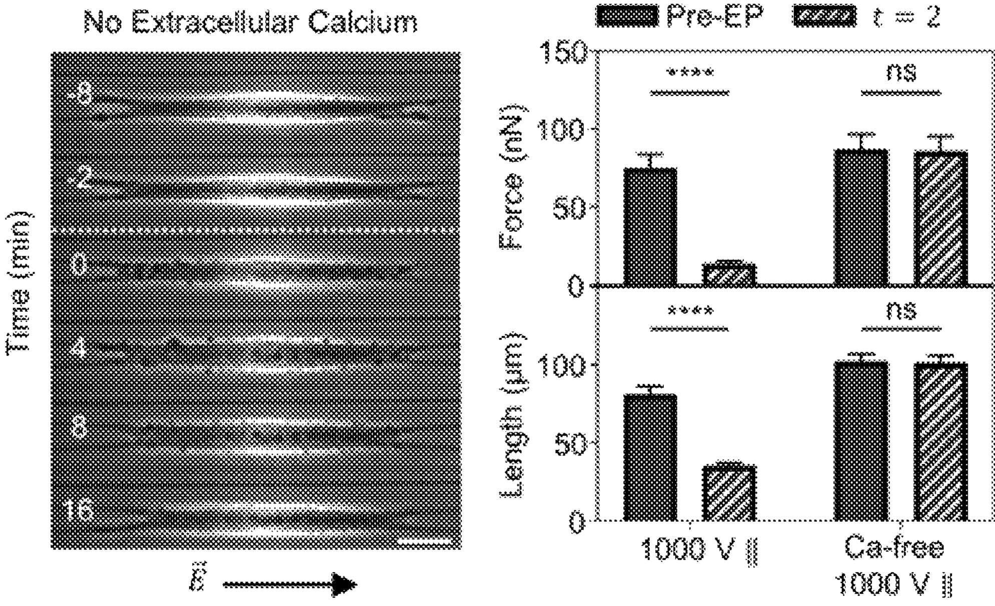

Stage 2: The biphasic stage begins at a force minimum following the cell rounding stage, in a state of high membrane blebbing. A significant increase of contractile force (FIG. 3F) occurs during the first half of this stage (phase I), averaging 11±1 nN or 14% of the average pre-electroporation value. Some cells show force increases up to 40 nN or 48% of the average pre-electroporation force value. The maximum force during this stage is reached when nearly all membrane blebs have disappeared (FIG. 3B, t=16-24 min). Following the local force maximum, contractility decreases (FIG. 3B, t=16-32 min) to a local minimum value that is not statistically different from first minimum (phase II) (FIG. 3F). The duration of phase I and phase II are nearly equal (FIG. 3E). During the entire biphasic stage, cell length remained almost unchanged (FIG. 3F). The total duration of the biphasic stage increased with increasing field strength (FIG. 3E) in both the parallel orientation (500 V: 21±1 min; 1000 V: 25±3 min; 1500 V: 32±4 min) and in the perpendicular orientation (500 V: no response; 1000 V: 22±1 min; 1500 V: 47±19 min).

Stage 3: The cell spreading phase is characterized by a gradual recovery of contractility as the cell re-spreads along the fibers (FIG. 3B, t=32-216 min). Cells eventually recover their pre-electroporation elongation as well as their pre-electroporation contractile force.

Figure 4A:
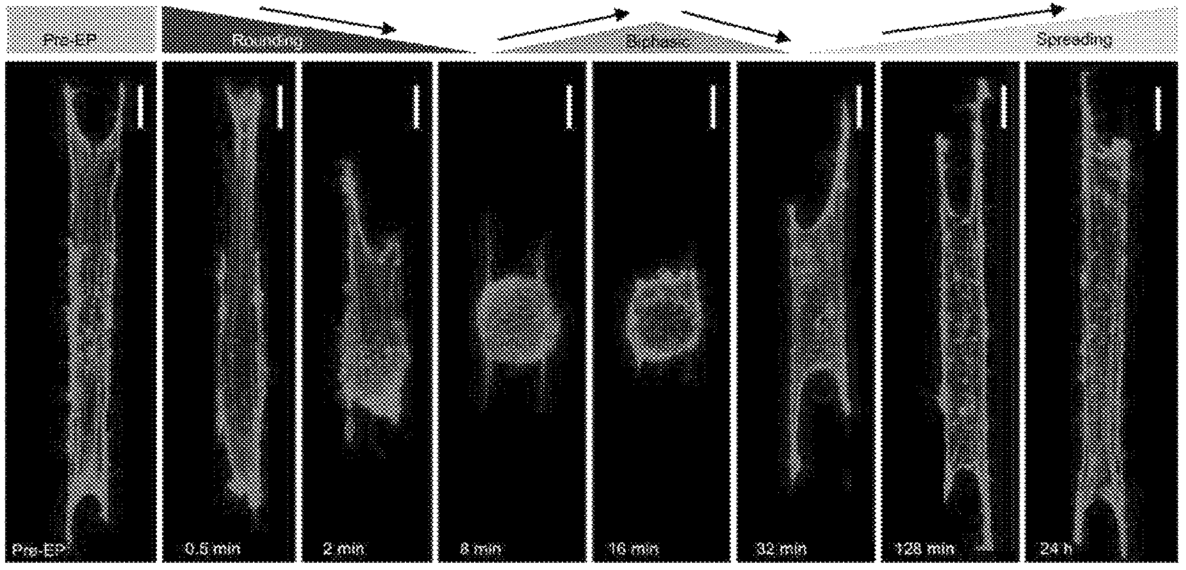
FIGS. 4A-4F shows electroporation disrupts the cytoskeleton.
Figure 4B:
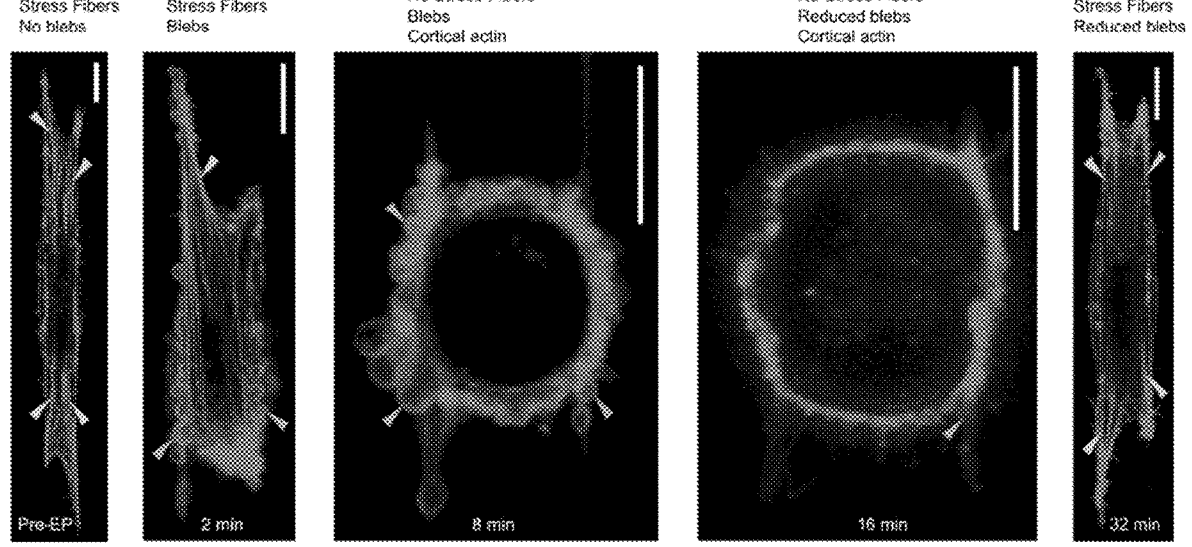
Figure 4C:
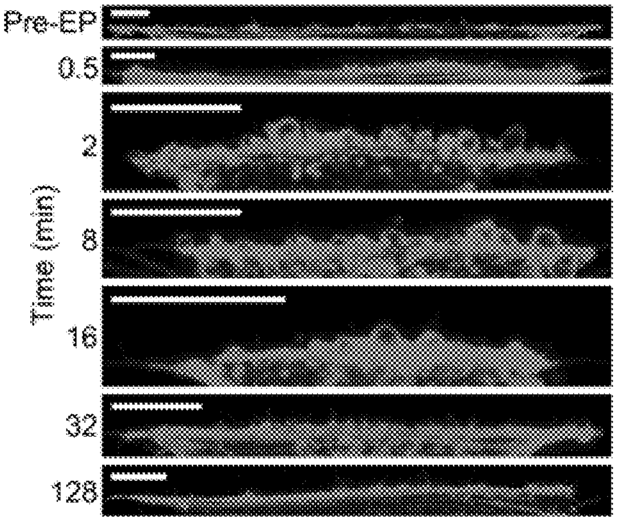
Figure 4D:
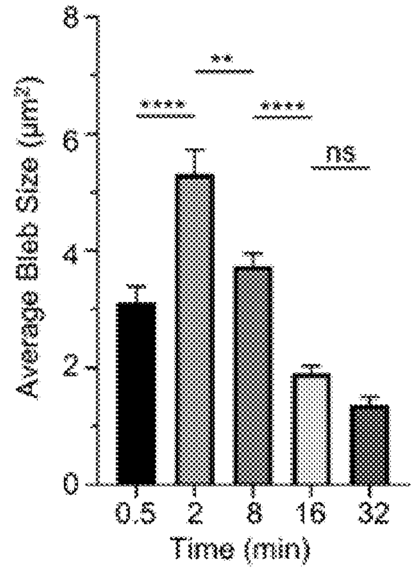
Figure 4E:
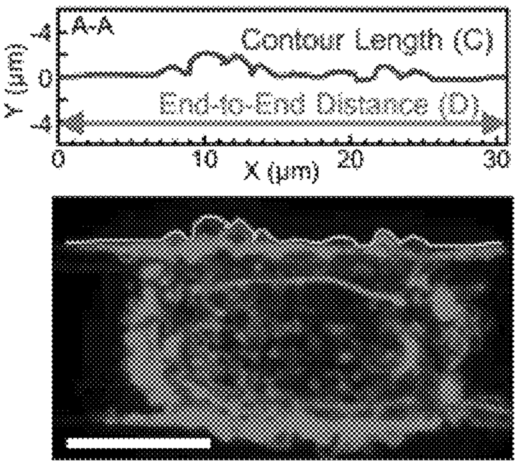
Figure 4F:
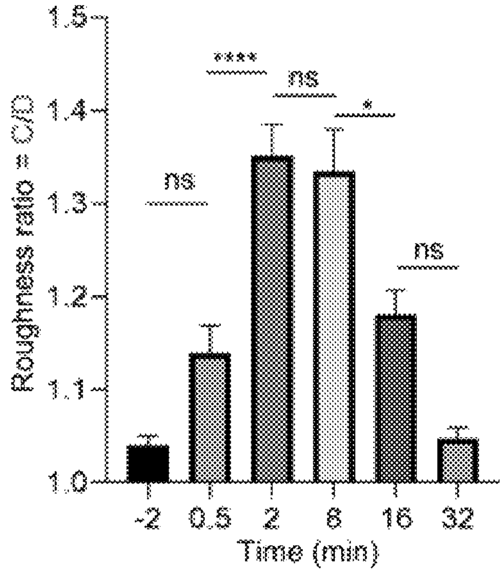
Figure 10:
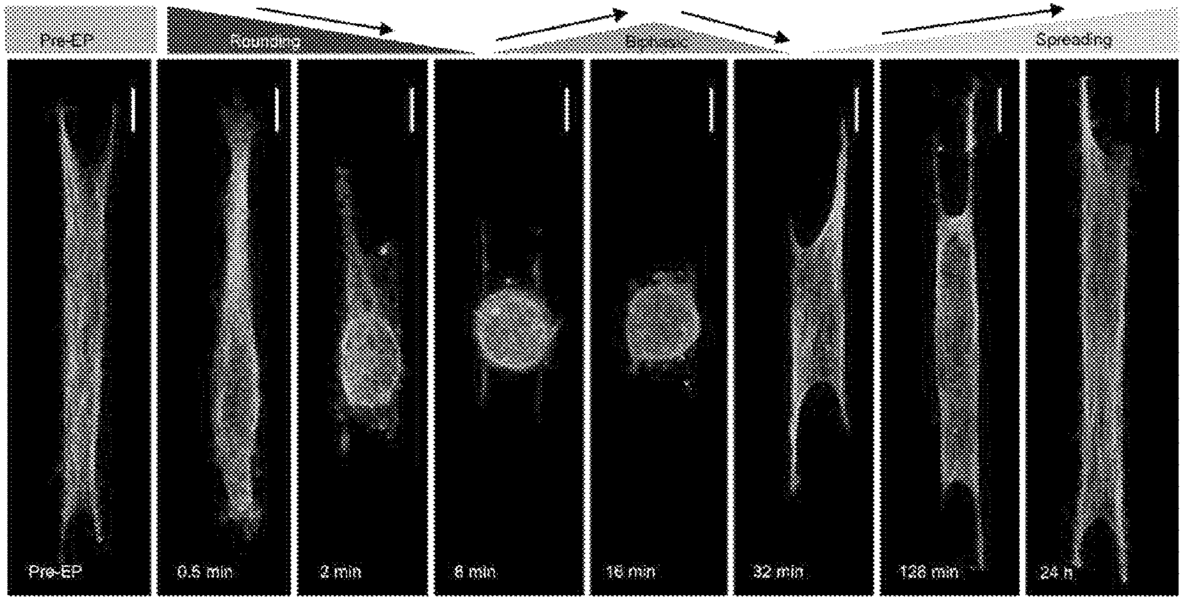
FIG. 10 shows electroporation disrupts the cytoskeleton. Maximum intensity projections of cells stained for microtubules before electroporation and during various stages of recovery post-electroporation (1000 V ||). Microtubule dynamics after electroporation. Electroporated cells (1000 V ||) show a loss of microtubule alignment as the cells round, localization of tubulin at membrane blebs, and an eventual recovery of structure within 2 hours. Scales bars 10 μm.
Figure 11A:
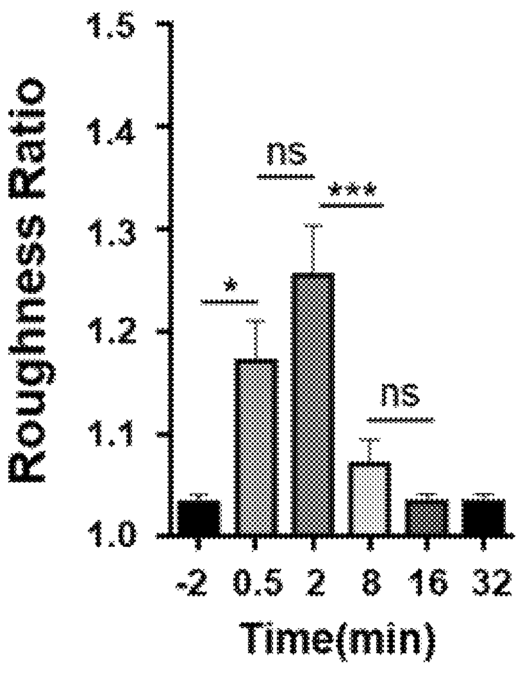
FIGS. 11A-11E show analysis of blebbing and dye uptake in calcium-free media.
Figure 11B:
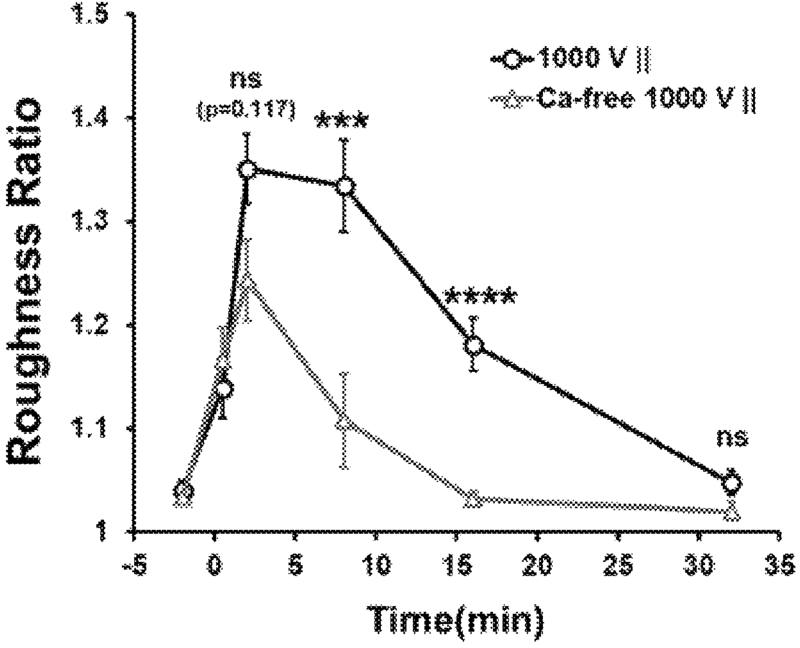

Example 13: Cytoskeletal Reorganization Drives Cell Contractile Response Post-Electroporation The cytoskeleton plays a major role in regulating the contractile response of cells. Immunofluorescent staining was performed for the major cytoskeletal components, actin (FIGS. 4A-4F) and microtubules (FIG. 10), on fixed cells at various timepoints post-electroporation (1000 V ‖; 0.5, 2, 8, 16, 32, 128 min and 24 h) and compared cytoskeletal structure with non-electroporated cells. Non-electroporated cells show well-developed actin stress fibers and continuous microtubules aligned with cell elongation (FIGS. 4A-4B, 10). During the cell-rounding stage (FIGS. 3B, 4A-4B, 0.5 and 2 min timepoints) as cells begin to detach from the fibers and decrease in length, the aligned actin fibers and microtubules get disrupted and blebs form on the cell membrane. By 8 minutes, the f-actin stress fibers were nearly nonexistent, and cells take on a rounded shape with the actin primarily localized at the cortex or on actin-rich retraction fibers originating from prior adhesion sites along the nanofibers. Throughout the cell-rounding stage and at the early phases of the biphasic force response stage (2, 8 min post-electroporation), high levels of membrane blebbing were observed (FIG. 3B) with very large individual blebs (up to 20-30 $\mu m^2$ projected area). Using two metrics for blebbing, bleb size and membrane "roughness" (see Experimental section for details), blebbing was found to be maximal at two minutes post-electroporation, with significant decreases by 16 minutes, and baseline values by 32 minutes (FIGS. 4C-4F). Also at 32 minutes, the formation of the actin stress fibers was observed, indicating the start of Stage 3 (cell-spreading stage) of force recovery. At 128 min, electroporated cells show a fully recovered cytoskeletal structure with well-defined actin stress fibers and aligned, continuous microtubules. Blebbing dynamics in calcium-free DMEM followed similar trends, but the bleb recovery was faster (FIGS. 11A-11B).

Example 14: Location of Cell Membrane Permeability Post-Electroporation

Figure 5A:
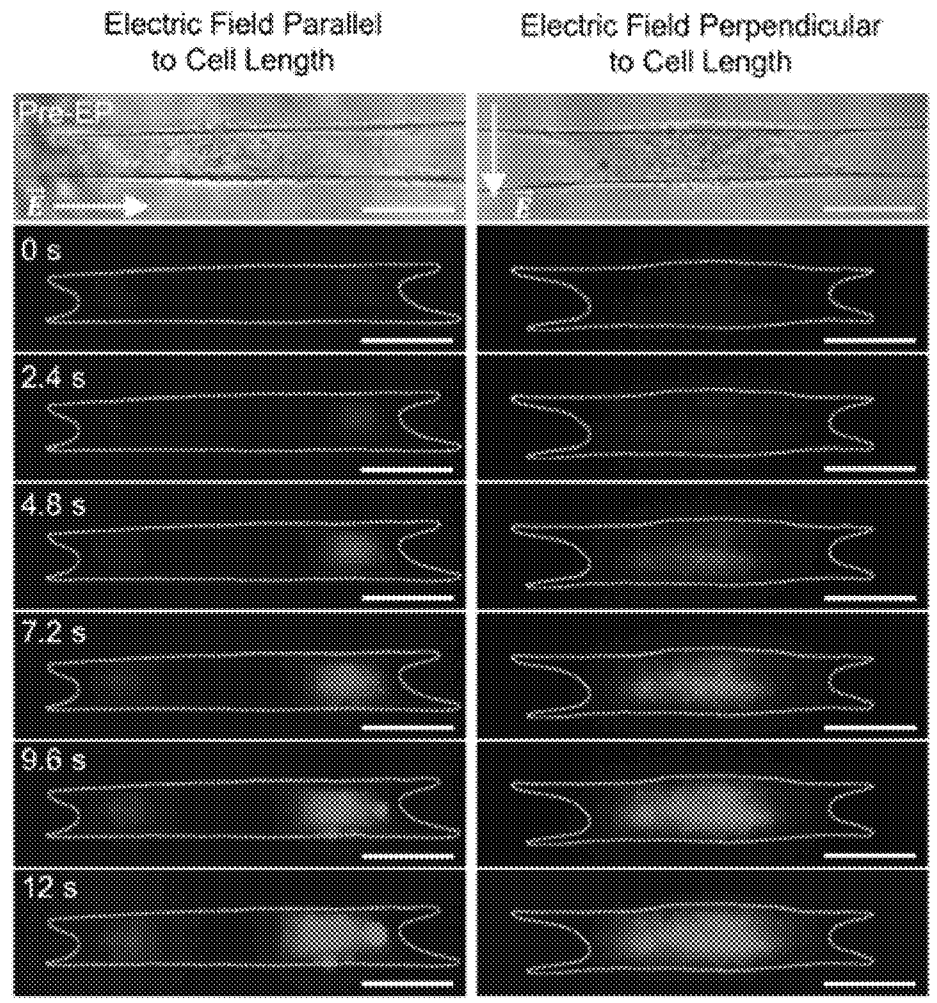
FIGS. 5A-5C show cell orientation affects membrane permeability after electroporation.
Figure 5B:
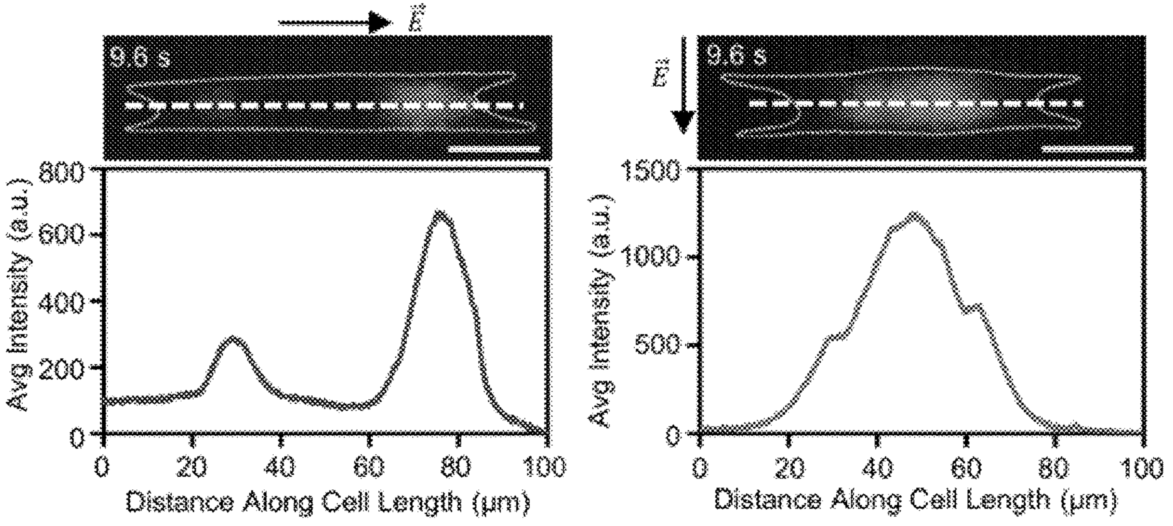
Figure 5C:
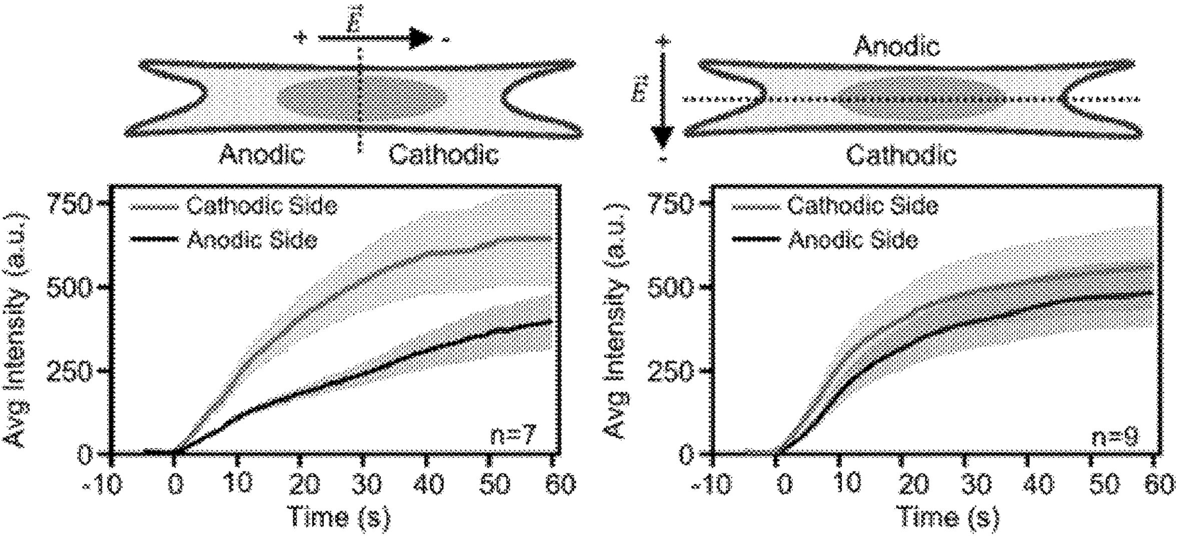
Figure 11C:
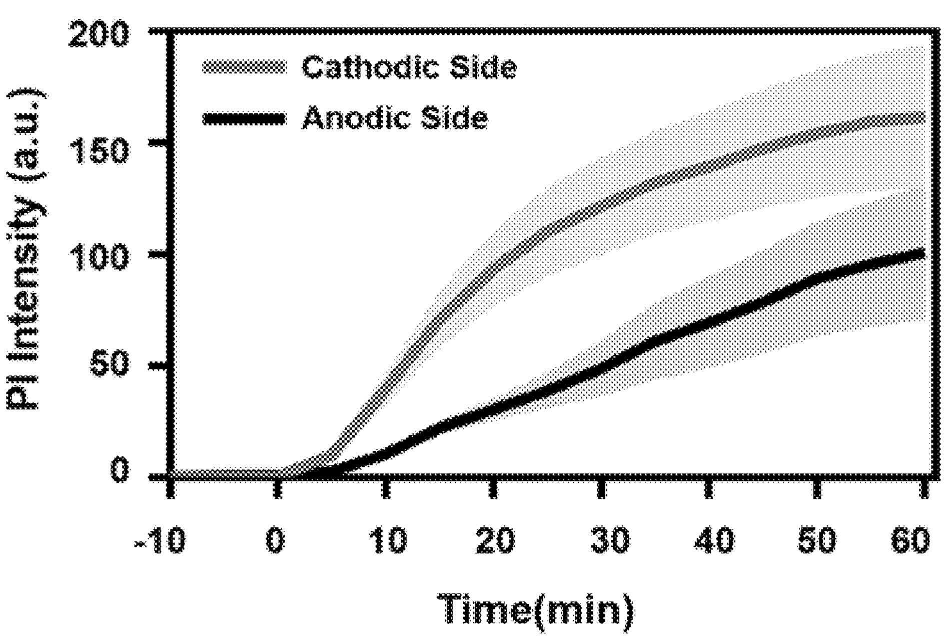
Figure 11D:
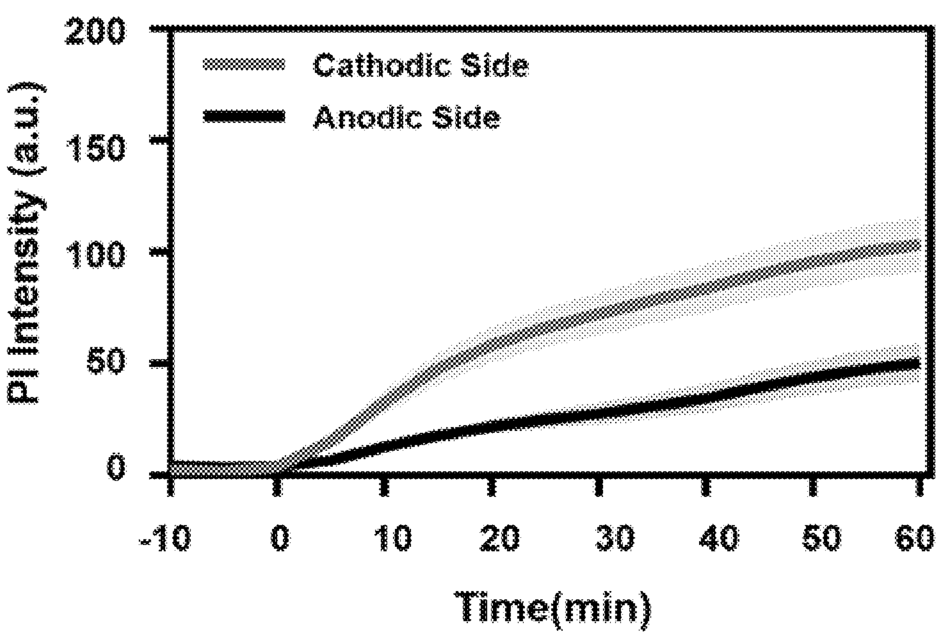

To better understand the orientation-dependent cell responses observed for contractile force and cell length, the mechanism of membrane permeability was affected by the orientation of the cell with respect to the electric field was determined. The temporal dynamics of propidium iodide (PI) uptake were visualized during and after the application of ten, 1000 V pulses (‖: 882 V $cm^{-1}$; ⊥: 911 V $cm^{-1}$) delivered at 1 Hz. It was found that PI entered cells at both the anodic (hyperpolarized) and cathodic (depolarized) sides of the cells (with respect to electric field): near the cell's endpoints (protrusions) in the parallel orientation and along the cell's width in the perpendicular orientation (FIGS. 5A-5C). Incidentally, it was observed that PI uptake is biased toward the cathodic side of the cell (FIG. 5C) with the initial rate of fluorescence intensity change (a.u./s) two times greater compared to the anodic side in the parallel orientation (22.9±3.7 vs 10.7±1.1 a.u./s), while the perpendicular orientation showed a smaller but still significant difference between the cathodic and anodic side (26.1±5.7 vs 18.5±3.7 a.u/s). PI uptake followed similar kinetics in calcium-free media compared to regular media (FIGS. 11C-11D).

Figure 6A:
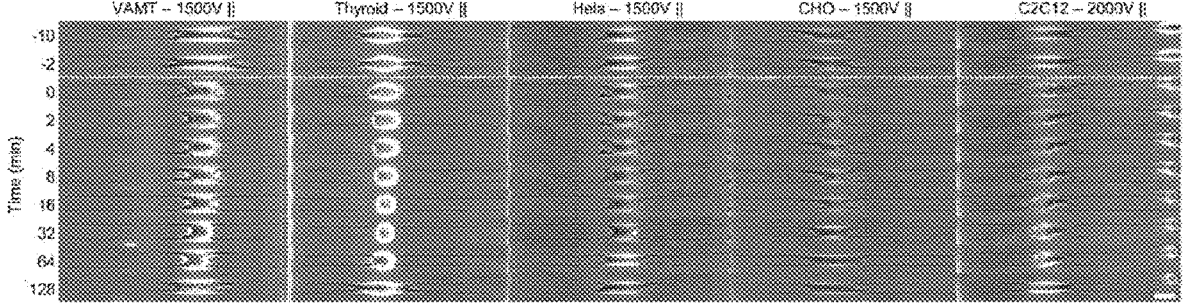
FIGS. 6A-6C show electroporation experiments on five additional cells lines conducted at 1500 V or 2000 V in the parallel orientation.
Figure 6B:
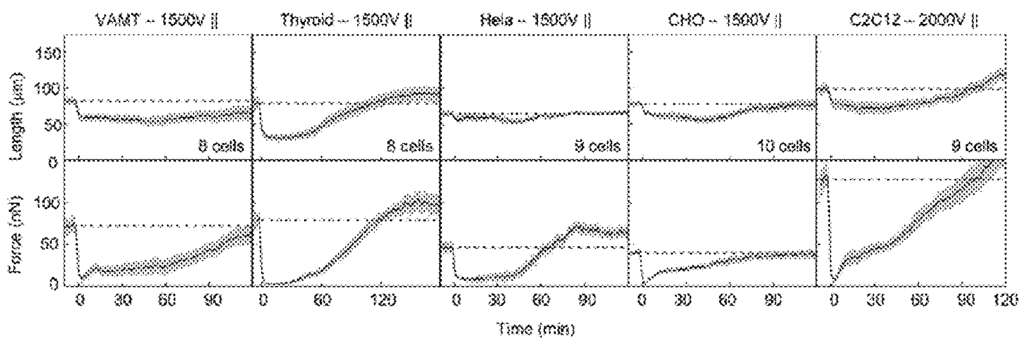
Figure 6C:
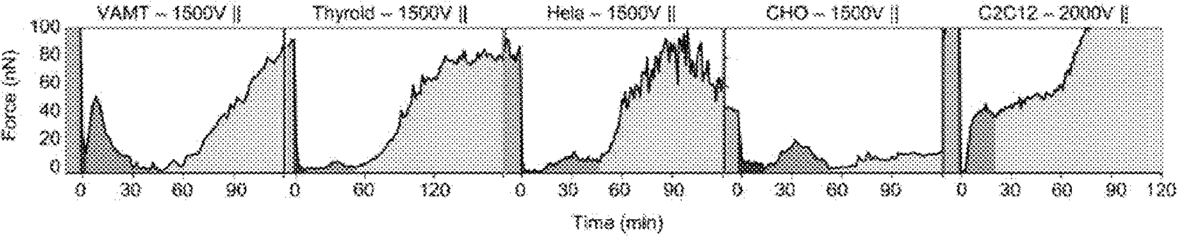

Example 15: Cell Contractility and not Necessarily Cell Shape is Sensitive to Pulsed Electric Fields To determine if the disclosed findings of cell shape and force recovery were generalizable to other cell types, electroporation effects on five other cell lines were investigated: VAMT cells (human mesothelioma), B57 human thyroid cancer cells, CHO-K1 cells (Chinese Hamster Ovary), C2C12 cells (mouse myoblasts), and HeLa cells (human cervical cancer). Electroporation experiments were performed with cells in the parallel orientation (FIGS. 6A-6B). Although the magnitude of contractile force pre-electroporation varied between cell lines, all cells lines demonstrated a rapid and significant loss in force after electroporation, followed by an eventual recovery of force in 1 to 2 hours. Importantly, experiments with all cell types showed instances of cells undergoing biphasic force responses (stage 2) during recovery (FIG. 6C). Furthermore, it was found that contractile force is a much more sensitive indicator of cell recovery compared to cell shape (length) alone, as HeLa and CHO cells showed minimal rounding, but a significant loss of force after electroporation. Overall, these experiments with additional cell types, both healthy and cancerous, demonstrate that loss of force after electroporation is cell-line independent, while severe loss of cell shape was cell-type dependent.

Example 16: Conclusions

Despite the extensive development and use of electroporation technologies in various biological applications, the dynamics of mechanical recovery to tensional homeostasis in cells post-electroporation remain poorly understood. Complementary to membrane-centric approaches to electroporation reported in literature, herein is provided a mechanobiological investigation of electroporated cells by measuring the contractile forces of single cells adherent to extracellular matrix-mimicking suspended fibers. The disclosed network of suspended nanofibers constrains cells to be elongated, in high-aspect ratio shapes with inherent mechanical, biological, and spatial anisotropy, properties that are investigated with two electric field directions (FIGS. 1A-1F). It has been demonstrated herein that both electric field magnitude and direction significantly impact the contractile response of cells, which occurs in three distinct stages during the recovery process (FIGS. 2A-2F): an initial loss in contractility immediately post-electroporation (Stage 1), a biphasic force response (Stage 2), and force recovery to pre-pulse contractility (Stage 3).

Figure 11E:
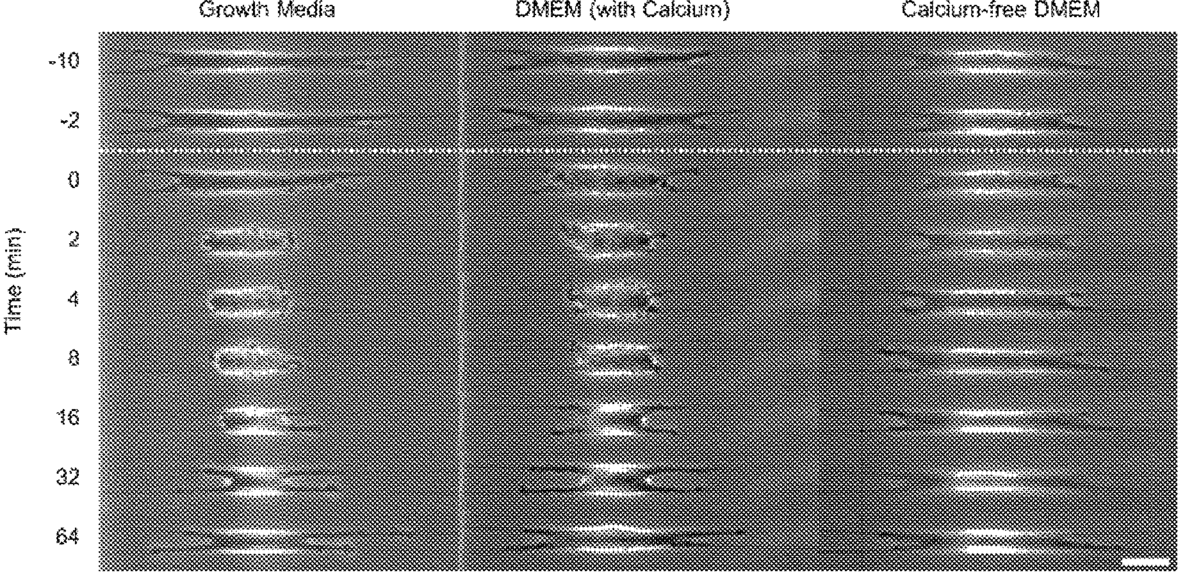

Cells attached to the disclosed parallel network of fibers form clusters of focal adhesions at their extremities, and upon electroporation, the adhesions are broken, leading to cell rounding. The observations of minimal cell rounding in the absence of extracellular calcium (FIG. 3G) implicates extracellular $Ca^{2+}$-induced focal adhesion disassembly as a possible contributing factor to the cell-rounding stage. It is well established that electroporation disrupts the transmembrane $Ca^{2+}$ gradient and causes an influx of extracellular calcium inside the cell, and that locally-elevated intracellular calcium levels can lead to disassembly of focal adhesions within minutes. This conclusion is reinforced by the observation that membrane disruption (PI uptake) precedes cell rounding and that cells in the parallel orientation (disruption near focal adhesions) round more rapidly than cells in the perpendicular direction (disruption along cell body length). FIGS. 11C-11D show PI uptake after electroporation at 1000 V (parallel orientation) in (FIG. 11C) growth media (1.95 mM calcium, n=8) and (FIG. 11D) calcium-free DMEM (n=12). PI uptake dynamics were recorded every 5 seconds with a 20×0.8 NA objective. Furthermore, cell rounding was observed after electroporation in calcium-containing DMEM (1.8 mM, no serum), further implicating calcium in cell rounding (FIG. 11E). Cell rounding after electroporation has been previously attributed to colloid-osmotic swelling, however the results presented herein demonstrate the important role of extracellular calcium in the loss of cell adhesion. Incidentally, some evidence was found that cells with higher levels of pre-pulse contractility undergo a faster cell-rounding stage, suggesting a 'slingshot effect' caused by the contractile actin stress fibers that accelerate the rounding process (FIG. 8D). Rapid loss of actin stress fibers and microtubule structure are observed following the electric field treatment, as prior studies have also noted. Cytoskeletal disruption was concomitant with the formation of blebs, with peak bleb size observed at 2 minutes post-electroporation (1000 V ||) corresponding closely with maximal loss of cell contractility. Bleb elimination by 32 min (1000 V ||) post-electroporation is in reasonable agreement with the timescales of membrane resealing previously reported.

As cells become rounded at the end of the cell-rounding stage, the contractility measurements demonstrate a biphasic response with a significant rise in forces but with a minimal change in cell length during the first half of this stage. Although the exact mechanisms responsible for the biphasic force response remain unknown, three factors likely contribute. Firstly, during the initial phase of force recovery, contractility increases as blebbing decreases. Bleb reduction by contraction of cortical actin likely contributes to the increased contractility observed. Secondly, cell volume may decrease slightly after electroporation (FIGS. 9C-9D) and contribute to the increase in force. Cell volume has been shown to change after electroporation due to colloid-osmotic pressure imbalances, and it is now well-appreciated that cell volume is regulated by the interplay of the cytoskeletal tension-mediated water efflux and water retention by the cell cytoplasm. Thirdly, increased levels of intracellular $Ca^{2+}$ have been shown to cause aggregation of endoplasmic reticulum $Ca^{2+}$ sensor STIM1, which then leads to the recruitment of the force-bearing focal adhesion protein, talin, and could thereby account for the increased cell contractility in the first phase of this biphasic stage. The reduced contractility seen in phase II is most likely indicative of a reorganization of actin, possibly from a bleb-reduction configuration to a spreading configuration, yet the specific mechanisms are unknown.

Irrespective of the electric field strength and orientation, cells that were viable 3-4 hours post-electroporation had fully-restored contractility typically within the first 1-3 hours post-electroporation. Such timescales for cell contractile recovery falls within the reported range of cytoskeletal recovery times (minutes to days). Owing to the physical connections existing between the actin cytoskeleton and the plasma membrane, compromised membrane integrity leads to significant cytoskeletal disruption, thereby causing a loss of the tensional homeostasis in cells. Thus, by measuring single-cell contractility as the primary metric of cell recovery, the disclosed mechanobiological approach integrates the recovery responses of various cellular components for a more encompassing metric of cell recovery than membrane permeability measurements alone.

Figure 12:
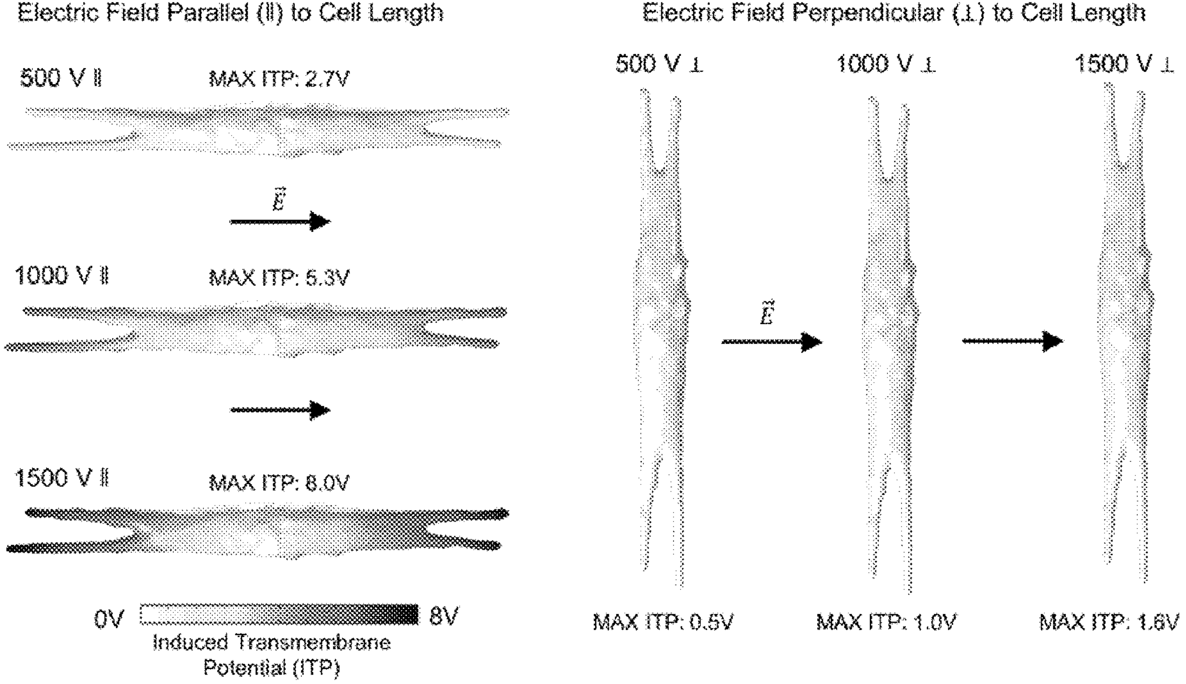
FIG. 12 shows the induced transmembrane potential (ITP) model of a 3D cell in two orientations. A steady-state computational model of the induced transmembrane potential (ITP) of reconstructed cells indicates differences in the spatial distribution and magnitude of ITP. Cells elongated parallel to the field show high ITP values distributed around the protrusions of the cell. ITP is defined as the voltage difference across the cell membrane at the moment prior to pore formation. Conversely, cells elongated perpendicularly to the field show lower ITP levels that are distributed around the sidewalls of the cell.

Higher cell viability after application of electric fields that are aligned with cell length (parallel configuration) is not explained by the 3D computational models of the induced transmembrane potential (ITP) (FIG. 12). These simple ITP models (steady-state, constant membrane conductivity) indicate that cells in the parallel orientation should have greater overall disruption compared to the perpendicular orientation. Modifying the model to include dynamic membrane conductivity, cell shape-change after pulsing, electric field disruption near the nanofibers, pore characteristics (number and radii), and/or total mass transport across the membrane might reconcile the differences between experimental viability results and model predictions. It is believed that cell rounding decreases membrane tension, a property that affects the electroporation threshold, thereby reducing membrane permeability to enhance cell survival. Incidentally, it was found that dye uptake was asymmetric with a bias toward the cathodic (depolarized) side of the cell, a finding consistent with previous studies but not explained by electroporation theory. Finally, maximal ITP values of 0.5 V (below or near the electroporation threshold range, ~0.2-1 V) for cells treated at 500 V in the perpendicular orientation indicate minimal to no electroporation for this condition, a result consistent with minimal changes to contractile force or length with no YO-PRO-1 uptake observed (data not shown). In contrast, the disclosed ITP models predict pore formation for all other voltage and orientation conditions, in good agreement with the experimental results reported herein, demonstrating loss of contractility and cell elongation for these conditions.

Cell force recovery has been previously investigated in the context of rapid mechanical stretching events, and not for electroporation, which is shown here. While mechanical stretching and electric field treatment are fundamentally different cues, the cellular contractility response to perturbation bear similarities. Studies show that rapid mechanical stretching disrupts tensional homeostasis leading to rapid disruption of the actin cytoskeleton, followed by recovery of cell contractility either in single or multi-stages. For example, it has previously been demonstrated that rapid stretching (20% strain at 800%/s) induced a multi-stage recovery process: a stage of rapid force increase and relaxation (>1 min), a force plateau stage, and finally a gradual active force recovery stage that lasted around 20 minutes. Loss and recovery of cell force was attributed to cytoskeletal fluidization (depolymerization of the actin cytoskeleton) and cytoskeletal resolidification (actin stress fiber recovery) respectively. While these force response patterns resemble the multi-stage force dynamics reported herein, the importance of membrane disruption linked with integrity of cytoskeletal networks in electroporation is noted. The large-scale bleb formation and recession observed in these studies post-electroporation is synchronized with disruption and formation of actin fibers (FIGS. 4A-4F), which might explain why the timescales of electroporation-mediated biphasic force recovery (few minutes) differ from the stretch-mediated shedding of forces occurring typically within a few seconds. Additionally, while mechanical stretching induces a loss in contractility without affecting the overall cell shape, electroporation-mediated disruption can have a loss of cell shape (rounding) followed by recovery (spreading). Such substantial cell shape recoveries may further explain the longer timescales of force recovery (2-3 hours) compared with mechanical stretching (~30 minutes).

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Arena, C. B., et al., Biomed. Eng. Online, "High-frequency irreversible electroporation (H-FIRE) for non-thermal ablation without muscle contraction," 2011, 10:102.
2. Berghofer, T.; Eing, C.; Flickinger, B.; Hohenberger, P.; Wegner, L. H.; Frey, W.; Nick, P., Nanosecond electric pulses trigger actin responses in plant cells. Biochem Biophys Res Commun 2009, 387 (3), 590-5.
3. Bird, S. D., Calcium mediates cell shape change in human peritoneal mesothelial cells. Cell calcium 2018, 72, 116-126.
4. Carr, L.; Bardet, S. M.; Burke, R. C.; Arnaud-Cormos, D.; Leveque, P.; O'Connor, R. P., Calcium-independent disruption of microtubule dynamics by nanosecond pulsed electric fields in U87 human glioblastoma cells. Sci Rep 2017, 7, 41267.
5. Carr, L.; Bardet, S. M.; Burke, R. C.; Arnaud-Cormos, D.; Lévêque, P.; O'connor, R. P., Calcium-independent disruption of microtubule dynamics by nanosecond pulsed electric fields in U87 human glioblastoma cells. Scientific reports 2017, 7, 41267.
6. Čemažar, M., Effects of Electroporation of Mammalian Cells on Cytoskeleton and Intercellular Connections. Handbook of Electroporation 2017, 307-321.
7. Charras, G. T.; Hu, C.-K.; Coughlin, M.; Mitchison, T. J., Reassembly of contractile actin cortex in cell blebs. The Journal of cell biology 2006, 175 (3), 477-490.
8. Chen, C.; Krishnan, R.; Zhou, E.; Ramachandran, A.; Tambe, D.; Rajendran, K.; Adam, R. M.; Deng, L.; Fredberg, J. J., Fluidization and resolidification of the human bladder smooth muscle cell in response to transient stretch. PLoS One 2010, 5 (8), e12035.
9. Chen, Y.-T.; Chen, Y.-F.; Chiu, W.-T.; Wang, Y.-K.; Chang, H.-C.; Shen, M.-R., The ER Ca2+ sensor STIM1 regulates actomyosin contractility of migratory cells. J Cell Sci 2013, 126 (5), 1260-1267.
10. Chikina, A. S.; Svitkina, T. M.; Alexandrova, A. Y., Time-resolved ultrastructure of the cortical actin cytoskeleton in dynamic membrane blebs. J Cell Biol 2019, 218 (2), 445-454.
11. Chiu, F. W. Y. et al., J. Chem. Tech. and Biotech., "A microfluidic toolbox for cell fusion," 2016, 91:16-24.
12. Chopinet, L.; Dague, E.; Rols, M. P., AFM sensing cortical actin cytoskeleton destabilization during plasma membrane electropermeabilization. Cytoskeleton (Hoboken) 2014, 71 (10), 587-94.
13. Chopinet, L.; Roduit, C.; Rols, M. P.; Dague, E., Destabilization induced by electropermeabilization analyzed by atomic force microscopy. Biochim Biophys Acta 2013, 1828 (9), 2223-9.
14. Chopinet, L.; Roduit, C.; Rols, M.-P.; Dague, E., Destabilization induced by electropermeabilization analyzed by atomic force microscopy. Biochimica et Biophysica Acta (BBA)-Biomembranes 2013, 1828 (9), 2223-2229.
15. Chu, G. et al., Nucleic Acids Research, "Electroporation for the efficient transfection of mammalian cells with DNA," 1987, 15:1311-1326.
16. Conklin, M. W.; Lin, M. S.; Spitzer, N. C., Local calcium transients contribute to disappearance of pFAK, focal complex removal and deadhesion of neuronal growth cones and fibroblasts. Developmental biology 2005, 287 (1), 201-212.
17. Davalos, R. V.; Mir, L. M.; Rubinsky, B., Tissue ablation with irreversible electroporation. Annals of Biomedical Engineering 2005, 33 (2), 223-231.
18. D'Souza, R. S.; Lim, J. Y.; Turgut, A.; Servage, K.; Zhang, J.; Orth, K.; Sosale, N. G.; Lazzara, M. J.; Allegood, J.; Casanova, J. E., Calcium-stimulated disassembly of focal adhesions mediated by an ORP3/IQSec1 complex. Elife 2020, 9, e54113.

19. Dutta, D.; Asmar, A.; Stacey, M., Effects of nanosecond pulse electric fields on cellular elasticity. Micron 2015, 72, 15-20.

20. Ford, W. E. et al., Archies Biochem. Biophys., "Nanosecond pulsed electric fields stimulate apoptosis without release of pro-apoptotic factors from mitochondria in B16f10 melanoma," 2010, 497:82-89.

21. Frandsen, S. K.; Gissel, H.; Hojman, P.; Tramm, T.; Eriksen, J.; Gehl, J., Direct therapeutic applications of calcium electroporation to effectively induce tumor necrosis. Cancer research 2012, 72 (6), 1336-1341.

22. Geboers, B.; Scheffer, H. J.; Graybill, P. M.; Ruarus, A. H.; Nieuwenhuizen, S.; Puijk, R. S.; van den Tol, P. M.; Davalos, R. V.; Rubinsky, B.; de Gruijl, T. D.; Miklavčič, D.; Meijerink, M. R., High-Voltage Electrical Pulses in Oncology: Irreversible Electroporation, Electrochemotherapy, Gene Electrotransfer, Electrofusion, and Electroimmunotherapy. Radiology 2020, 295 (2), 254-272.

23. Giannone, G.; Rondé, P.; Gaire, M.; Beaudouin, J.; Haiech, J.; Ellenberg, J.; Takeda, K., Calcium rises locally trigger focal adhesion disassembly and enhance residency of focal adhesion kinase at focal adhesions. Journal of Biological Chemistry 2004, 279 (27), 28715-28723.

24. Giannone, G.; Rondé, P.; Gaire, M.; Haiech, J.; Takeda, K., Calcium oscillations trigger focal adhesion disassembly in human U87 astrocytoma cells. Journal of Biological Chemistry 2002, 277 (29), 26364-26371.

25. Gissel, H.; Lee, R. C.; Gehl, J., Electroporation and cellular physiology. In Clinical aspects of electroporation, Springer: 2011; pp 9-17.

26. Goswami, I.; Perry, J. B.; Allen, M. E.; Brown, D. A.; von Spakovsky, M. R.; Verbridge, S. S., Influence of Pulsed Electric Fields and Mitochondria-Cytoskeleton Interactions on Cell Respiration. Biophysical Journal 2018, 114 (12), 2951-2964.

27. Gothelf, A. et al., Cancer Treatment Reviews, "Electrochemotherapy: results of cancer treatment using enhanced delivery of bleomycin by electroporation," 2003, 29:371-387.

28. Graybill, P. M.; Davalos, R. V., Cytoskeletal Disruption after Electroporation and Its Significance to Pulsed Electric Field Therapies. Cancers 2020, 12 (5), 1132.

29. Guo, M.; Pegoraro, A. F.; Mao, A.; Zhou, E. H.; Arany, P. R.; Han, Y.; Burnette, D. T.; Jensen, M. H.; Kasza, K. E.; Moore, J. R., Cell volume change through water efflux impacts cell stiffness and stem cell fate. Proceedings of the National Academy of Sciences 2017, 114 (41), E8618-E8627.

30. Harkin, D. G.; Hay, E. D., Effects of electroporation on the tubulin cytoskeleton and directed migration of corneal fibroblasts cultured within collagen matrices. Cell Motility and the Cytoskeleton 1996, 35 (4), 345-357.

31. Hibino, M.; Itoh, H.; Kinosita Jr, K., Time courses of cell electroporation as revealed by submicrosecond imaging of transmembrane potential. Biophysical journal 1993, 64 (6), 1789-1800.

32. Hohenberger, P.; Eing, C.; Straessner, R.; Durst, S.; Frey, W.; Nick, P., Plant actin controls membrane permeability. Biochim Biophys Acta 2011, 1808 (9), 2304-12.

33. Hu, N.; Yang, J.; Joo, S. W.; Banerjee, A. N.; Qian, S. Z., Cell electrofusion in microfluidic devices: A review. Sensors and Actuators B-Chemical 2013, 178, 63-85.

34. Hu, Q.; Joshi, R.; Beskok, A., Model study of electroporation effects on the dielectrophoretic response of spheroidal cells. Journal of Applied Physics 2009, 106 (2), 024701.

35. Jana, A.; Nookaew, I.; Singh, J.; Behkam, B.; Franco, A. T.; Nain, A. S., Crosshatch nanofiber networks of tunable interfiber spacing induce plasticity in cell migration and cytoskeletal response. The FASEB Journal 2019, fj. 201900131R.

36. Jarm, T.; Cemazar, M.; Miklavčič, D.; Sersa, G., Antivascular effects of electrochemotherapy: implications in treatment of bleeding metastases. Expert Rev Anticancer Ther 2010, 10 (5), 729-46.

37. Kanduser, M.; Šentjurc, M.; Miklavčič, D., Cell membrane fluidity related to electroporation and resealing. European Biophysics Journal 2006, 35 (3), 196-204.

38. Kanthou, C.; Kranjc, S.; Sersa, G.; Tozer, G.; Zupanic, A.; Cemazar, M., The endothelial cytoskeleton as a target of electroporation-based therapies. Mol Cancer Ther 2006, 5 (12), 3145-52.

39. Kotnik, T.; Miklavčič, D.; Slivnik, T., Time course of transmembrane voltage induced by time-varying electric fields—a method for theoretical analysis and its application. Bioelectrochemistry and bioenergetics 1998, 45 (1), 3-16.

40. Kotnik, T.; Pucihar, G.; Miklavčič, D., Induced transmembrane voltage and its correlation with electroporation-mediated molecular transport. The Journal of membrane biology 2010, 236 (1), 3-13.

41. Kotnik, T.; Rems, L.; Tarek, M.; Miklavčič, D., Membrane electroporation and electropermeabilization: mechanisms and models. Annual review of biophysics 2019, 48, 63-91.

42. Krassowska, W.; Filev, P. D., Modeling electroporation in a single cell. Biophysical journal 2007, 92 (2), 404-417.

43. Krishnan, R.; Canovic, E. P.; lordan, A. L.; Rajendran, K.; Manomohan, G.; Pirentis, A. P.; Smith, M. L.; Butler, J. P.; Fredberg, J. J.; Stamenovic, D., Fluidization, resolidification, and reorientation of the endothelial cell in response to slow tidal stretches. Am J Physiol Cell Physiol 2012, 303 (4), C368-75.

44. Krishnan, R.; Park, C. Y.; Lin, Y. C.; Mead, J.; Jaspers, R. T.; Trepat, X.; Lenormand, G.; Tambe, D.; Smolensky, A. V.; Knoll, A. H.; Butler, J. P.; Fredberg, J. J., Reinforcement versus fluidization in cytoskeletal mechanoresponsiveness. PLoS One 2009, 4 (5), e5486.

45. Lan, B.; Krishnan, R.; Park, C. Y.; Watanabe, R. A.; Panganiban, R.; Butler, J. P.; Lu, Q.; Cole, W. C.; Fredberg, J. J., Transient stretch induces cytoskeletal fluidization through the severing action of cofilin. American Journal of Physiology-Lung Cellular and Molecular Physiology 2018, 314 (5), L799-L807.

46. Lee, S. L.; Nekouzadeh, A.; Butler, B.; Pryse, K. M.; McConnaughey, W. B.; Nathan, A. C.; Legant, W. R.; Schaefer, P. M.; Pless, R. B.; Elson, E. L.; Genin, G. M., Physically-induced cytoskeleton remodeling of cells in three-dimensional culture. PLoS One 2012, 7 (12), e45512.

47. Mali, B.; Jarm, T.; Snoj, M.; Sersa, G.; Miklavcic, D., Antitumor effectiveness of electrochemotherapy: A systematic review and meta-analysis. Ejso 2013, 39 (1), 4-16.

48. Maswiwat, K.; Wachner, D.; Gimsa, J., Effects of cell orientation and electric field frequency on the transmembrane potential induced in ellipsoidal cells. Bioelectrochemistry 2008, 74 (1), 130-141.

49. Mermelstein, C.; Rebello, M.; Amaral, L.; Costa, M., Changes in cell shape, cytoskeletal proteins and adhesion sites of cultured cells after extracellular Ca2+ chelation. Brazilian journal of medical and biological research 2003, 36 (8), 1111-1116.

50. Meulenberg, C. J.; Todorovic, V.; Cemazar, M., Differential cellular effects of electroporation and electrochemotherapy in monolayers of human microvascular endothelial cells. PLoS One 2012, 7 (12), e52713.
51. Murovec, T.; Sweeney, D. C.; Latouche, E.; Davalos, R. V.; Brosseau, C., Modeling of transmembrane potential in realistic multicellular structures before electroporation. Biophysical journal 2016, 111 (10), 2286-2295.
52. Mussauer, H.; Sukhorukov, V.; Haase, A.; Zimmermann, U., Resistivity of red blood cells against high-intensity, short-duration electric field pulses induced by chelating agents. The Journal of membrane biology 1999, 170 (2), 121-133.
53. Nain, A. S.; Wang, J., Polymeric nanofibers: isodiametric design space and methodology for depositing aligned nanofiber arrays in single and multiple layers. Polymer Journal 2013, 45 (7), 695-700.
54. Nain, A. S. Methods, apparatus, and systems for fabrication of polymeric nano- and micro-fibers in aligned configurations, U.S. Pat. No. 9,029,149, issued May 12, 2015.
55. Nain, A. S. Nanofiber grid and related methods, U.S. Pat. No. 9,753,023, issued Sep. 5, 2017.
56. Neamtu, S.; Morariu, V.; Turcu, I.; Popescu, A. H.; Copăescu, L. I., Pore resealing inactivation in electroporated erythrocyte membrane irradiated with electrons. Bioelectrochemistry and bioenergetics 1999, 48 (2), 441-445.
57. Needham, D.; Hochmuth, R., Electro-mechanical permeabilization of lipid vesicles. Role of membrane tension and compressibility. Biophysical journal 1989, 55 (5), 1001-1009.
58. Nekouzadeh, A.; Pryse, K. M.; Elson, E. L.; Genin, G. M., Stretch-activated force shedding, force recovery, and cytoskeletal remodeling in contractile fibroblasts. J Biomech 2008, 41 (14), 2964-71.
59. Nesin, O. M.; Pakhomova, O. N.; Xiao, S.; Pakhomov, A. G., Manipulation of cell volume and membrane pore comparison following single cell permeabilization with 60- and 600-ns electric pulses. Biochimica et Biophysica Acta (BBA)-Biomembranes 2011, 1808 (3), 792-801.
60. Padhi, A.; Thomson, A. H.; Perry, J. B.; Davis, G. N.; McMillan, R. P.; Loesgen, S.; Kaweesa, E. N.; Kapania, R.; Nain, A. S.; Brown, D. A., Bioenergetics underlying single cell migration on aligned nanofiber scaffolds. American Journal of Physiology-Cell Physiology 2019.
61. Pakhomov, A. G.; Xiao, S.; Pakhomova, O. N.; Semenov, I.; Kuipers, M. A.; Ibey, B. L., Disassembly of actin structures by nanosecond pulsed electric field is a downstream effect of cell swelling. Bioelectrochemistry 2014, 100, 88-95.
62. Pavlin, M.; Miklavcic, D., Theoretical and experimental analysis of conductivity, ion diffusion and molecular transport during cell electroporation—relation between short-lived and long-lived pores. Bioelectrochemistry 2008, 74 (1), 38-46.
63. Pehlivanova, V. N.; Tsoneva, I. H.; Tzoneva, R. D., Multiple effects of electroporation on the adhesive behaviour of breast cancer cells and fibroblasts. Cancer Cell Int 2012, 12 (1), 9.
64. Perrier, D. L.; Vahid, A.; Kathavi, V.; Stam, L.; Rems, L.; Mulla, Y.; Muralidharan, A.; Koenderink, G. H.; Kreutzer, M. T.; Boukany, P. E., Response of an actin network in vesicles under electric pulses. Sci Rep 2019, 9 (1), 8151.
65. Platonova, A.; Ponomarchuk, O.; Boudreault, F.; Kapilevich, L. V.; Maksimov, G. V.; Grygorczyk, R.; Orlov, S. N., Role of cytoskeleton network in anisosmotic volume changes of intact and permeabilized A549 cells. Biochimica et Biophysica Acta (BBA)-Biomembranes 2015, 1848 (10), 2337-2343.
66. Potter, H.; Heller, R., Transfection by Electroporation. Curr Protoc Mol Biol 2018, 121 (1), 931-9313.
67. Pucihar, G.; Kotnik, T.; Vali, B.; Miklavčič, D., Numerical determination of transmembrane voltage induced on irregularly shaped cells. Annals of biomedical engineering 2006, 34 (4), 642.
68. Pucihar, G.; Miklavcic, D.; Kotnik, T., A time-dependent numerical model of transmembrane voltage inducement and electroporation of irregularly shaped cells. IEEE Transactions on Biomedical Engineering 2009, 56 (5), 1491-1501.
69. Rems, L.; Ušaj, M.; Kanduser, M.; Reberšek, M.; Miklavčič, D.; Pucihar, G., Cell electrofusion using nanosecond electric pulses. Scientific reports 2013, 3, 3382.
70. Rols, M. P.; Teissie, J., Experimental evidence for the involvement of the cytoskeleton in mammalian cell electropermeabilization. Biochim Biophys Acta 1992, 1111 (1), 45-50.
71. Rols, M.-P.; Teissie, J., Electropermeabilization of mammalian cells. Quantitative analysis of the phenomenon. Biophysical journal 1990, 58 (5), 1089-1098.
72. Sano, M. B.; Arena, C. B.; DeWitt, M. R.; Saur, D.; Davalos, R. V., In-vitro bipolar nano- and microsecond electro-pulse bursts for irreversible electroporation therapies. Bioelectrochemistry 2014, 100, 69-79.
73. Saulis, G., Pore disappearance in a cell after electroporation: theoretical simulation and comparison with experiments. Biophysical journal 1997, 73 (3), 1299-1309.
74. Saulis, G.; Venslauskas, M. S.; Naktinis, J., Kinetics of pore resealing in cell membranes after electroporation. Journal of Electroanalytical Chemistry and Interfacial Electrochemistry 1991, 321 (1), 1-13.
75. Schaub, S.; Bohnet, S.; Laurent, V. M.; Meister, J.-J.; Verkhovsky, A. B., Comparative maps of motion and assembly of filamentous actin and myosin II in migrating cells. Molecular biology of the cell 2007, 18 (10), 3723-3732.
76. Scheffer, H. J.; Nielsen, K.; de Jong, M. C.; van Tilborg, A. A.; Vieveen, J. M.; Bouwman, A. R.; Meijer, S.; van Kuijk, C.; van den Tol, P. M.; Meijerink, M. R., Irreversible electroporation for nonthermal tumor ablation in the clinical setting: a systematic review of safety and efficacy. J Vasc Interv Radiol 2014, 25 (7), 997-1011; quiz 1011.
77. Sharma, P.; Sheets, K.; Elankumaran, S.; Nain, A. S., The mechanistic influence of aligned nanofibers on cell shape, migration and blebbing dynamics of glioma cells. Integrative Biology 2013, 5 (8), 1036-1044.
78. Sheets, K.; Wang, J.; Zhao, W.; Kapania, R.; Nain, A. S., Nanonet Force Microscopy for Measuring Cell Forces. Biophysical Journal 2016, 111 (1), 197-207.
79. Sheets, K.; Wunsch, S.; Ng, C.; Nain, A. S., Shape-dependent cell migration and focal adhesion organization on suspended and aligned nanofiber scaffolds. Acta Biomaterialia 2013, 9 (7), 7169-7177.
80. Sözer, E. B.; Pocetti, C. F.; Vernier, P. T., Asymmetric patterns of small molecule transport after nanosecond and microsecond Electropermeabilization. The Journal of membrane biology 2018, 251 (2), 197-210.
81. Stacey, M.; Fox, P.; Buescher, S.; Kolb, J., Nanosecond pulsed electric field induced cytoskeleton, nuclear membrane and telomere damage adversely impact cell survival. Bioelectrochemistry 2011, 82 (2), 131-4.
82. Steuer, A.; Schmidt, A.; Laboha, P.; Babica, P.; Kolb, J. F., Transient suppression of gap junctional intercellular communication after exposure to 100-nanosecond pulsed electric fields. Bioelectrochemistry 2016, 112, 33-46.

83. Steuer, A.; Wende, K.; Babica, P.; Kolb, J. F., Elasticity and tumorigenic characteristics of cells in a monolayer after nanosecond pulsed electric field exposure. Eur Biophys J 2017, 46 (6), 567-580.

84. Sweeney, D. C.; Douglas, T. A.; Davalos, R. V., Characterization of Cell Membrane Permeability In Vitro Part II: Computational Model of Electroporation-Mediated Membrane Transport. Technology in cancer research & treatment 2018, 17, 1533033818792490.

85. Sweeney, D. C.; Reberšek, M.; Dermol, J.; Rems, L.; Miklavčič, D.; Davalos, R. V. J. B. e. B. A.-B., Quantification of cell membrane permeability induced by monopolar and high-frequency bipolar bursts of electrical pulses. 2016, 1858 (11), 2689-2698.

86. Teissie, J., Membrane Permeabilization Lifetime in Experiments. Handbook of Electroporation 2017, 61-75.

87. Teissie, J.; Rols, M. P., Manipulation of cell cytoskeleton affects the lifetime of cell membrane electropermeabilization. Ann N Y Acad Sci 1994, 720 (1), 98-110.

88. Teissie, J.; Rols, M.-P., An experimental evaluation of the critical potential difference inducing cell membrane electropermeabilization. Biophysical journal 1993, 65 (1), 409-413.

89. Tekle, E.; Astumian, R. D.; Chock, P. B., Selective and asymmetric molecular transport across electroporated cell membranes. Proceedings of the National Academy of Sciences 1994, 91 (24), 11512-11516.

90. Théry, M.; Jiménez-Dalmaroni, A.; Racine, V.; Bornens, M.; Jülicher, F., Experimental and theoretical study of mitotic spindle orientation. Nature 2007, 447 (7143), 493.

91. Thompson, G. L.; Roth, C.; Tolstykh, G.; Kuipers, M.; Ibey, B. L., Disruption of the actin cortex contributes to susceptibility of mammalian cells to nanosecond pulsed electric fields. Bioelectromagnetics 2014, 35 (4), 262-72.

92. Thompson, G. L.; Roth, C.; Tolstykh, G.; Kuipers, M.; Ibey, B. L., Role of Cytoskeleton and Elastic Moduli in Cellular Response to Nanosecond Pulsed Electric Fields. In Terahertz and Ultrashort Electromagnetic Pulses for Biomedical Applications, Wilmink, G. J.; Ibey, B. L., Eds. 2013; Vol. 8585.

93. Towhidi, L.; Kotnik, T.; Pucihar, G.; Firoozabadi, S.; Mozdarani, H.; Miklavčič, D., Variability of the minimal transmembrane voltage resulting in detectable membrane electroporation. Electromagnetic biology and medicine 2008, 27 (4), 372-385.

94. Tsong, T. Y., Electroporation of cell membranes. In Electroporation and Electrofusion in Cell Biology, Springer: 1989; pp 149-163.

95. Tu-Sekine, B.; Padhi, A.; Jin, S.; Kalyan, S.; Singh, K.; Apperson, M.; Kapania, R.; Hur, S. C.; Nain, A.; Kim, S. F., Inositol polyphosphate multikinase is a metformin target that regulates cell migration. The FASEB Journal 2019, 33 (12), 14137-14146.

96. Ušaj, M.; Trontelj, K.; Hudej, R.; Kanduser, M.; Miklavčič, D., Cell size dynamics and viability of cells exposed to hypotonic treatment and electroporation for electrofusion optimization. Radiology and Oncology 2009, 43 (2), 108-119.

97. Wang, J.; Nain, A. S., Suspended Micro/Nanofiber Hierarchical Biological Scaffolds Fabricated Using Non-Electrospinning STEP Technique. Langmuir 2014, 30 (45), 13641-13649.

98. Weaver, J. C.; Chizmadzhev, Y. A., Theory of electroporation: a review. Bioelectrochemistry and bioenergetics 1996, 41 (2), 135-160.

99. Weaver, J. C.; Vernier, P. T., Pore lifetimes in cell electroporation: Complex dark pores?arXiv preprint arXiv:1708.07478 2017.

100. Xiao, D.; Tang, L.; Zeng, C.; Wang, J.; Luo, X.; Yao, C.; Sun, C., Effect of actin cytoskeleton disruption on electric pulse-induced apoptosis and electroporation in tumour cells. Cell biology international 2011, 35 (2), 99-104.

101. Xiao, D.; Tang, L.; Zeng, C.; Wang, J.; Luo, X.; Yao, C.; Sun, C., Effect of actin cytoskeleton disruption on electric pulse-induced apoptosis and electroporation in tumour cells. Cell Biol Int 2011, 35 (2), 99-104.

102. Yu, M.; Lin, H., Modeling transport across the electroporated membrane. In Handbook of Electroporation, Springer International Publishing: 2017; pp 1089-1110.

What is claimed is:

1. A method for modifying at least one cell, the method comprising applying an electric field to a nanofiber array comprising the at least one cell, wherein the nanofiber array comprises a first array of first fibers and a second array of second fibers, wherein the first fibers are positioned at an angle of from about 0° to about 90° to the second fibers, wherein the method is conducted in a calcium-free media, and the electric field comprises an electric field strength from about 500 V/cm to about 30,000 V/cm.

2. The method of claim 1, wherein the at least one cell is a mammalian cell, a non-mammalian vertebrate cell, an invertebrate cell, a plant cell, a fungal cell, a bacterial cell, an archaeal cell, a protozoal cell, an engineered cell, or a combination thereof.

3. The method of claim 1, wherein the at least one cell comprises a major axis and a minor axis, and wherein the major axis intersects the minor axis.

4. The method of claim 3, wherein the electric field is applied in a parallel direction with respect to the major axis of the at least one cell.

5. The method of claim 3, wherein the electric field is applied at an angle of from about 0° to about 90° with respect to the major axis of the at least one cell.

6. The method of claim 1, wherein the electric field comprises an electric field strength from about 500 V/cm to about 1,500 V/cm.

7. The method of claim 1, wherein applying the electric field causes the at least one cell to undergo a shape change comprising rounding, membrane blebbing, cytoskeletal reorganization, or any combination thereof.

8. The method of claim 1, wherein applying the electric field causes a characteristic cell force response profile comprising drop in cell force and a recovery stage.

9. The method of claim 8, wherein cell force response is exerted by cells, felt by cells, or a combination thereof.

10. The method of claim 1, wherein the at least one cell has an initial shape comprising an initial cell length and wherein applying the electric field causes the at least one cell to adopt a second length and the second length is shorter than the initial cell length.

11. The method of claim 1, wherein applying an electric field increases membrane permeability of the at least one cell relative to an initial state of membrane permeability.

12. The method of claim 11, wherein the at least one cell returns to the initial state of membrane permeability following removal of the electric field.

13. The method of claim 11, wherein assessing membrane permeability comprises (i) visualizing the at least one cell a first time, (ii) contacting the at least one cell with a membrane-impermeant stain, (iii) visualizing the at least one cell a second time, and (iv) quantifying a difference in images produced by steps (i) and (iii).

14. A method for introducing a compound into at least one cell, the method comprising (i) performing the method of claim 1 and (ii) exposing the at least one cell to the compound.

15. The method of claim 14, wherein the compound comprises nucleic acids, a vector, a peptide or protein, a membrane-impermeant stain, a pharmaceutical compound, a cryoprotectant, one or more exogenous organelles, a molecular probe, nanodevices, nanoparticles, or a combination thereof.

16. The method of claim 1, the method is conducted in the presence of at least one compound that affects cellular properties, the at least one compound comprising a cytochalasin, lactrunculin, jasplakinolide, colchicine, demecolcine, nocodazole, paclitaxel, vinblastine, blebbistatin, W-7 hydrochloride, rho inhibitor I, CCG-1423, NSC 23766, ML 141, CPYPP, LY294002, PF573,228, PF431,396, fasudil, ripasudil, netarsudil, RKI-1447, Y-27632, GSK429286A, Y-30141 or a combination thereof.

17. The method of claim 1, wherein the at least one cell comprises a major axis and a minor axis, and wherein the major axis intersects the minor axis, wherein the electric field is applied in a parallel direction with respect to the major axis of the at least one cell, and the electric field comprises an electric field strength from about 500 V/cm to about 1,500 V/cm.

18. A method for modifying at least one cell, the method comprising applying an electric field to a nanofiber array comprising the at least one cell, wherein the nanofiber array comprises a first array of first fibers and a second array of second fibers, wherein the first fibers are positioned at an angle of from about 0° to about 90° to the second fibers, and wherein the electric field comprises an electric field strength from about 500 V/cm to about 30,000 V/cm.

* * * * *